United States Patent
Blair et al.

(10) Patent No.: US 8,822,522 B2
(45) Date of Patent: Sep. 2, 2014

(54) DUAL-ACTING PYRAZOLE ANTIHYPERTENSIVE AGENTS

(71) Applicants: Brooke Blair, Williamstown, MA (US); Paul R. Fatheree, San Francisco, CA (US); Melissa Fleury, San Francisco, CA (US); Roland Gendron, San Francisco, CA (US); Ryan Hudson, San Jose, CA (US); Robert Murray McKinnell, Millbrae, CA (US); Michael Wilson, Walnut Creek, CA (US)

(72) Inventors: Brooke Blair, Williamstown, MA (US); Paul R. Fatheree, San Francisco, CA (US); Melissa Fleury, San Francisco, CA (US); Roland Gendron, San Francisco, CA (US); Ryan Hudson, San Jose, CA (US); Robert Murray McKinnell, Millbrae, CA (US); Michael Wilson, Walnut Creek, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 33 days.

(21) Appl. No.: 13/685,128

(22) Filed: Nov. 26, 2012

(65) Prior Publication Data
US 2013/0245041 A1   Sep. 19, 2013

Related U.S. Application Data

(63) Continuation of application No. 13/346,237, filed on Jan. 9, 2012, now Pat. No. 8,350,027, which is a continuation of application No. 12/984,070, filed on Jan. 4, 2011, now Pat. No. 8,119,634, which is a continuation of application No. 12/829,667, filed on Jul. 2, 2010, now Pat. No. 7,956,054.

(60) Provisional application No. 61/223,472, filed on Jul. 7, 2009.

(51) Int. Cl.
| | | |
|---|---|---|
| C07D 231/10 | (2006.01) | |
| A61K 31/415 | (2006.01) | |
| C07D 403/10 | (2006.01) | |
| C07D 405/14 | (2006.01) | |
| C07D 403/14 | (2006.01) | |
| C07D 401/14 | (2006.01) | |
| C07D 231/14 | (2006.01) | |
| C07D 231/12 | (2006.01) | |
| C07D 413/10 | (2006.01) | |
| C07D 409/14 | (2006.01) | |
| C07D 403/06 | (2006.01) | |
| C07D 401/06 | (2006.01) | |

(52) U.S. Cl.
CPC ............ *C07D 403/10* (2013.01); *C07D 405/14* (2013.01); *C07D 403/14* (2013.01); *C07D 401/14* (2013.01); *C07D 231/14* (2013.01); *C07D 231/12* (2013.01); *C07D 413/10* (2013.01); *C07D 409/14* (2013.01); *C07D 403/06* (2013.01); *C07D 401/06* (2013.01)
USPC ........................................ 514/406; 548/374.1

(58) Field of Classification Search
CPC ............................ A61K 31/415; C07D 231/10
USPC ........................................ 514/406; 548/374.1
See application file for complete search history.

(56) References Cited

U.S. PATENT DOCUMENTS

| | | |
|---|---|---|
| 4,513,009 A | 4/1985 | Roques et al. |
| 4,610,816 A | 9/1986 | Berger |
| 4,722,810 A | 2/1988 | Delaney et al. |
| 4,929,641 A | 5/1990 | Haslanger et al. |
| 5,030,654 A | 7/1991 | Barnish et al. |
| 5,138,069 A | 8/1992 | Carini et al. |
| 5,155,100 A | 10/1992 | Erion et al. |
| 5,217,996 A | 6/1993 | Ksander |
| 5,270,317 A | 12/1993 | Bernhart et al. |
| 5,294,632 A | 3/1994 | Erion et al. |
| 5,399,578 A | 3/1995 | Buhlmayer et al. |
| 5,444,081 A | 8/1995 | Gleason et al. |
| 5,508,272 A | 4/1996 | Robl |
| 5,587,375 A | 12/1996 | Robl |
| 5,591,762 A | 1/1997 | Hauel et al. |
| 5,616,599 A | 4/1997 | Yanagisawa et al. |
| 5,705,517 A | 1/1998 | Naka et al. |

(Continued)

FOREIGN PATENT DOCUMENTS

| | | |
|---|---|---|
| EP | 0 361 365 A1 | 4/1990 |
| EP | 0 411 507 A1 | 6/1991 |

(Continued)

OTHER PUBLICATIONS

Ashton et al., "Nonpeptide Angiotensin II Antagonists Derived from 4H-1,2,4-triazoles and 3H-Imidazo[1,2-b][1,2,4]triazoles", J. Med. Chem., 36, 591-609 (1993).

(Continued)

*Primary Examiner* — Samantha Shterengarts
(74) *Attorney, Agent, or Firm* — Jeffrey A. Hagenah; Shelley Eberle

(57) ABSTRACT

In one aspect, the invention relates to compounds having the formula:

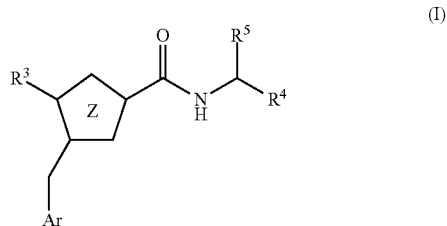

(I)

wherein: Ar, Z, $R^3$, $R^4$ and $R^5$ are as defined in the specification, or a pharmaceutically acceptable salt thereof. These compounds have $AT_1$ receptor antagonist activity and neprilysin inhibition activity. In another aspect, the invention relates to pharmaceutical compositions comprising such compounds; methods of using such compounds; and process and intermediates for preparing such compounds.

5 Claims, No Drawings

(56) References Cited

U.S. PATENT DOCUMENTS

| | | |
|---|---|---|
| 5,864,043 A | 1/1999 | Narr et al. |
| 6,090,828 A | 7/2000 | Reitz |
| 6,602,866 B2 | 8/2003 | Flynn et al. |
| 6,777,443 B2 | 8/2004 | Fink |
| 6,852,745 B2 | 2/2005 | Murugesan et al. |
| 7,060,721 B1 | 6/2006 | Oku et al. |
| 7,777,077 B2 | 8/2010 | Choi et al. |
| 7,834,041 B2 | 11/2010 | Choi et al. |
| 7,863,309 B2 | 1/2011 | Choi et al. |
| 7,879,896 B2 | 2/2011 | Allegretti et al. |
| 7,989,484 B2 | 8/2011 | Allegretti et al. |
| 8,013,005 B2 | 9/2011 | Allegretti et al. |
| 8,212,052 B2 | 7/2012 | Choi et al. |
| 2003/0144215 A1 | 7/2003 | Ksander et al. |
| 2004/0048911 A1 | 3/2004 | Reitz et al. |
| 2006/0046978 A1 | 3/2006 | Pierau et al. |
| 2008/0318951 A1 | 12/2008 | Allegretti et al. |
| 2011/0021527 A1 | 1/2011 | Fatheree et al. |
| 2011/0178101 A1 | 7/2011 | Fatheree et al. |

FOREIGN PATENT DOCUMENTS

| | | |
|---|---|---|
| EP | 0 437 103 A2 | 7/1991 |
| EP | 0 505 954 A1 | 9/1992 |
| EP | 0 726 072 A2 | 8/1996 |
| JP | 06 184086 | 7/1994 |
| JP | 07 048360 | 2/1995 |
| JP | 2003 048874 | 2/2003 |
| WO | WO 92/13564 | 8/1992 |
| WO | WO 00/01389 A2 | 1/2000 |
| WO | WO 2006/027680 A1 | 3/2006 |
| WO | WO 2006/086456 A2 | 8/2006 |
| WO | WO 2007/045663 A2 | 4/2007 |
| WO | WO 2007/056546 A1 | 5/2007 |
| WO | WO 2007/106708 A2 | 9/2007 |
| WO | WO 2007/109456 A2 | 9/2007 |
| WO | WO 2008/142576 A2 | 11/2008 |

OTHER PUBLICATIONS

Fournie-Zaluski et al., "Design of Orally Active Dual Inhibitors of Neutral Endopeptidase and Angiotensin-Converting Enzyme with long Duration of Action" *Journal of Medicinal Chemistry* 39:2594-2608 (1996).

Gardiner et al., "Regional hemodynamic effects of neutral endopeptidase inhibition and angiotensin (AT1) receptor antagonism alone or in combination in conscious spontaneously hypertensive rats", The Journal of Pharmacology and Experimental Therapeutics, vol. 319 No. 1, pp. 340-348 (2006).

Middlemiss et al., "Benzofuran based angiotensin II antagonists related to GR117289: Part II; amino acid amides", Bioorganic & Medicinal Chemistry Letters, vol. 3, No. 10, pp. 2043-2046 (1993).

Pu et al., "The effect of combined AT1 receptor antagonist and neutral endopeptidase (NEP) inhibitor compared to the dual angiotensin converting enzyme inhibitor/NEP on endothelial function and vascular remodeling of SHRSP", Abstract presented at the Canadian Cardiovascular Congress (Oct. 2004).

Robl et al., "Recent advances in the design and development of vasopeptidase inhibitors", Expert Opinion on Therapeutic Patents, 9(12), pp. 1665-1677 (1999).

Shah et al., "Angiotensin II-AT$_1$ Receptor Antagonist: design, synthesis and evaluation of substituted carboxamido benzoimidazole derivatives", *European Journal of Medicinal Chemistry*, 43(9), pp. 1808-1812 (2008).

International Search Report for PCT/US2010/040880 dated Sep. 30, 2010.

DUAL-ACTING PYRAZOLE ANTIHYPERTENSIVE AGENTS

CROSS-REFERENCE TO RELATED APPLICATIONS

This application is a continuation of U.S. Ser. No. 13/346,237, filed Jan. 9, 2012, now allowed; which is a continuation of U.S. Ser. No. 12/984,070, filed Jan. 4, 2011, now issued as U.S. Pat. No. 8,119,634; which is a continuation of U.S. Ser. No. 12/829,667, filed Jul. 2, 2010, now issued as U.S. Pat. No. 7,956,054; which claims the benefit of U.S. Provisional Application No. 61/223,472, filed on Jul. 7, 2009; the entire disclosures of which are incorporated herein by reference.

BACKGROUND OF THE INVENTION

1. Field of the Invention

The present invention relates to novel compounds having angiotensin II type 1 ($AT_1$) receptor antagonist activity and neprilysin-inhibition activity. The invention also relates to pharmaceutical compositions comprising such compounds, processes and intermediates for preparing such compounds and methods of using such compounds to treat diseases such as hypertension.

2. State of the Art

The aim of antihypertensive therapy is to lower blood pressure and prevent hypertension-related complications such as myocardial infarction, stroke, and renal disease. For patients with uncomplicated hypertension (that is, no risk factors, target organ damage, or cardiovascular disease), it is hoped that reducing blood pressure will prevent development of cardiovascular and renal comorbidities, conditions that exist at the same time as the primary condition in the same patient. For those patients with existing risk factors or comorbidities, the therapeutic target is the slowing of comorbid disease progression and reduced mortality.

Physicians generally prescribe pharmacological therapies for patients whose blood pressure cannot be adequately controlled by dietary and/or lifestyle modifications. Commonly used therapeutic classes act to promote diuresis, adrenergic inhibition, or vasodilation. A combination of drugs is often prescribed, depending upon what comorbidities are present.

There are five common drug classes used to treat hypertension: diuretics, which include thiazide and thiazide-like diuretics such as hydrochlorothiazide, loop diuretics such as furosemide, and potassium-sparing diuretics such as triamterene; $\beta_1$ adrenergic receptor blockers such as metoprolol succinate and carvedilol; calcium channel blockers such as amlodipine; angiotensin-converting enzyme (ACE) inhibitors such as captopril, benazepril, enalapril, enalaprilat, lisinopril, quinapril, and ramipril; and $AT_1$ receptor antagonists, also known as angiotensin II type 1 receptor blockers (ARBs), such as candesartan cilexetil, eprosartan, irbesartan, losartan, olmesartan medoxomil, telmisartan, and valsartan. Combinations of these drugs are also administered, for example, a calcium channel blocker (amlodipine) and an ACE inhibitor (benazepril), or a diuretic (hydrochlorothiazide) and an ACE inhibitor (enalapril). All of these drugs, when used appropriately, are effective in the treatment of hypertension. Nevertheless, both efficacy and tolerability should be further improved in new drugs targeting hypertension. Despite the availability of many treatment options, the recent National Health And Nutrition Examination Survey (NHANES) demonstrated that only about 50% of all treated patients with hypertension achieve adequate blood pressure control. Furthermore, poor patient compliance due to tolerability issues with available treatments further reduces treatment success.

In addition, each of the major classes of antihypertensive agents have some drawbacks. Diuretics can adversely affect lipid and glucose metabolism, and are associated with other side effects, including orthostatic hypotension, hypokalemia, and hyperuricemia. Beta blockers can cause fatigue, insomnia, and impotence; and some beta blockers can also cause reduced cardiac output and bradycardia, which may be undesirable in some patient groups. Calcium channel blockers are widely used but it is debatable as to how effectively these drugs reduce fatal and nonfatal cardiac events relative to other drug classes. ACE inhibitors can cause coughing, and rarer side effects include rash, angioedema, hyperkalemia, and functional renal failure. $AT_1$ receptor antagonists are equally effective as ACE inhibitors but without the high prevalence of cough.

Neprilysin (neutral endopeptidase, EC 3.4.24.11) (NEP), is an endothelial membrane bound $Zn^{2+}$ metallopeptidase found in many tissues, including the brain, kidney, lungs, gastrointestinal tract, heart, and peripheral vasculature. NEP is responsible for the degradation and inactivation of a number of vasoactive peptides, such as circulating bradykinin and angiotensin peptides, as well as the natriuretic peptides, the latter of which have several effects including vasodilation and diuresis. Thus, NEP plays an important role in blood pressure homeostasis. NEP inhibitors have been studied as potential therapeutics, and include thiorphan, candoxatril, and candoxatrilat. In addition, compounds have also been designed that inhibit both NEP and ACE, and include omapatrilat, gempatrilat, and sampatrilat. Referred to as vasopeptidase inhibitors, this class of compounds are described in Robl et al. (1999) *Exp. Opin. Ther. Patents* 9 (12): 1665-1677.

There may be an opportunity to increase anti-hypertensive efficacy when combining $AT_1$ receptor antagonism and NEP inhibition, as evidenced by $AT_1$ receptor antagonist/NEP inhibitor combinations described in WO 9213564 to Darrow et al (Schering Corporation); US20030144215 to Ksander et al.; Pu et al., Abstract presented at the Canadian Cardiovascular Congress (October 2004); and Gardiner et al. (2006) *JPET* 319:340-348; and WO 2007/045663 (Novartis AG) to Glasspool et al.

Recently, WO 2007/056546 (Novartis AG) to Feng et al. has described complexes of an $AT_1$ receptor antagonist and a NEP inhibitor, where an $AT_1$ receptor antagonist compound is non-covalently bound to a NEP inhibitor compound, or where the antagonist compound is linked via non-covalent bonding to the inhibitor compound.

In spite of the advances in the art, there remains a need for a highly efficacious monotherapy with multiple mechanisms of action leading to levels of blood pressure control that can currently only be achieved with combination therapy. Thus, although various hypertensive agents are known, and administered in various combinations, it would be highly desirable to provide compounds having both $AT_1$ receptor antagonist activity and NEP inhibition activity in the same molecule. Compounds possessing both of these activities are expected to be particularly useful as therapeutic agents since they would exhibit antihypertensive activity through two independent modes of action while having single molecule pharmacokinetics.

In addition, such dual-acting compounds are also expected to have utility to treat a variety of other diseases that can be treated by antagonizing the $AT_1$ receptor and/or inhibiting the NEP enzyme.

SUMMARY OF THE INVENTION

The present invention provides novel compounds that have been found to possess $AT_1$ receptor antagonist activity and neprilysin (NEP) enzyme inhibition activity. Accordingly, compounds of the invention are expected to be useful and advantageous as therapeutic agents for treating conditions such as hypertension and heart failure.

One aspect of the invention relates to a compound of formula I:

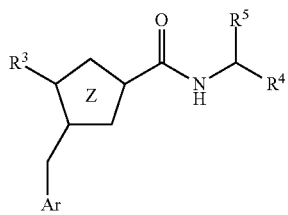

where: Z is a pyrazole selected from:

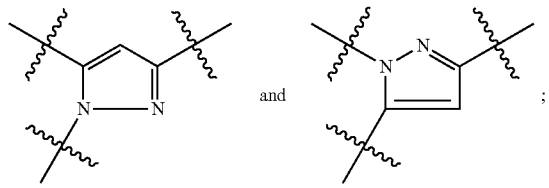 [SMILES: *c1cc(*)n(*)n1 ; *c1cc(*)n(*)n1]

Ar is selected from:

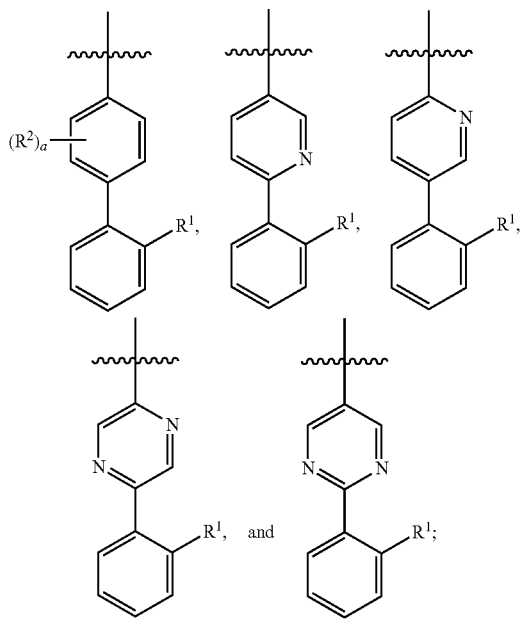

$R^1$ is selected from —$SO_2NHC(O)R^{1a}$, tetrazolyl, —$C(O)OR^{1b}$,

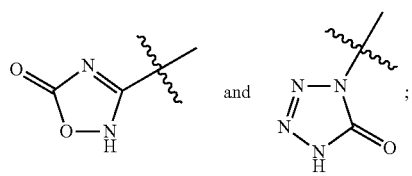

where $R^{1a}$ is —$C_{1-6}$alkyl, —$C_{0-6}$alkylene-OR, —$C_{3-7}$cycloalkyl, —$C_{0-5}$alkylene-$NR^{1b}R^{1b}$, pyridyl, isoxazolyl, methylisoxazolyl, pyrrolidinyl, morpholinyl, and phenyl optionally substituted with halo; where each $R^{1b}$ is independently selected from H and —$C_{1-6}$alkyl;

a is 0, 1, or 2; $R^2$ is F;

$R^3$ is selected from —$C_{2-5}$alkyl and —O—$C_{1-5}$alkyl;

$R^4$ is selected from —$CH_2$—$SR^{4a}$, —$CH_2$—$N(OH)C(O)$H, —$CH(R^{4b})C(O)NH(OR^{4d})$, and —$CH(R^{4b})C(O)OR^{4c}$; where $R^{4a}$ is H or —$C(O)$—$C_{1-6}$alkyl; $R^{4b}$ is H or —OH; $R^{4c}$ is H, —$C_{1-6}$alkyl, —$C_{0-6}$alkylenemorpholine, —$CH_2OC(O)$O—$C_{1-6}$alkyl, —$CH(CH_3)OC(O)O$—$C_{1-6}$alkyl, —$CH(CH_3)OC(O)O$—$C_{3-7}$cycloalkyl, or:

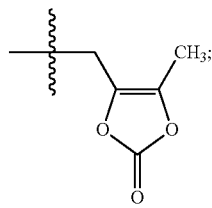 [SMILES: *Cc1oc(=O)oc1C]

$R^{4d}$ is H or —$C(O)$—$R^{4e}$; and $R^{4e}$ is —$C_{1-6}$alkyl, —$C_{1-6}$alkyl-$NH_2$ or aryl; and $R^5$ is selected from —$C_{1-6}$alkyl, —$CH_2$-furanyl, —$CH_2$-thiophenyl, benzyl, and benzyl substituted with one or more halo, —$CH_3$, or —$CF_3$ groups;

where each ring in Ar is optionally substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —$S(O)_2$—$C_{1-4}$alkyl, -phenyl, —$NO_2$, —$NH_2$, —NH—$C_{1-6}$alkyl and —$N(C_{1-6}$alkyl$)_2$, wherein each alkyl, alkenyl and alkynyl is optionally substituted with 1 to 5 fluoro atoms;

or a pharmaceutically acceptable salt thereof.

Another aspect of the invention relates to pharmaceutical compositions comprising a pharmaceutically acceptable carrier and a compound of the invention. Such compositions may optionally contain other therapeutic agents such as diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof. Accordingly, in yet another aspect of the invention, a pharmaceutical composition comprises a compound of the invention, a second therapeutic agent, and a pharmaceutically acceptable carrier. Another aspect of the invention relates to a combination of active agents, comprising a compound of the invention and a second therapeutic agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of the invention and a first pharmaceutically acceptable carrier; and a second pharmaceutical composition comprising a second therapeutic agent and a second pharmaceutically acceptable carrier. In another aspect, the invention relates to a kit containing such pharmaceutical compositions, for example where the first and second pharmaceutical compositions are separate pharmaceutical compositions.

Compounds of the invention possess both $AT_1$ receptor antagonist activity and NEP enzyme inhibition activity, and are therefore expected to be useful as therapeutic agents for treating patients suffering from a disease or disorder that is treated by antagonizing the $AT_1$ receptor and/or inhibiting the NEP enzyme. Thus, one aspect of the invention relates to a method of treating patients suffering from a disease or disorder that is treated by antagonizing the $AT_1$ receptor and/or inhibiting the NEP enzyme, comprising administering to a patient a therapeutically effective amount of a compound of the invention. Another aspect of the invention relates to a method of treating hypertension or heart failure, comprising administering to a patient a therapeutically effective amount of a compound of the invention. Still another aspect of the invention relates to a method for antagonizing an $AT_1$ receptor in a mammal comprising administering to the mammal, an $AT_1$ receptor-antagonizing amount of a compound of the invention. Yet another aspect of the invention relates to a method for inhibiting a NEP enzyme in a mammal comprising administering to the mammal, a NEP enzyme-inhibiting amount of a compound of the invention.

Compounds of the invention that are of particular interest include those that exhibit an inhibitory constant ($pK_i$) for binding to an $AT_1$ receptor greater than or equal to about 5.0; in particular those having a $pK_i$ greater than or equal to about 6.0; in one embodiment those having a $pK_i$ greater than or equal to about 7.0; more particularly those having a $pK_i$ greater than or equal to about 8.0; and in yet another embodiment, those having a $pK_i$ within the range of about 8.0-10.0. Compounds of particular interest also include those having a NEP enzyme inhibitory concentration ($pIC_{50}$) greater than or equal to about 5.0; in one embodiment those having a $pIC_{50}$ greater than or equal to about 6.0; in particular those having a $pIC_{50}$ greater than or equal to about 7.0; and most particularly those having a $pIC_{50}$ within the range of about 7.0-10.0. Compounds of further interest include those having a $pK_i$ for binding to an $AT_1$ receptor greater than or equal to about 7.5 and having a NEP enzyme $pIC_{50}$ greater than or equal to about 7.0.

Since compounds of the invention possess $AT_1$ receptor antagonist activity and NEP inhibition activity, such compounds are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay. Still another aspect of the invention relates to a method of studying a biological system or sample comprising an $AT_1$ receptor, a NEP enzyme, or both, the method comprising: (a) contacting the biological system or sample with a compound of the invention; and (b) determining the effects caused by the compound on the biological system or sample.

Yet another aspect of the invention relates to processes and intermediates useful for preparing compounds of the invention. Accordingly, another aspect of the invention relates to a process of preparing compounds of the invention comprising the step of coupling a compound of formula 1 with a compound of formula 2:

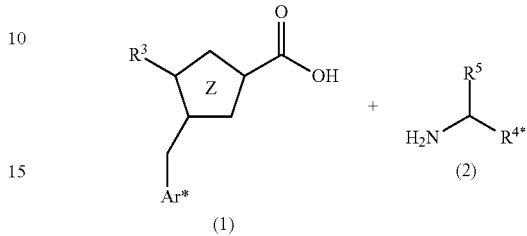

where: Ar* represents Ar—$R^{1*}$, where $R^{1*}$ is $R^1$ or a protected form of $R^1$; and $R^{4*}$ represents $R^4$ or a protected form of $R^4$; and optionally deprotecting the product when $R^{1*}$ is a protected form of $R^1$ and/or $R^{4*}$ is a protected form of $R^4$. Another aspect of the invention relates to a process of preparing a pharmaceutically acceptable salt of a compound of formula I, comprising contacting a compound of formula I in free acid or base form with a pharmaceutically acceptable base or acid. In other aspects, the invention relates to products prepared by any of the processes described herein, as well as novel intermediates used in such process. In one aspect of the invention novel intermediates have formula V, VI or VII, as defined herein.

Yet another aspect of the invention relates to the use of a compound of formula I or a pharmaceutically acceptable salt thereof, for the manufacture of a medicament, especially for the manufacture of a medicament useful for treating hypertension or heart failure. Another aspect of the invention relates to use of a compound of the invention for antagonizing an $AT_1$ receptor or for inhibiting a NEP enzyme in a mammal. Still another aspect of the invention relates to the use of a compound of the invention as a research tool. Other aspects and embodiments of the invention are disclosed herein.

DETAILED DESCRIPTION OF THE INVENTION

In one aspect, the invention relates to compounds of formula I:

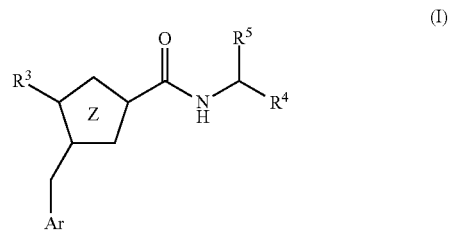

or a pharmaceutically acceptable salt thereof.

As used herein, the term "compound of the invention" includes all compounds encompassed by formula I such as the species embodied in formulas II, III, IV and V. In addition, the compounds of the invention may also contain several basic or acidic groups (for example, amino or carboxyl groups) and therefore, such compounds can exist as a free base, free acid, or in various salt forms. All such salt forms are included within the scope of the invention. Furthermore, the compounds of the invention may also exist as prodrugs. Accordingly, those skilled in the art will recognize that reference to a compound herein, for example, reference to a "compound of the invention" or a "compound of formula I" includes a compound of formula I as well as pharmaceutically acceptable salts and prodrugs of that compound unless otherwise indicated. Further, the term "or a pharmaceutically acceptable salt and/or prodrug thereof" is intended to include all permutations of salts and prodrugs, such as a pharmaceutically acceptable salt of a prodrug. Furthermore, solvates of compounds of formula I are included within the scope of this invention.

The compounds of formula I may contain one or more chiral centers and therefore, these compounds may be prepared and used in various stereoisomeric forms. Accordingly, the invention relates to racemic mixtures, pure stereoisomers (enantiomers or diastereomers), stereoisomer-enriched mixtures, and the like unless otherwise indicated. When a chemical structure is depicted herein without any stereochemistry, it is understood that all possible stereoisomers are encompassed by such structure. Thus, for example, the term "compound of formula I" is intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual enantiomers may be obtained by numerous methods that are well known in the art, including chiral chromatography using a suitable chiral stationary phase or support, or by chemically converting them into diastereomers, separating the diastereomers by conventional means such as chromatography or recrystallization, then regenerating the original enantiomers. Additionally, where applicable, all cis-trans or E/Z isomers (geometric isomers), tautomeric forms and topoisomeric forms of the compounds of the invention are included within the scope of the invention unless otherwise specified.

One possible chiral center could be present at the carbon on the —$CHR^4R^5$ group, when $R^5$ is a group such as —$C_{1-6}$alkyl, for example —$CH_2CH(CH_3)_2$. This chiral center is present at the carbon atom indicated by the symbol *:

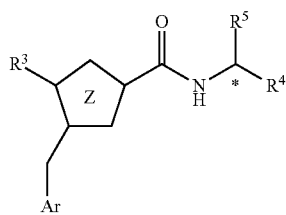

In one embodiment of the invention, the carbon atom identified by the symbol * has the (R) configuration. In this embodiment, compounds of formula I have the (R) configuration at the carbon atom identified by the symbol * or are enriched in a stereoisomeric form having the (R) configuration at this carbon atom. In another embodiment, the carbon atom identified by the symbol * has the (S) configuration. In this embodiment, compounds of formula I have the (S) configuration at the carbon atom identified by the symbol * or are enriched in a stereoisomeric form having the (S) configuration at this carbon atom.

The compounds of the invention can also have two chiral centers on the —$CHR^4R^5$ group, for example when $R^4$ is —CH(OH)C(O)OH and $R^5$ is benzyl. These chiral centers are present at the carbons atom indicated by the symbols * and **:

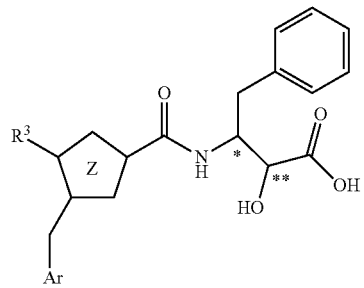

In such cases, four possible diastereomers can exist. For example, both carbon atoms can have the (R) configuration, and in such an embodiment, compounds of formula I have the (R) configuration at the carbon atoms identified by the symbols * and ** or are enriched in a stereoisomeric form having the (R,R) configuration at these atoms. In another embodiment, both carbon atoms can have the (S) configuration, and in such an embodiment, compounds of formula I have the (S,S) configuration at the carbon atoms identified by the symbols * and ** or are enriched in a stereoisomeric form having the (S) configuration at these atoms. In yet another embodiment, the carbon atom identified by the symbol * can have the (S) configuration and the carbon atom identified by the symbol ** can have the (R) configuration, and in such an embodiment, compounds of formula I have the (S,R) configuration at the carbon atoms identified by the symbols * and ** or are enriched in a stereoisomeric form having the (S,R) configuration at these atoms. In still another embodiment, the carbon atom identified by the symbol * can have the (R) configuration and the carbon atom identified by the symbol ** can have the (S) configuration, and in such an embodiment, compounds of formula I have the (R,S) configuration at the carbon atoms identified by the symbols * and ** or are enriched in a stereoisomeric form having the (R,S) configuration at these atoms.

In some cases, in order to optimize the therapeutic activity of the compounds of the invention, for example, as hypertensive agents, it may be desirable that the carbon atom identified by the symbols * and/or ** have a particular (R), (S), (R,R), (S,S), (S,R), or (R,S) configuration.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$.

The compounds of formula I have been found to possess $AT_1$ receptor antagonizing activity and NEP enzyme inhibition activity. Among other properties, such compounds are expected to be useful as therapeutic agents for treating diseases such as hypertension. By combining dual activity into a single compound, double therapy can be achieved, that is, $AT_1$ receptor antagonist activity and NEP enzyme inhibition activity can be obtained using a single active component. Since pharmaceutical compositions containing one active component are typically easier to formulate than compositions containing two active components, such single-component compositions provide a significant advantage over compositions containing two active components. In addition, certain compounds of the invention have also been found to be selective for inhibition of the $AT_1$ receptor over the angiotensin II type 2 ($AT_2$) receptor, a property that may have therapeutic advantages.

The nomenclature used herein to name the compounds of the invention is illustrated in the Examples herein. This nomenclature has been derived using the commercially available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, the invention relates to compounds of formula I:

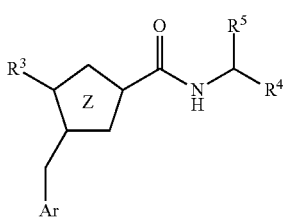

(I)

Z represents a pyrazole selected from:

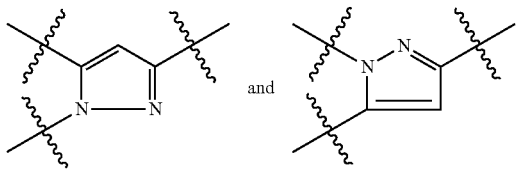

Thus, the compounds of the invention can also be depicted as formulas II and III:

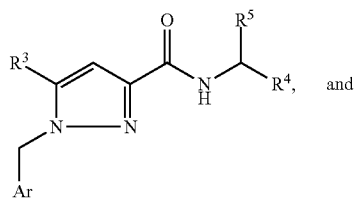

(II)

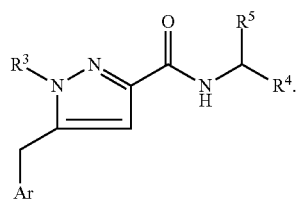

(III)

Ar represents an aryl group selected from:

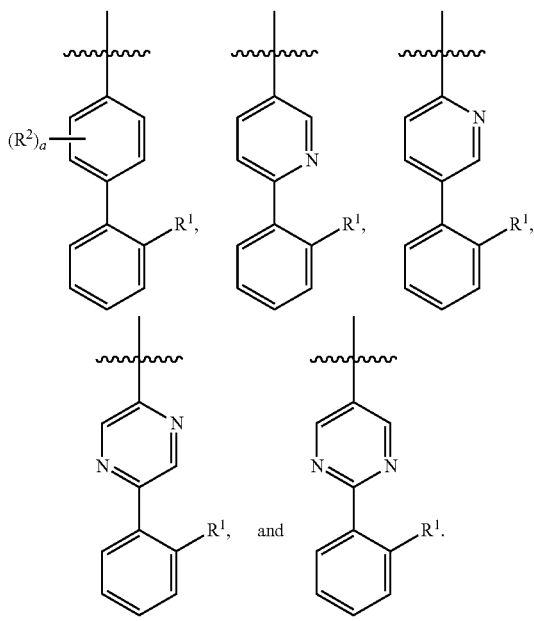

The integer "a" is 0, 1, or 2, and the $R^2$ group is fluoro. Exemplary fluoro-substituted Ar moieties include:

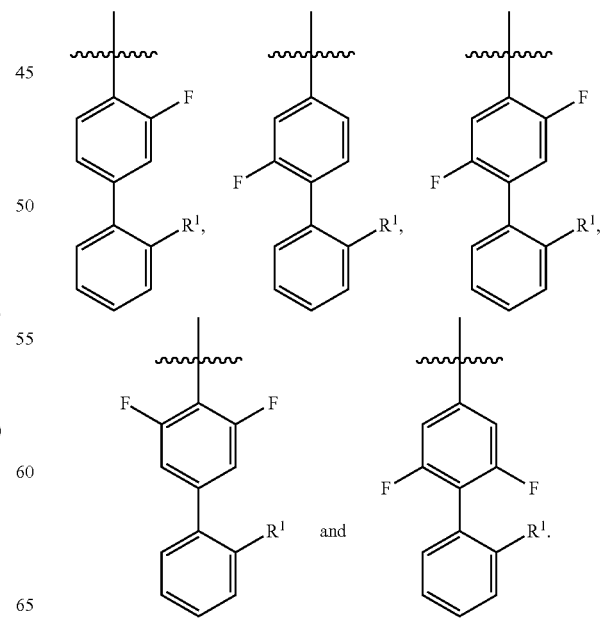

Each ring in Ar may also be substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —NO$_2$, —NH$_2$, —NH—$C_{1-6}$alkyl and —N($C_{1-6}$alkyl)$_2$, wherein each alkyl, alkenyl and alkynyl is optionally substituted with 1 to 5 fluoro atoms.

$R^1$ is selected from —SO$_2$NHC(O)$R^{1a}$, tetrazolyl, —C(O)OR$^{1b}$,

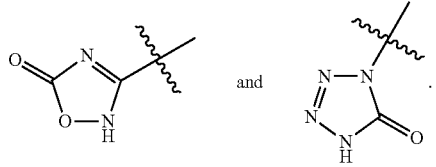 [SMILES: *c1nc(=O)o[nH]1 ; *n1nn[nH]c1=O]

The $R^{1a}$ moiety is —$C_{1-6}$alkyl, —$C_{0-6}$alkylene-OR, —$C_{3-7}$cycloalkyl, —$C_{0-5}$alkylene-NR$^{1b}$R$^{1b}$, pyridyl, isoxazolyl, methylisoxazolyl, pyrrolidinyl, morpholinyl, and phenyl optionally substituted with halo. Each $R^{1b}$ is independently selected from H and —$C_{1-6}$alkyl.

In one particular embodiment, $R^1$ is —SO$_2$NHC(O)$R^{1a}$, where $R^{1a}$ is —$C_{1-6}$alkyl. Examples of this embodiment include —SO$_2$NHC(O)CH$_3$ and SO$_2$NHC(O)CH$_2$CH$_3$. In one particular embodiment, $R^1$ is tetrazolyl such as 1H-tetrazol-5-yl or 5H-tetrazol-5-yl.

In one particular embodiment, $R^1$ is —SO$_2$NHC(O)$R^{1a}$, where $R^{1a}$ is —$C_{0-6}$alkylene-OR. Examples of this embodiment include —SO$_2$NHC(O)OCH$_3$, —SO$_2$NHC(O)OCH$_2$CH$_3$, —SO$_2$NHC(O)CH$_2$OCH$_3$, —SO$_2$NHC(O)CH$_2$OH, —SO$_2$NHC(O)CH(CH$_3$)OH, —SO$_2$NHC(O)C(CH$_3$)$_2$OH, —SO$_2$NHC(O)CH$_2$OCH$_3$, and —SO$_2$NHC(O)(CH$_2$)$_2$OCH$_3$.

In another particular embodiment, $R^1$ is —SO$_2$NHC(O)$R^{1a}$, where $R^{1a}$ is —$C_{3-7}$cycloalkyl. Examples of this embodiment include —SO$_2$NHC(O)-cyclopropyl. In another particular embodiment, $R^1$ is —SO$_2$NHC(O)$R^{1a}$, where $R^{1a}$ is —$C_{0-5}$alkylene-NR$^{1b}$R$^{1b}$. Examples of this embodiment include SO$_2$NHC(O)NH(CH$_3$), —SO$_2$NHC(O)N(CH$_3$)$_2$, —SO$_2$NHC(O)NH(CH$_2$CH$_3$), and —SO$_2$NHC(O)C(CH$_3$)$_2$NH$_2$.

In another particular embodiment, $R^1$ is —SO$_2$NHC(O)$R^{1a}$, where $R^{1a}$ is pyridyl, for example, —SO$_2$NHC(O)-2-pyridyl, —SO$_2$NHC(O)-3-pyridyl, or —SO$_2$NHC(O)-4-pyridyl. The term "pyridyl" means a heterocyclic compound of the formula:

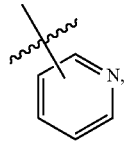

which is bonded to any available point of attachment and includes:

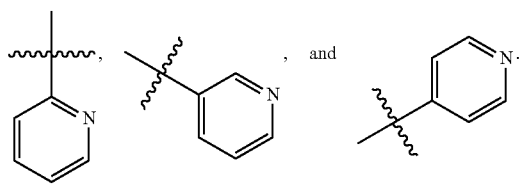 [SMILES: *c1ccccn1 ; *c1cccnc1 ; *c1ccncc1]

In another particular embodiment, $R^1$ is —SO$_2$NHC(O)$R^{1a}$, where $R^{1a}$ is isoxazolyl, for example, —SO$_2$NHC(O)-3-isoxazolyl, —SO$_2$NHC(O)-4-isoxazolyl, and —SO$_2$NHC(O)-5-isoxazolyl. The term "isoxazolyl" means a heterocyclic compound of the formula:

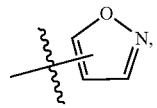

which is bonded to any available point of attachment and includes:

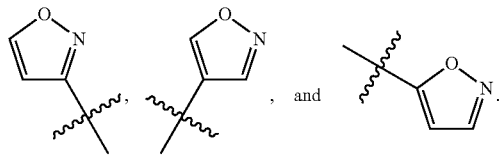 [SMILES: *c1ccon1 ; *c1cnoc1 ; *c1ccno1]

In one particular embodiment, $R^1$ is —SO$_2$NHC(O)$R^{1a}$, where $R^{1a}$ is methylisoxazolyl, for example —SO$_2$NHC(O)-3-isoxazolyl-5-methyl or —SO$_2$NHC(O)-5-isoxazolyl-3-methyl. The term "methylisoxazolyl" means a heterocyclic compound of the formula:

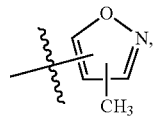

which is bonded to any available point of attachment and includes:

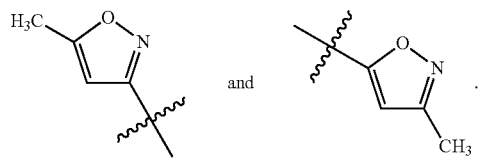

In another particular embodiment, $R^1$ is —SO$_2$NHC(O)$R^{1a}$, where $R^{1a}$ is pyrrolidonyl, for example, —SO$_2$NHC(O)-1-pyrrolidyl, —SO$_2$NHC(O)-2-pyrrolidyl, and —SO$_2$NHC(O)-3-pyrrolidyl. The term "pyrrolidinyl" means a heterocyclic compound of the formula:

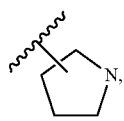

which is bonded to any available point of attachment and includes:

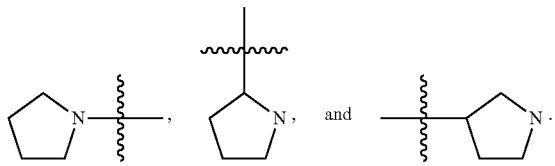 [SMILES: *N1CCCC1 ; *C1CCCN1 ; *C1CCNC1]

In one particular embodiment, $R^1$ is —SO$_2$NHC(O)R$^{1a}$, where $R^{1a}$ is morpholinyl, for example, —SO$_2$NHC(O)-4-morpholinyl. The term "morpholinyl" means a heterocyclic compound of the formula:

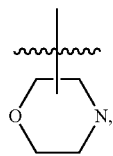

which is bonded to any available point of attachment and includes:

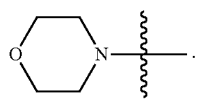

In yet another particular embodiment, $R^1$ is —SO$_2$NHC(O)R$^{1a}$, where $R^{1a}$ is phenyl optionally substituted with halo. In one embodiment, the phenyl group is unsubstituted and $R^1$ is —SO$_2$NHC(O)phenyl. In another embodiment, the phenyl group is substituted with 1 or 2 halo atoms. In yet another embodiment, the halo atoms are fluoro atoms. Examples of this embodiment include —SO$_2$NHC(O)-2-fluorophenyl.

In still another particular embodiment, $R^1$ is tetrazol-5-yl. In still another particular embodiment, $R^1$ is —C(O)OR$^{1b}$, where $R^{1b}$ is H or —C$_{1-6}$alkyl, for example, $R^1$ is —COOH or $R^1$ is —C(O)OCH$_3$. In yet another embodiment, $R^1$ is:

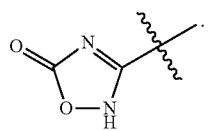 [SMILES: *c1nc(=O)o[nH]1]

And in yet another embodiment, $R^1$ is:

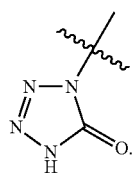

$R^3$ is selected from —C$_{2-5}$alkyl and —O—C$_{1-5}$alkyl. Examples of —C$_{2-5}$alkyl include —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —C(CH$_3$)$_3$, CH(CH$_3$)—CH$_2$CH$_3$, and —(CH$_2$)$_4$CH$_3$. In one embodiment, $R^3$ is propyl, ethyl, or butyl. Examples of —O—C$_{1-5}$alkyl include —OCH$_3$, —OCH$_2$CH$_3$, and —OCH(CH$_3$)$_2$. In one embodiment, $R^3$ is ethoxy.

$R^4$ is selected from —CH$_2$—SR$^{4a}$, —CH$_2$—N(OH)C(O)H, —CH(R$^{4b}$)C(O)NH(OR$^{4d}$), and —CH(R$^{4b}$)C(O)OR$^{4c}$. The R$^{4a}$ moiety is H or —C(O)—C$_{1-6}$alkyl. The R$^{4b}$ moiety is H or —OH, and the R$^{4c}$ moiety is H or —C$_{1-6}$alkyl. The R$^{4d}$ moiety is H or —C(O)—R$^{4e}$, and R$^{4d}$ is —C$_{1-6}$alkyl, —C$_{1-6}$alkyl-NH$_2$ or aryl.

In one particular embodiment, $R^4$ is —CH$_2$—SR$^{4a}$. Examples of this embodiment include —CH$_2$SH and —CH$_2$—S—C(O)CH$_3$.

In another embodiment, $R^4$ is —CH$_2$N(OH)C(O)H. In one particular embodiment, $R^4$ is —CH(R$^{4b}$)C(O)NH(OR$^{4d}$), where R$^{4d}$ moiety is H, such as —CH$_2$C(O)NH(OH) or —CH(OH)C(O)NH(OH). In another particular embodiment, $R^4$ is —CH(R$^{4b}$)C(O)NH(OR$^{4d}$), where R$^{4d}$ moiety is —C(O)—R$^{4e}$, such as —CH$_2$C(O)NH—OC(O)CH$_3$, —CH$_2$C(O)NH—OC(O)-phenyl, or —CH$_2$C(O)NH—OC(O)—CH(NH$_2$)[CH(CH$_3$)$_2$].

In one embodiment, $R^4$ is —CH(R$^{4b}$)C(O)OR$^{4c}$, where R$^{4b}$ and R$^{4c}$ are both H, i.e., $R^4$ is —CH$_2$COOH. In another embodiment, $R^4$ is —CH(R$^{4b}$)C(O)OR$^{4c}$, where R$^{4b}$ is H, and R$^{4c}$ is —C$_{1-6}$alkyl. Such examples of $R^4$ include —CH$_2$C(O)OCH$_3$, —CH$_2$C(O)OCH$_2$CH$_3$, —CH$_2$C(O)OCH(CH$_3$)$_2$, —CH$_2$C(O)O(CH$_2$)$_2$CH$_3$, —CH$_2$C(O)O(CH$_2$)$_3$CH$_3$, and —CH$_2$C(O)O(CH$_2$)$_4$CH$_3$.

In another embodiment, $R^4$ is —CH(R$^{4b}$)C(O)OR$^{4c}$, where R$^{4b}$ is H, and R$^{4c}$ is —C$_{0-6}$alkylenemorpholine, for example $R^4$ can be:

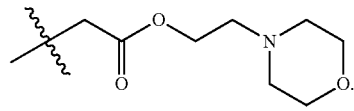 [SMILES: *CC(=O)OCCN1CCOCC1]

In another embodiment, $R^4$ is —CH(R$^{4b}$)COOR$^{4c}$, where R$^{4b}$ is H, and R$^{4c}$ is —CH$_2$OC(O)O—C$_{1-6}$alkyl or —CH(CH$_3$)OC(O)O—C$_{1-6}$alkyl. Examples of such $R^4$ groups include —CH$_2$C(O)OCH(CH$_3$)OC(O)OCH$_2$CH$_3$ and —CH$_2$C(O)OCH(CH$_3$)OC(O)OCH(CH$_3$)$_2$. In another embodiment, $R^4$ is —CH(R$^{4b}$)COOR$^{4c}$, where R$^{4b}$ is H, and R$^{4c}$ is —CH(CH$_3$)OC(O)O—C$_{3-7}$cycloalkyl. Examples of such $R^4$ groups include —CH$_2$C(O)OCH(CH$_3$)OC(O)O-cyclohexyl. In another embodiment, $R^4$ is —CH(R$^{4b}$)C(O)OR$^{4c}$, where R$^{4b}$ is H, and R$^{4c}$ is:

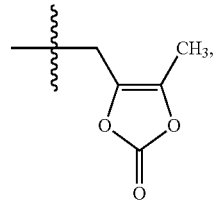 [SMILES: *Cc1oc(=O)oc1C]

for example $R^4$ can be:

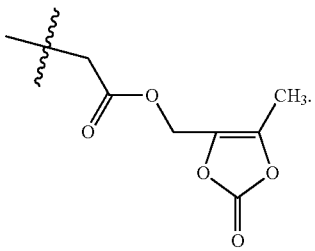

In another embodiment, $R^4$ is —CH($R^{4b}$)COOR$^{4c}$, where $R^{4b}$ is —OH and $R^{4c}$ is H or —$C_{1-6}$alkyl, examples of which include —CH(OH)COOH and —CH(OH)COOCH$_3$.

$R^5$ is selected from —$C_{1-6}$alkyl, —CH$_2$-furanyl, —CH$_2$-thiophenyl, benzyl, and benzyl substituted with one or more halo, —CH$_3$, or —CF$_3$ groups. In one particular embodiment, $R^5$ is —$C_{1-6}$alkyl. Examples of this embodiment include i-butyl. In another embodiment, $R^5$ is —CH$_2$-furanyl such as —CH$_2$-furan-2-yl or —CH$_2$-furan-3-yl. In one particular embodiment, $R^5$ is —CH$_2$-thiophenyl such as —CH$_2$-thiophen-2-yl or —CH$_2$-thiophen-3-yl. In yet another particular embodiment, $R^5$ is benzyl. In still another embodiment, $R^5$ is benzyl substituted with one or more halo, —CH$_3$, or —CF$_3$ groups. Examples of this embodiment include 2-bromobenzyl, 2-chlorobenzyl, 2-fluorobenzyl, 3-fluorobenzyl, 4-fluorobenzyl, 2-methylbenzyl, and 2-trifluoromethylbenzyl.

In one embodiment, $R^4$ is —CH($R^{4b}$)COOR$^{4c}$, where $R^{4b}$H, and $R^5$ is benzyl substituted with one or more halo, —CH$_3$, or —CF$_3$ groups.

In one embodiment of the invention, the compound of formula I is the species embodied in formula II:

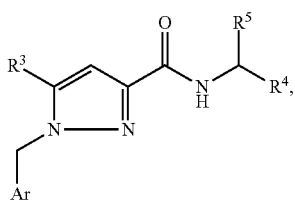

(II)

where Ar, $R^3$, $R^5$ and $R^6$ are as defined for formula I; or a pharmaceutically acceptable salt thereof. In one particular embodiment, Ar is:

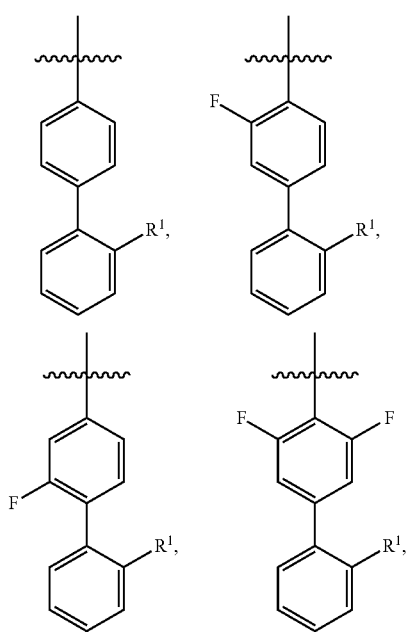

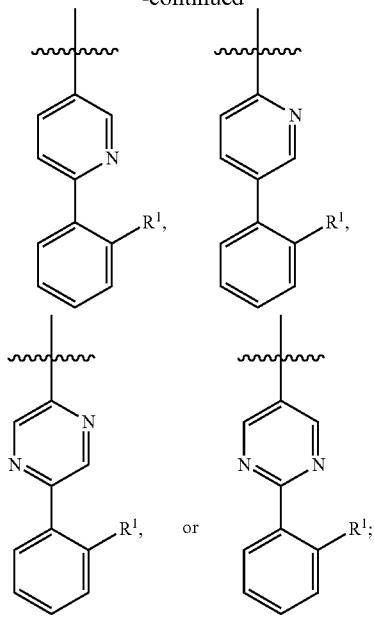

$R^1$ is —SO$_2$NHC(O)CH$_3$, —SO$_2$NHC(O)CH$_2$CH$_3$, —SO$_2$NHC(O)OCH$_3$, —SO$_2$NHC(O)OCH$_2$CH$_3$, —SO$_2$NHC(O)CH$_2$OCH$_3$, —SO$_2$NHC(O)CH$_2$OH, —SO$_2$NHC(O)CH(CH$_3$)OH, —SO$_2$NHC(O)C(CH$_3$)$_2$OH, —SO$_2$NHC(O)CH$_2$OCH$_3$, —SO$_2$NHC(O)(CH$_2$)$_2$OCH$_3$, —SO$_2$NHC(O)-cyclopropyl, —SO$_2$NHC(O)NH(CH$_3$), —SO$_2$NHC(O)N(CH$_3$)$_2$, —SO$_2$NHC(O)NH(CH$_2$CH$_3$), —SO$_2$NHC(O)C(CH$_3$)$_2$NH$_2$, —SO$_2$NHC(O)-2-pyridyl, —SO$_2$NHC(O)-4-pyridyl, —SO$_2$NHC(O)-5-isoxazolyl, SO$_2$NHC(O)-3-isoxazolyl-5-methyl, —SO$_2$NHC(O)-1-pyrrolidyl, —SO$_2$NHC(O)-4-morpholinyl, —SO$_2$NHC(O)phenyl, —SO$_2$NHC(O)-2-fluorophenyl, 1H-tetrazol-5-yl, —COOH, —C(O)OCH$_3$, $R^3$ is propyl, ethyl, butyl, or ethoxy;
$R^4$ is —CH$_2$SH, —CH$_2$—S—C(O)CH$_3$, —CH$_2$N(OH)C(O)H, —CH$_2$C(O)NH(OH), —CH$_2$C(O)NH—OC(O)CH$_3$, —CH$_2$C(O)NH—OC(O)-phenyl, —CH$_2$C(O)NH—OC(O)—CH(NH$_2$)[CH(CH$_3$)$_2$], —CH(OH)C(O)NH(OH), —CH(OH)COOH, —CH(OH)C(O)OCH$_3$, —CH$_2$COOH, —CH$_2$C(O)OCH$_3$, —CH$_2$C(O)OCH$_2$CH$_3$, —CH$_2$C(O)OCH(CH$_3$)$_2$, —CH$_2$C(O)O(CH$_2$)$_2$CH$_3$, —CH$_2$C(O)O(CH$_2$)$_3$CH$_3$, —CH$_2$C(O)O(CH$_2$)$_4$CH$_3$, —CH$_2$C(O)OCH(CH$_3$)OC(O)OCH$_2$CH$_3$, —CH$_2$C(O)OCH(CH$_3$)OC(O)OCH(CH$_3$)$_2$, —CH$_2$C(O)OCH(CH$_3$)OC(O)O-cyclohexyl,

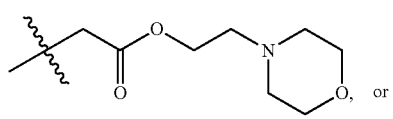

-continued

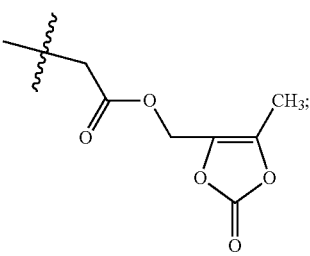 [SMILES: *CC(=O)OCc1oc(=O)oc1C]

and

R⁵ is i-butyl, —CH₂-furan-2-yl, —CH₂-thiophen-3-yl, benzyl, 2-bromobenzyl, 2-chlorobenzyl, 2-fluorobenzyl, 3-fluorobenzyl, 4-fluorobenzyl, 2-methylbenzyl, or 2-trifluoromethylbenzyl;

or a pharmaceutically acceptable salt thereof.

In one embodiment, $R^4$ is selected from —CH₂—SR$^{4a}$, —CH₂—N(OH)C(O)H, —CH(R$^{4b}$)C(O)NH(OR$^{4d}$), and —CH(R$^{4b}$)C(O)OR$^{4c}$; where R$^{4a}$, R$^{4c}$, and R$^{4d}$ are H; and R$^{4b}$ is as defined for formula I. In another aspect, these embodiments have formula II or III.

In yet another embodiment, $R^4$ is selected from —CH₂—SR$^{4a}$, —CH(R$^{4b}$)C(O)NH(OR$^{4d}$), and —CH(R$^{4b}$)C(O)OR$^{4c}$; where R$^{4a}$ is —C(O)—C$_{1-6}$alkyl; R$^{4c}$ is —C$_{1-6}$alkyl, —C$_{0-6}$alkylenemorpholine, —CH₂OC(O)O—C$_{1-6}$alkyl, —CH(CH₃)OC(O)O—C$_{1-6}$alkyl, —CH(CH₃)OC(O)O—C$_{3-7}$cycloalkyl, or:

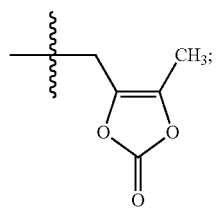 [SMILES: *Cc1oc(=O)oc1C]

R$^{4d}$ moiety is —C(O)—R$^{4e}$; and R$^{4b}$ and R$^{4e}$ are as defined for formula I. In one aspect of the invention, these compounds may find particular utility as prodrugs or as intermediates in the synthetic procedures described herein. In another aspect, these embodiments have formula II or III.

In one aspect, the invention relates to compounds of formula IV:

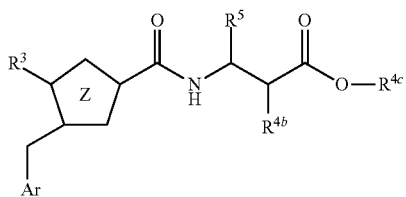

(IV)

where Ar, R³, R$^{4b}$, R$^{4c}$, and R⁵ are as defined for formula I; or a pharmaceutically acceptable salt thereof. In one particular embodiment, Z is:

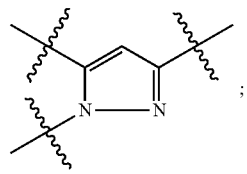 [SMILES: *c1cc(*)n(*)n1]

Ar is:

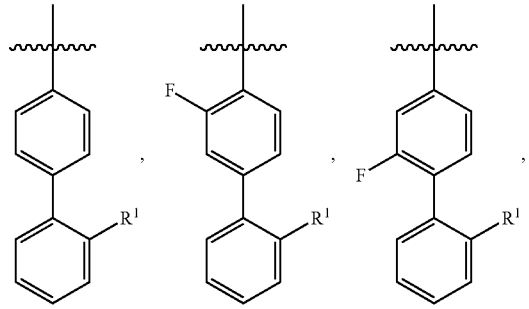

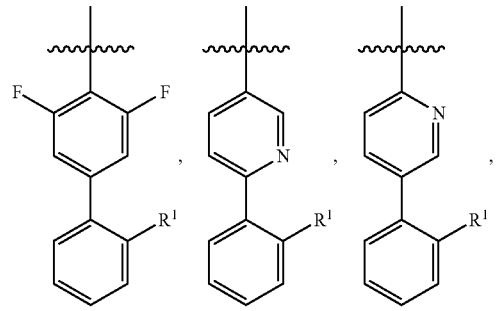

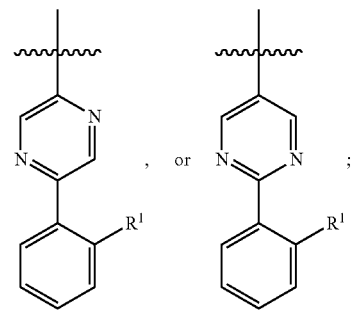

R¹ is —SO₂NHC(O)CH₃, —SO₂NHC(O)CH₂CH₃, —SO₂NHC(O)OCH₃, —SO₂NHC(O)OCH₂CH₃, —SO₂NHC(O)CH₂OCH₃, —SO₂NHC(O)CH₂OH, —SO₂NHC(O)CH(CH₃)OH, —SO₂NHC(O)C(CH₃)₂OH, —SO₂NHC(O)CH₂OCH₃, —SO₂NHC(O)(CH₂)₂OCH₃, —SO₂NHC(O)-cyclopropyl, —SO₂NHC(O)NH(CH₃), —SO₂NHC(O)N(CH₃)₂, —SO₂NHC(O)NH(CH₂CH₃), SO₂NHC(O)C(CH₃)₂NH₂, —SO₂NHC(O)-2-pyridyl, —SO₂NHC(O)-4-pyridyl, —SO₂NHC(O)-5-isoxazolyl, —SO₂NHC(O)-3-isoxazolyl-5-methyl, —SO₂NHC(O)-1-pyrrolidyl, —SO₂NHC(O)-4-morpholinyl, —SO₂NHC(O)phenyl, —SO₂NHC(O)-2-fluorophenyl, 1H-tetrazol-5-yl, —COOH, —C(O)OCH₃,

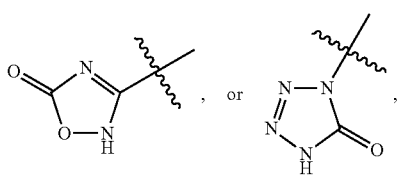 [SMILES: *c1nc(=O)o[nH]1 ; *n1nn[nH]c1=O]

$R^3$ is propyl, ethyl, butyl, or ethoxy;
$R^{4b}$ is H or —OH; and $R^{4c}$ is H, —CH$_3$, —CH$_2$CH$_3$, —CH(CH$_3$)$_2$, —(CH$_2$)$_2$CH$_3$, —(CH$_2$)$_3$CH$_3$, —(CH$_2$)$_4$CH$_3$, —CH(CH$_3$)OC(O)OCH$_2$CH$_3$, —CH(CH$_3$)OC(O)OCH(CH$_3$)$_2$, —CH(CH$_3$)OC(O)O-cyclohexyl,

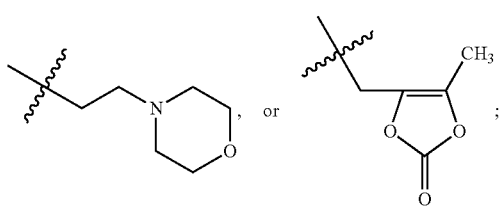

and
$R^5$ is i-butyl, —CH$_2$-furan-2-yl, —CH$_2$-thiophen-3-yl, benzyl, 2-bromobenzyl, 2-chlorobenzyl, 2-fluorobenzyl, 3-fluorobenzyl, 4-fluorobenzyl, 2-methylbenzyl, or 2-trifluoromethylbenzyl;
or a pharmaceutically acceptable salt thereof.

In addition, particular compounds of formula I that are of interest include those set forth in the Examples below, as well a pharmaceutically acceptable salt thereof.

DEFINITIONS

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —C$_{1-4}$alkyl, —C$_{1-5}$alkyl, —C$_{2-5}$alkyl, —C$_{1-6}$alkyl, and —C$_{1-10}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—C$_{1-6}$alkyl" means an alkyl group having from 1 to 6 carbon atoms, and the term "—C$_{3-7}$cycloalkyl" means a cycloalkyl group having from 3 to 7 carbon atoms, respectively, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, —C$_{0-1}$alkylene-, —C$_{0-2}$alkylene-, —C$_{0-3}$alkylene-, —C$_{0-5}$alkylene-, —C$_{0-6}$alkylene-, —C$_{1-2}$alkylene- and —C$_{1-12}$alkylene-. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —C$_{0-5}$alkylene- or —C$_{0-6}$alkylene-, such terms are intended to include the absence of carbon atoms, that is, the alkylene group is not present except for a covalent bond attaching the groups separated by the alkylene term.

The term "alkoxy" means a monovalent group of the formula —O-alkyl, where alkyl is as defined herein. Unless otherwise defined, such alkoxy groups typically contain from 1 to 10 carbon atoms and include, for example, —O—C$_{1-4}$alkyl and —O—C$_{1-5}$alkyl. Representative alkoxy groups include, by way of example, methoxy, ethoxy, n-propoxy, isopropoxy, n-butoxy, sec-butoxy, isobutoxy, t-butoxy and the like.

The term "cycloalkyl" means a monovalent saturated carbocyclic hydrocarbon group. Unless otherwise defined, such cycloalkyl groups typically contain from 3 to 10 carbon atoms and include, for example, —C$_{3-5}$cycloalkyl, —C$_{3-6}$cycloalkyl and —C$_{3-7}$cycloalkyl. Representative cycloalkyl groups include, by way of example, cyclopropyl, cyclobutyl, cyclopentyl, cyclohexyl and the like. The term "cycloalkylene" means a divalent aryl group such as —C$_{4-8}$cycloalkylene.

The term "halo" means fluoro, chloro, bromo and iodo.

As used herein, the phrase "having the formula" or "having the structure" is not intended to be limiting and is used in the same way that the term "comprising" is commonly used.

The term "optionally substituted" means that group in question may be unsubstituted or it may be substituted one or several times, such as 1 to 3 times or 1 to 5 times. For example, a phenyl group that is "optionally substituted" with halo atoms, may be unsubstituted, or it may contain 1, 2, 3, 4, or 5 halo atoms.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "protected derivatives thereof" means a derivative of the specified compound in which one or more functional groups of the compound are protected or blocked from undergoing undesired reactions with a protecting or blocking group. Functional groups that may be protected include, by way of example, carboxy groups, amino groups, hydroxyl groups, thiol groups, carbonyl groups and the like. Representative protecting groups for carboxy groups include esters (such as a p-methoxybenzyl ester), amides and hydrazides; for amino groups, carbamates (such as t-butoxycarbonyl) and amides; for hydroxyl groups, ethers and esters; for thiol groups, thioethers and thioesters; for carbonyl groups, acetals and ketals; and the like. Such protecting groups are well known to those skilled in the art and are described, for example, in T. W. Greene and G. M. Wuts, *Protecting Groups in Organic Synthesis*, Third Edition, Wiley, New York, 1999, and references cited therein.

As used herein, the term "prodrug" is intended to mean an inactive (or significantly less active) precursor of a drug that is converted into its active form in the body under physiological conditions, for example, by normal metabolic processes. The term is also intended to include certain protected derivatives of compounds of formula I that may be made prior to a final deprotection stage. Such compounds may not possess pharmacological activity at $AT_1$ and/or NEP, but may be administered orally or parenterally and thereafter metabolized in the body to form compounds of the invention which are pharmacologically active at $AT_1$ and/or NEP. Thus, all protected derivatives and prodrugs of compounds formula I are included within the scope of the invention. Prodrugs of compounds of formula I having a free carboxyl, sulfhydryl or hydroxy group can be readily synthesized by techniques that are well known in the art. These prodrug derivatives are then converted by solvolysis or under physiological conditions to be the free carboxyl, sulfhydryl and/or hydroxy compounds. Exemplary prodrugs include: esters including $C_{1-6}$alkylesters and aryl-$C_{1-6}$alkylesters, carbonate esters, hemi-esters, phosphate esters, nitro esters, sulfate esters, sulfoxides, amides, carbamates, azo-compounds, phosphamides, glycosides, ethers, acetals, ketals, and disulfides. In one embodiment, the compounds of formula I have a free sulfhydryl or a free carboxyl and the prodrug is an ester derivative thereof, i.e., the prodrug is a thioester such as —SC(O)CH$_3$ or an ester such as —C(O)OCH$_3$.

The term "solvate" means a complex or aggregate formed by one or more molecules of a solute, for example, a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessary be a therapeutic result. For example, when studying a system comprising an $AT_1$ receptor, an "effective amount" may be the amount needed to antagonize the receptor.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, that is, by prophylactic treatment of a patient; (b) ameliorating the disease or medical condition such as by eliminating or causing regression of the disease or medical condition in a patient; (c) suppressing the disease or medical condition such as by slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which compounds of the invention are being evaluated or being used in a assay, for example an animal model.

All other terms used herein are intended to have their ordinary meaning as understood by those of ordinary skill in the art to which they pertain.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein. More specifically, the following abbreviations and reagents are used in the schemes presented below:

$P^1$ represents an "amino-protecting group," a term used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Standard deprotection techniques are used to remove the $P^1$ group. For example, a BOC group can be removed using an acidic reagent such as TFA in DCM or HCl in 1,4-dioxane, while a Cbz group can be removed by employing catalytic hydrogenation conditions such as $H_2$ (1 atm) and 10% Pd/C in an alcoholic solvent ("$H_2$/Pd/C").

$P^2$ represents a "carboxy-protecting group," a term used herein to mean a protecting group suitable for preventing undesired reactions at a carboxy group. Representative carboxy-protecting groups include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Standard deprotection techniques and reagents are used to remove the $P^2$ group, and may vary depending upon which group is used. For example, sodium or lithium hydroxide is commonly used when $P^2$ is methyl, an acid such as TFA or HCl is commonly used when $P^2$ is t-butyl, and $H_2$/Pd/C may be used when $P^2$ is benzyl.

$P^3$ represents a "thiol-protecting group," a term used herein to mean a protecting group suitable for preventing undesired reactions at a thiol group. Representative thiol-protecting groups include, but are not limited to, ethers, esters such as —C(O)CH$_3$, and the like. Standard deprotection techniques and reagents such as NaOH, primary alkylamines, and hydrazine, may be used to remove the $P^3$ group.

$P^4$ represents a "tetrazole-protecting group," a term used herein to mean a protecting group suitable for preventing undesired reactions at a tetrazole group. Representative tetrazole-protecting groups include, but are not limited to trityl and diphenylmethyl. Standard deprotection techniques and reagents such as TFA in DCM or HCl in 1,4-dioxane may be used to remove the $P^4$ group.

$P^5$ represents a "hydroxyl-protecting group," a term that is used herein to mean a protecting group suitable for preventing undesired reactions at a hydroxyl group. Representative hydroxyl-protecting groups include, but are not limited to $C_{1-6}$alkyls, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenylmethyl (Fm), and diphenylmethyl (benzhydryl, DPM); and the like. Standard deprotection techniques and reagents are used to remove the $P^5$ group, and may vary depending upon which group is used. For example, $H_2$/Pd/C is commonly used when $P^5$ is benzyl, while NaOH is commonly used when $P^5$ is an acyl group.

$P^6$ represents a "sulfonamide-protecting group," a term that is used herein to mean a protecting group suitable for preventing undesired reactions at a sulfonamide group. Representative sulfonamide-protecting groups include, but are not limited to t-butyl and acyl groups. Exemplary acyl groups include aliphatic lower acyl groups such as the formyl, acetyl, phenylacetyl, butyryl, isobutyryl, valeryl, isovaleryl and pivaloyl groups, and aromatic acyl groups such as the benzoyl and 4-acetoxybenzoyl. Standard deprotection techniques and reagents are used to remove the $P^6$ group, and may vary depending upon which group is used. For example, HCl is commonly used when $P^6$ is t-butyl, while NaOH is commonly used when $P^6$ is an acyl group.

In addition, L is used to designate a "leaving group," a term used herein to mean a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, triflate, tosylate, brosylate, nosylate and the like; and acyloxy groups, such as acetoxy, trifluoroacetoxy and the like.

Suitable bases for use in these schemes include, by way of illustration and not limitation, potassium carbonate, calcium carbonate, sodium carbonate, triethylamine, pyridine, 1,8-diazabicyclo-[5.4.0]undec-7-ene (DBU), N,N-diisopropylethylamine (DIPEA), sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), dimethyl sulfoxide (DMSO), toluene, dichloromethane (DCM), chloroform (CHCl$_3$), carbon tetrachloride (CCl$_4$), 1,4-dioxane, methanol, ethanol, water, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), O-(7-azabenzotriazol-1-yl-N,N,N',N'-tetramethyluronium hexafluorophosphate (HATU), dicyclohexylcarbodiimide (DCC), N-(3-dimethylaminopropyl)-N'-ethylcarbodiimide (EDC), carbonyldiimidazole (CDI), and the like. Coupling reactions are conducted in an inert diluent in the presence of a base such as DIPEA, and are performed under conventional amide bond-forming conditions.

All reactions are typically conducted at a temperature within the range of about −78° C. to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, $CHCl_3$, DCM, chloroform); washing (for example, with saturated aqueous NaCl, saturated $NaHCO_3$, $Na_2CO_3$ (5%), $CHCl_3$ or 1M NaOH); drying (for example, over $MgSO_4$, over $Na_2SO_4$, or in vacuo); filtering; crystallizing (for example, from EtOAc and hexane); being concentrated (for example, in vacuo); and/or purification (e.g., silica gel chromatography, flash chromatography, preparative HPLC, reverse phase-HPLC, or crystallization).

By way of illustration, compounds of formula I, as well as their salts, solvates, and prodrugs can be prepared by coupling a compound of formula 1 with a compound of formula 2:

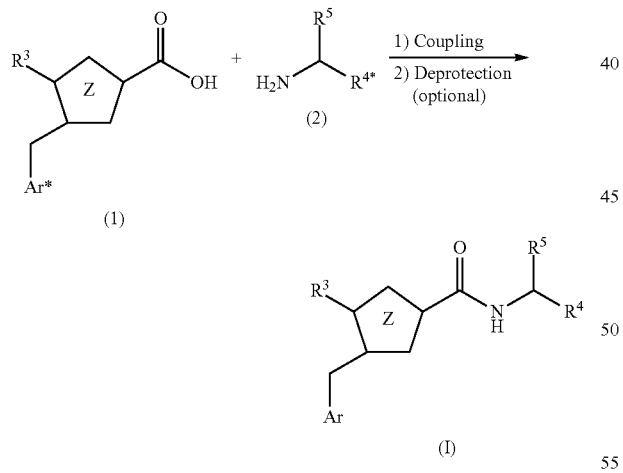

$Ar^*$ represents $Ar—R^{1*}$, where $R^{1*}$ is $R^1$ or a protected form of $R^1$, for example, -tetrazolyl-BOC or a precursor of $R^1$ such as —CN that is then converted to tetrazolyl. $R^{4*}$ represents $R^4$ or a protected form of $R^4$. Therefore, when $R^{1*}$ represents $R^1$ and $R^{4*}$ represents $R^4$, the reaction is complete after the coupling step.

On the other hand, when $R^{1*}$ represents a protected form of $R^1$ and/or $R^{4*}$ represents a protected form of $R^4$, a subsequent global or sequential deprotection step would yield the non-protected compound. Similarly, when $R^{1*}$ represents a precursor of $R^1$, a subsequent conversion step would yield the desired compound. Reagents and conditions for the deprotection vary with the nature of protecting groups in the compound. Thus, one method of preparing compounds of the invention involves coupling compounds (1) and (2), with an optional deprotection step when $R^{1*}$ is a protected form of $R^1$ and/or $R^{4*}$ is a protected form of $R^4$, thus forming a compound of formula I or a pharmaceutically acceptable salt thereof.

Certain intermediates described herein are believed to be novel and accordingly, such compounds are provided as further aspects of the invention including, for example, the compounds of formulas V, VI and VII, or a salt thereof:

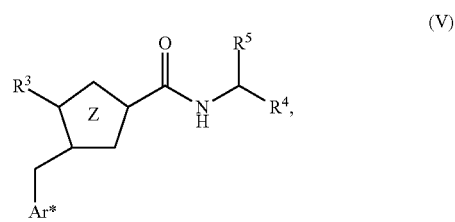

where $Ar^*$ is $Ar—R^{1*}$; Ar, Z, $R^3$, $R^4$, and $R^5$ are as defined for formula I; and $R^{1*}$ is $—SO_2NH—P^6$ or tetrazolyl-$P^4$; where $P^4$ is a tetrazole-protecting group and $P^6$ is a sulfonamide-protecting group;

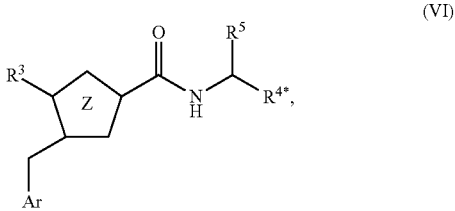

where Ar, Z, $R^3$, and $R^5$ are as defined for formula I; $R^{4*}$ is $—CH_2—S—P^3$, $CH_2—N(O—P^5)—C(O)H$, $—CH(R^{4b})C(O)NH(O—P^5)$, or $—CH(R^{4b})C(O)O—P^2$; and $R^{4b}$ is as defined for formula I; where $P^2$ is a carboxy-protecting group, $P^3$ is a thiol-protecting group, $P^5$ is a hydroxyl-protecting group; and

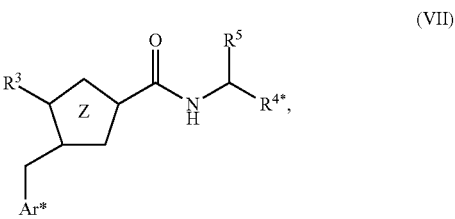

where $Ar^*$ is $Ar—R^{1*}$; Ar, Z, $R^3$, and $R^5$ are as defined for formula I; $R^{1*}$ is $—SO_2NH—P^6$ or tetrazolyl-$P^4$; $R^{4*}$ is $—CH_2—S—P^3$, $—CH_2—N(O—P^5)—C(O)H$, $—CH(R^{4b})C(O)NH(O—P^5)$, or $—CH(R^{4b})C(O)O—P^2$; and $R^{4b}$ is as defined for formula I; where $P^2$ is a carboxy-protecting group, $P^3$ is a thiol-protecting group, $P^4$ is a tetrazole-protecting group, $P^5$ is a hydroxyl-protecting group, and $P^6$ is a sulfonamide-protecting group. Thus, another method of preparing compounds of the invention involves deprotecting a compound of formula V, VI, or VII.

Further details regarding specific reaction conditions and other procedures for preparing representative compounds of the invention or intermediates thereof are described in the Examples set forth below.

Utility

Compounds of the invention possess angiotensin II type 1 ($AT_1$) receptor antagonist activity. In one embodiment, compounds of the invention are selective for inhibition of the $AT_1$ receptor over the $AT_2$ receptor. Compounds of the invention also possess neprilysin (NEP) inhibition activity, that is, the compounds are able to inhibit enzyme-substrate activity. In another embodiment, the compounds do not exhibit significant inhibitory activity of the angiotensin-converting enzyme. Compounds of formula I may be active drugs as well as prodrugs. Thus, when discussing the activity of compounds of the invention, it is understood that any such prodrugs have the expected activity once metabolized.

One measure of the affinity of a compound for the $AT_1$ receptor is the inhibitory constant ($K_i$) for binding to the $AT_1$ receptor. The $pK_i$ value is the negative logarithm to base 10 of the $K_i$. One measure of the ability of a compound to inhibit NEP activity is the inhibitory concentration ($IC_{50}$), which is the concentration of compound that results in half-maximal inhibition of substrate conversion by the NEP enzyme. The $pIC_{50}$ value is the negative logarithm to base 10 of the $IC_{50}$. Compounds of the invention that have both $AT_1$ receptor-antagonizing activity and NEP enzyme-inhibiting activity are of particular interest, including those that exhibit a $pK_i$ at the $AT_1$ receptor greater than or equal to about 5.0, and exhibit a $pIC_{50}$ for NEP greater than or equal to about 5.0.

In one embodiment, compounds of interest have a $pK_i$ at the $AT_1$ receptor≥about 6.0, a $pK_i$ at the $AT_1$ receptor≥about 7.0, or a $pK_i$ at the $AT_1$ receptor≥about 8.0. Compounds of interest also include those having a $pIC_{50}$ for NEP≥about 6.0 or a $pIC_{50}$ for NEP≥about 7.0. In another embodiment, compounds of interest have a $pK_i$ at the $AT_1$ receptor within the range of about 8.0-10.0 and a $pIC_{50}$ for NEP within the range of about 7.0-10.0.

In another embodiment, compounds of particular interest have a $pK_i$ for binding to an $AT_1$ receptor greater than or equal to about 7.5 and a NEP enzyme $pIC_{50}$ greater than or equal to about 7.0. In another embodiment, compounds of interest have a $pK_i$ greater than or equal to about 8.0 and a $pIC_{50}$ greater than or equal to about 8.0.

It is noted that in some cases, compounds of the invention, while still having dual activity, may possess either weak $AT_1$ receptor antagonist activity or weak NEP inhibition activity. In such cases, those of skill in the art will recognize that these compounds still have utility as primarily either a NEP inhibitor or a $AT_1$ receptor antagonist, respectively, or have utility as research tools.

Exemplary assays to determine properties of compounds of the invention, such as the $AT_1$ receptor binding and/or NEP inhibiting activity, are described in the Examples and include by way of illustration and not limitation, assays that measure $AT_1$ and $AT_2$ binding and NEP inhibition (described in Assay 1). Useful secondary assays include assays to measure ACE inhibition (also described in Assay 1) and aminopeptidase P (APP) inhibition (described in Sulpizio et al. (2005) *JPET* 315:1306-1313). A pharmacodynamic assay to assess the in vivo inhibitory potencies for ACE, $AT_1$, and NEP in anesthetized rats is described in Assay 2 (see also Seymour et al. (1985) *Hypertension* 7 (Suppl I):I-35-I-42 and Wigle et al. (1992) *Can. J. Physiol. Pharmacol.* 70:1525-1528), where $AT_1$ inhibition is measured as the percent inhibition of the angiotensin II pressor response, ACE inhibition is measured as the percent inhibition of the angiotensin I pressor response, and NEP inhibition is measured as increased urinary cyclic guanosine 3',5'-monophosphate (cGMP) output. Useful in vivo assays include the conscious spontaneously hypertensive rat (SHR) model, which is a renin dependent hypertension model that is useful for measuring $AT_1$ receptor blocking (described in Assay 3; see also Intengan et al. (1999) *Circulation* 100 (22):2267-2275 and Badyal et al. (2003) *Indian Journal of Pharmacology* 35:349-362), and the conscious desoxycorticosterone acetate-salt (DOCA-salt) rat model, which is a volume dependent hypertension model that is useful for measuring NEP activity (described in Assay 4; see also Trapani et al. (1989) *J. Cardiovasc. Pharmacol.* 14:419-424, Intengan et al. (1999) *Hypertension* 34 (4):907-913, and Badyal et al. (2003) supra). Both the SHR and DOCA-salt models are useful for evaluating the ability of a test compound to reduce blood pressure. The DOCA-salt model is also useful to measure a test compound's ability to prevent or delay a rise in blood pressure. Compounds of the invention are expected to antagonize the $AT_1$ receptor and/or inhibit the NEP enzyme in any of the assays listed above, or assays of a similar nature. Thus, the aforementioned assays are useful in determining the therapeutic utility of compounds of the invention, for example, their utility as antihypertensive agents. Other properties and utilities of compounds of the invention can be demonstrated using other in vitro and in vivo assays well-known to those skilled in the art.

Compounds of the invention are expected to be useful for the treatment and/or prevention of medical conditions responsive to $AT_1$ receptor antagonism and/or NEP inhibition. Thus it is expected that patients suffering from a disease or disorder that is treated by antagonizing the $AT_1$ receptor and/or by inhibiting the NEP enzyme can be treated by administering a therapeutically effective amount of a compound of the invention. For example, by antagonizing the $AT_1$ receptor and thus interfering with the action of angiotensin II on its receptors, these compounds are expected to find utility in preventing the increase in blood pressure produced by angiotensin II, a potent vasopressor. In addition, by inhibiting NEP, the compounds are also expected to potentiate the biological effects of endogenous peptides that are metabolized by NEP, such as the natriuretic peptides, bombesin, bradykinins, calcitonin, endothelins, enkephalins, neurotensin, substance P and vaso-active intestinal peptide. For example, by potentiating the effects of the natriuretic peptides, compounds of the invention are expected to be useful to treat glaucoma. These compounds are also expected to have other physiological actions, for example, on the renal, central nervous, reproductive and gastrointestinal systems.

Compounds of the invention are expected to find utility in treating and/or preventing medical conditions such as cardiovascular and renal diseases. Cardiovascular diseases of particular interest include heart failure such as congestive heart failure, acute heart failure, chronic heart failure, and acute and chronic decompensated heart failure. Renal diseases of particular interest include diabetic nephropathy and chronic kidney disease. One embodiment of the invention relates to a method for treating hypertension, comprising administering to a patient a therapeutically effective amount of a compound of the invention. Typically, the therapeutically effective amount is the amount that is sufficient to lower the patient's blood pressure. In one embodiment, the compound is administered as an oral dosage form.

Another embodiment of the invention relates to a method for treating heart failure, comprising administering to a patient a therapeutically effective amount of a compound of the invention. Typically, the therapeutically effective amount is the amount that is sufficient to lower blood pressure and/or improve renal functions. In one embodiment, the compound is administered as an intravenous dosage form. When used to treat heart failure, the compound may be administered in combination with other therapeutic agents such as diuretics, natriuretic peptides, and adenosine receptor antagonists.

Compounds of the invention are also expected to be useful in preventative therapy, for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

In addition, as NEP inhibitors, compounds of the invention are expected to inhibit enkephalinase, which will inhibit the degradation of endogenous enkephalins and thus such compounds may also find utility as analgesics. Due to their NEP inhibition properties, compounds of the invention are also expected to be useful as antitussive agents and antidiarrheal agents (for example, for the treatment of watery diarrhea), as well as find utility in the treatment of menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction, which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE5 inhibitors, dopamine agonists, estrogen receptor agonists and/or antagonists, androgens, and estrogens.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Since compounds of the invention possess $AT_1$ receptor antagonist activity and/or NEP enzyme inhibition activity, such compounds are also useful as research tools for investigating or studying biological systems or samples having $AT_1$ receptors or a NEP enzyme, for example to study diseases where the $AT_1$ receptor or NEP enzyme plays a role. Any suitable biological system or sample having $AT_1$ receptors and/or a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention an $AT_1$ receptor in a mammal is antagonized by administering an $AT_1$-antagonizing amount of a compound of the invention. In another particular embodiment, NEP enzyme activity in a mammal is inhibited by administering a NEP-inhibiting amount of a compound of the invention. Compounds of the invention can also be used as research tools by conducting biological assays using such compounds.

When used as a research tool, a biological system or sample comprising an $AT_1$ receptor and/or a NEP enzyme is typically contacted with an $AT_1$ receptor-antagonizing or NEP enzyme-inhibiting amount of a compound of the invention. After the biological system or sample is exposed to the compound, the effects of antagonizing the $AT_1$ receptor and/or inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., i.v. or s.c. administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as radioligand binding assays and measuring ligand-mediated changes in functional assays. The assay results can be used to determine the activity level as well as the amount of compound necessary to achieve the desired result, that is, an $AT_1$ receptor-antagonizing and/or a NEP enzyme-inhibiting amount. Typically, the determining step will involve determining the $AT_1$ receptor ligand-mediated effects and/or determining the effects of inhibiting the NEP enzyme.

Additionally, compounds of the invention can be used as research tools for evaluating other chemical compounds, and thus are also useful in screening assays to discover, for example, new compounds having $AT_1$ receptor-antagonizing activity and/or NEP-inhibiting activity. In this manner, a compound of the invention is used as a standard in an assay to allow comparison of the results obtained with a test compound and with compounds of the invention to identify those test compounds that have about equal or superior activity, if any. For example, $K_i$ data (as determined, for example, by a binding assay) for a test compound or a group of test compounds is compared to the $K_i$ data for a compound of the invention to identify those test compounds that have the desired properties, for example, test compounds having a $K_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In formulations where the compound of the invention contains a thiol group, additional consideration may be given to minimize or eliminate oxidation of the thiol to form a disulfide. In solid formulations, this may be accomplished by reducing the drying time, decreasing the moisture content of the formulation, and including materials such as ascorbic acid, sodium ascorbate, sodium sulfite and sodium bisulfate, as well as materials such as a mixture of lactose and microcrystalline cellulose. In liquid formulations, stability of the thiol may be improved by the addition of amino acids, antioxidants, or a combination of disodium edetate and ascorbic acid.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and anti-oxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by a linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system.

Additional excipients including gelling agents, emulsifiers and buffers, may be used in such transdermal compositions if desired.

If desired, the compounds of the invention may be administered in combination with one or more other therapeutic agents. Thus, in one embodiment, pharmaceutical compositions of the invention contain other drugs that are co-administered with a compound of the invention. For example, the composition may further comprise one or more drugs (also referred to as "secondary agents(s)") selected from the group of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof. Such therapeutic agents are well known in the art, and specific examples are described herein. By combining a compound of the invention with a secondary agent, triple therapy can be achieved; $AT_1$ receptor antagonist activity, NEP inhibition activity, and activity associated with the secondary agent (for example, $\beta_1$ adrenergic receptor blocker) can be achieved using only two active components. Since compositions containing two active components are typically easier to formulate than compositions containing three active components, such two-component compositions provide a significant advantage over compositions containing three active components. Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, a compound of the invention is administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with a $\beta_1$ adrenergic receptor blocker. Representative $\beta_1$ adrenergic receptor blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$ adrenergic receptor blocker is selected from atenolol, bisoprolol, metoprolol, propranolol, sotalol, and combinations thereof.

In one embodiment, a compound of the invention is administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexyline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof.

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from: benazepril, enalapril, lisinopril, ramipril, and combinations thereof.

In one embodiment, a compound of the invention is administered in combination with an $AT_1$ receptor antagonist, also known as angiotensin II type 1 receptor blockers (ARBs). Representative ARBs include, but are not limited to, abitesartan, benzyllosartan, candesartan, candesartan cilexetil, elisartan, embusartan, enoltasosartan, eprosartan, fonsartan, forasartan, glycyllosartan, irbesartan, isoteoline, losartan, medoximil, milfasartan, olmesartan, opomisartan, pratosartan, ripisartan, saprisartan, saralasin, sarmesin, tasosartan, telmisartan, valsartan, zolasartan, and combinations thereof. In a particular embodiment, the ARB is selected from candesartan, eprosartan, irbesartan, losartan, olmesartan, irbesartan, saprisartan, tasosartan, telmisartan, and combinations thereof. Exemplary salts include eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

In another embodiment, a compound of the invention is administered in combination with a neprilysin (NEP) inhibitor. Representative NEP inhibitors include, but are not limited to: candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2 (S)-ylcarbonyl]-4(R)-hydroxy-L-proline benzyl ester); 3-(1-carbamoylcyclohexyl) propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl) propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl] carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methyl-pentanoic acid ethyl ester (AHU-377 acid parent and AHU-377ester prodrug; WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from candoxatril, candoxatrilat, CGS-24128, phosphoramidon, SCH-32615, SCH-34826, SQ-28603, thiorphan, AHU-377 (parent or prodrug), and combinations thereof. The NEP inhibitor will be administered in an amount sufficient to provide from about 20-800 mg per day, with typical daily dosages ranging from 50-700 mg per day, more commonly 100-600 or 100-300 mg per day.

In yet another embodiment, a compound of the invention is administered in combination with a non-steroidal anti-inflammatory agent (NSAID). Representative NSAIDs include, but are not limited to: acemetacin, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In yet another embodiment, a compound of the invention is administered in combination with an anti-lipid agent. Representative anti-lipid agents include, but are not limited to, statins such as atorvastatin, fluvastatin, lovastatin, pravastatin, rosuvastatin and simvastatin; cholesteryl ester transfer proteins (CETPs); and combinations thereof.

In yet another embodiment, a compound of the invention is administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In one embodiment, a compound of the invention is administered in combination with an anti-thrombotic agent. Representative anti-thrombotic agents include, but are not limited to, aspirin, anti-platelet agents, heparin, and combinations thereof. Compounds of the invention may also be administered in combination with a renin inhibitor, examples of which include, but are not limited to, aliskiren, enalkiren, remikiren, and combinations thereof. In another embodiment, a compound of the invention is administered in combination with an endothelin receptor antagonist, representative examples of which include, but are not limited to, bosentan, darusentan, tezosentan, and combinations thereof. Compounds of the invention may also be administered in combination with an endothelin converting enzyme inhibitor, examples of which include, but are not limited to, phosphoramidon, CGS 26303, and combinations thereof. In yet another embodiment, a compound of the invention is administered in combination with an aldosterone antagonist, representative examples of which include, but are not limited to, eplerenone, spironolactone, and combinations thereof.

Combined therapeutic agents may also be helpful in further combination therapy with compounds of the invention. For example, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Dual-acting agents may also be helpful in combination therapy with compounds of the invention. For example, angiotensin-converting enzyme/neprilysin (ACE/NEP) inhibitors such as: AVE-0848 ((4S,7S,12bR)-7-[3-methyl-2(S)-sulfanylbutyramido]-6-oxo-1,2,3,4,6,7,8,12b-octahydropyrido[2,1-a][2]benzazepine-4-carboxylic acid); AVE-7688 (ilepatril) and its parent compound; BMS-182657 (2-[2-oxo-3(S)-[3-phenyl-2 (S)-sulfanylpropionamido]-2,3,4,5-tetrahydro-1H-1-benzazepin-1-yl]acetic acid); CGS-26303 ([N-[2-(biphenyl-4-yl)-1(S)-(1H-tetrazol-5-yl) ethyl]amino]methylphosphonic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)—N-[2-(2-hydroxyphenyl)-3-(3-mercaptopropionyl) thiazolidin-4-ylcarbonyl]-L-phenylalanine); Sch-50690 (N-[1(S)-carboxy-2-[N2-(methanesulfonyl)-L-lysylamino] ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine. Exemplary vasopressin receptor antagonists include tolvaptan.

The following formulations illustrate representative pharmaceutical compositions of the invention.

Exemplary Hard Gelatin Capsules for Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (300 mg of composition per capsule).

Alternately, a compound of the invention (40 mg) is thoroughly blended with microcrystalline cellulose (Avicel PH 103; 260 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of the compound of the invention per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% $NaHCO_3$ solution, with or without cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

ACE angiotensin converting enzyme
AcOH acetic acid
APP aminopeptidase P
$AT_1$ angiotensin II type 1 (receptor)
$AT_2$ angiotensin II type 2 (receptor)
BSA bovine serum albumin
DCM dichloromethane or methylene chloride
DIPEA N,N-diisopropylethylamine
DMF N,N-dimethylformamide
DMSO dimethyl sulfoxide
Dnp 2,4-dinitrophenyl
DOCA deoxycorticosterone acetate
EDCI N-(3-dimethylaminopropyl)-N'-ethylcarbodiimide hydrochloride
EDTA ethylenediaminetetraacetic acid
EtOAc ethyl acetate
EtOH ethanol
HATU N,N,N',N'-tetramethyl-O-(7-azabenzotriazol-1-yl) uronium hexafluorophosphate
HOAt 1-hydroxy-7-azabenzotriazole
Mca (7-methoxycoumarin-4-yl)acyl
MeCN acetonitrile
MeOH methanol
NBS N-bromosuccinimide
NEP neprilysin (EC 3.4.24.11)
PBS phosphate buffered saline
SHR spontaneously hypertensive rat
TFA trifluoroacetic acid
THF tetrahydrofuran
Tris tris(hydroxymethyl)aminomethane
Tween-20 polyethylene glycol sorbitan monolaurate Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% $H_2O$/2% MeCN/1.0 mL/L TFA; solvent B was 90% MeCN/10% $H_2O$/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent ($CD_3OD$, $CDCl_3$, or $DMSO$-$d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

5-Propyl-1-[2'-(1-trityl-1H-tetrazol-5-yl)biphenyl-4-ylmethyl]-1H-pyrazole-3-carboxylic Acid

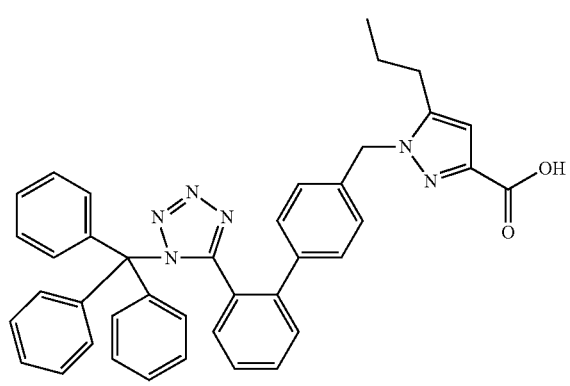 [SMILES: CCCc1cc(C(=O)O)nn1Cc1ccc(-c2ccccc2-c2nnnn2C(c2ccccc2)(c2ccccc2)c2ccccc2)cc1]

Ethyl 3-n-propylpyrazole-5-carboxylate (1.0 g, 5.5 mmol), 5-(4'-bromomethylbiphenyl-2-yl)-1-trityl-1H-tetrazole (3.1 g, 5.5 mmol), and potassium carbonate (1.5 g, 11.0 mmol) were dissolved in DMF (40.0 mL, 516 mmol) and the mixture was stirred at room temperature overnight. LCMS showed the reaction was nearly complete, with a 1:1 mixture of regioisomers. The mixture was partially concentrated, then partitioned between water and EtOAc. The EtOAc layer was then dried over $Na_2SO_4$ and concentrated. The regioisomers were separated by flash chromatography (0-50% EtOAc/hexanes, dry load). Regioisomer identities were confirmed by NOE: 5-propyl-1-[2'-(1-trityl-1H-tetrazol-5-yl)biphenyl-4-ylmethyl]-1H-pyrazole-3-carboxylic acid ethyl ester (1.2 g) and 5-propyl-2-[2'-(1-trityl-1H-tetrazol-5-yl)biphenyl-4-ylmethyl]-2H-pyrazole-3-carboxylic acid ethyl ester (1.1 g).

5-Propyl-1-[2'-(1-trityl-1H-tetrazol-5-yl)biphenyl-4-ylmethyl]-1H-pyrazole-3-carboxylic acid ethyl ester (400 mg, 607 µmol) was dissolved in THF (12.0 mL, 148 mmol). A solution of LiOH monohydrate (127 mg, 3.04 mmol) in water (4.0 mL, 222 mmol) was then added and the mixture was stirred at room temperature for about 19 hours. The mixture was then heated to 60° C. overnight. LCMS showed that the reaction was complete, but that two additional side products had also formed. The mixture was partitioned between EtOAc and a saturated ammonium chloride solution. The EtOAc layer was dried over $Na_2SO_4$ and concentrated to yield the title compound (340 mg). LCMS showed that the side products were no longer present.

Example 1

(2R,3R)-3-(1-((2'-(1H-tetrazol-5-yl)biphenyl-4-yl)methyl)-5-propyl-1H-pyrazole-3-carboxamido)-2-hydroxy-4-phenylbutanoic Acid

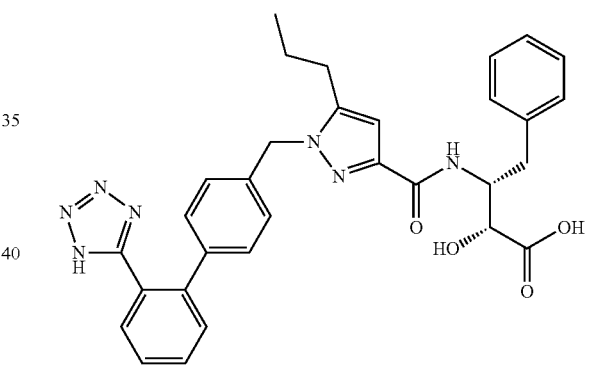

A solution of 5-propyl-1-[2'-(1-trityl-1H-tetrazol-5-yl)biphenyl-4-ylmethyl]-1H-pyrazole-3-carboxylic acid (475 mg, 753 mmol), HATU (286.3 mg, 753.1 µmol), DIPEA (787.0 µL, 4518 µmol), and DMF (21.3 mL, 274.7 mmol) was stirred to pre-activate the acid. (2R,3R)-3-Amino-2-hydroxy-4-phenylbutyric acid.HCl (175 mg, 755 µmol) was added and the resulting mixture was heated at 45° C. and stirred overnight. The mixture was concentrated to yield the protected intermediate, (2R,3R)-2-hydroxy-4-phenyl-3-({5-propyl-1-[2'-(1-trityl-1H-tetrazol-5-yl)biphenyl-4-ylmethyl]-1H-pyrazole-3-carbonyl}amino)butyric acid as a residue, which was used directly in the next step. The residue was dissolved in 1,4-dioxane (10 mL, 100 mmol) and 4.0 M of HCl in 1,4-dioxane (10 mL, 40 mmol) was added. The resulting solution was stirred for 90 minutes. The mixture was concentrated, redissolved in water/MeCN/TFA and purified using reverse phase liquid chromatography to yield the title compound (176 mg; 96% purity). MS m/z: [M+H]$^+$ calcd for $C_{31}H_{11}N_7O_4$, 566.24. found 566.6.

Preparation 2

(Tetrazol-5-yl)phenylboronic Acid

[2-(1-Trityltetrazol-5-yl)phenyl]boronic acid (11.5 g, 26.6 mmol) was combined with 1,4-dioxane (41.5 mL, 532.1 mmol) and 4 M of HCl in 1,4-dioxane (13.3 mL, 53.2 mmol). The mixture was stirred for 2 hours. EtOAc (100 mL) was added. 10 M NaOH was added until pH~9, with constant stirring. The organic layer was extracted and discarded. The aqueous layer was acidified to pH~2 with DCM (10 mL). The product crashed out and was filtered and dried to obtain the title compound (3.5 g) as a white solid.

Preparation 3

1-(4-Bromobenzyl)-5-propyl-1H-pyrazole-3-carboxylic Acid Ethyl Ester

Ethyl 3-n-propylpyrazole-5-carboxylate (8.0 g, 43.0 mmol), 4-bromobenzyl bromide (11.0 g, 43.0 mmol) and potassium carbonate (5.9 g, 43.0 mmol) were dissolved in DMF (433 mL, 5590 mmol). The resulting suspension was stirred at room temperature over approximately 48 hours. The material was concentrated, then diluted with aqueous NaHCO$_3$ and diethyl ether. The aqueous layer was further extracted with diethyl ether. The combined organics were dried over MgSO$_4$, filtered and concentrated. The residue was purified using flash chromatography (1$^{st}$ 40:1 hexanes/EtOAc; 2$^{nd}$ 5:1 hexanes/EtOAc). The two isomers were separated and analyzed by NMR and NOE: 1-(4-bromobenzyl)-5-propyl-1H-pyrazole-3-carboxylic acid ethyl ester (5.7 g) and 2-(4-bromobenzyl)-5-propyl-2H-pyrazole-3-carboxylic acid ethyl ester.

Preparation 4

5-Propyl-1-[2'-(1H-tetrazol-5-yl)biphenyl-4-ylmethyl]-1H-pyrazole-3-carboxylic Acid

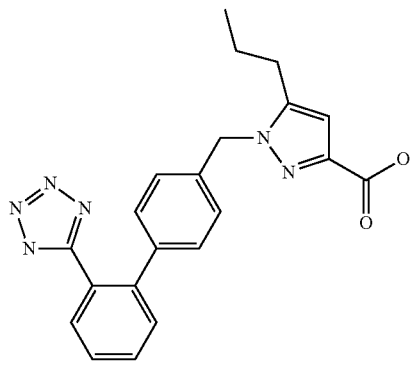 [SMILES: CCCc1cc(C(=O)O)nn1Cc1ccc(-c2ccccc2-c2nnn[nH]2)cc1]

A solution of (tetrazol-5-yl)phenylboronic acid (650 mg, 3.4 mmol), 1-(4-bromobenzyl)-5-propyl-1H-pyrazole-3-carboxylic acid ethyl ester (1.0 g, 2.9 mmol), tetrakis(triphenylphosphine)palladium(0) (200 mg, 0.1 mmol), 1.0 M NaOH in water (9.0 mL, 9.0 mmol) and MeOH (14 mL, 350 mmol) was sparged shortly, capped under nitrogen and heated in the microwave at 90° C. for 2 hours. The mixture was concentrated to remove the MeOH, then extracted with EtOAc. The organic layer was extracted with 1 N NaOH. The combined aqueous layers were acidified with 1 N HCl to pH 3-4 and extracted with EtOAc. The organics were dried over MgSO$_4$, filtered and concentrated. The reaction was repeated twice due to the volume restriction of the microwave reaction vessel, and the residues were combined to yield the title compound (2.2 g), which was used without further purification.

Example 2

(R)-4-Phenyl-3-({5-propyl-1-[2'-(1H-tetrazol-5-yl)-biphenyl-4-ylmethyl]-1H-pyrazole-3-carbonyl}amino)butyric Acid

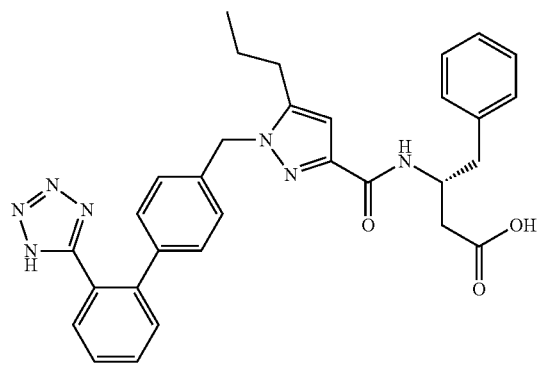 [SMILES: CCCc1cc(C(=O)N[C@@H](CC(=O)O)Cc2ccccc2)nn1Cc1ccc(-c2ccccc2-c2nnn[nH]2)cc1]

A solution of 5-propyl-1-[2'-(1H-tetrazol-5-yl)-biphenyl-4-ylmethyl]-1H-pyrazole-3-carboxylic acid (200 mg, 510 μmol), HOAt (77.1 mg, 566.4 μmol), EDCI (108.6 mg, 566.4 μmol), and 2,6-lutidine (357.8 μL, 3.1 mmol) in DCM (6.1 mL, 94.7 mmol) was stirred to pre-activate the acid. After 30 minutes, the mixture was cooled at 0° C. and (R)-3-amino-4-phenylbutyric acid hydrochloride (122.2 mg, 566.4 μmol) was added. The resulting solution was slowly warmed to room temperature and stirred overnight. The mixture was then concentrated, re-dissolved in water/MeCN/TFA and purified using reverse phase liquid chromatography to yield the title compound (59 mg; 92% purity). MS m/z: [M+H]$^+$ calcd for C$_{31}$H$_{31}$N$_7$O$_3$, 550.25. found 550.4.

Example 3

Following the procedures described in the examples above, and substituting the appropriate starting materials and reagents, compounds 3-1 to 3-38, having the following formula, were prepared:

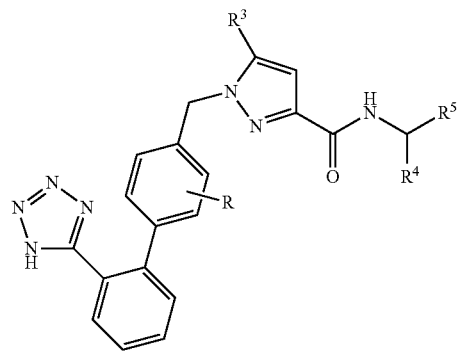

MS m/z: [M + H]+

| # | R | R³ | R⁴ | R⁵ | Formula | calcd | found |
|---|---|---|---|---|---|---|---|
| 1 | 3-F | ethoxy | —CH₂SH | benzyl | C₂₉H₂₈FN₇O₂S | 558.20 | 558.6 |
| 2 | 3-F | propyl | —CH₂SH | benzyl | C₃₀H₃₀FN₇OS | 556.22 | 556.4 |
| 3 | 3-F | propyl | —CH₂SH | i-butyl | C₂₇H₃₂FN₇OS | 522.24 | 522.6 |
| 4 | — | ethoxy | —CH₂SH | benzyl | C₂₉H₂₉N₇O₂S | 540.21 | 540.6 |
| 5 | — | ethoxy | —CH₂SH | i-butyl | C₂₆H₃₁N₇O₂S | 506.23 | 506.4 |
| 6 | — | propyl | —CH₂SH | benzyl | C₃₀H₃₁N₇OS | 538.23 | 538.8 |
| 7 | — | propyl | —CH₂SH | i-butyl | C₂₇H₃₃N₇OS | 504.25 | 504.6 |
| 8 | 3-F | ethoxy | —CH(OH)—COOH | benzyl | C₃₀H₂₈FN₇O₅ | 586.21 | 586.4 |
| 9 | — | ethoxy | —CH(OH)—COOH | benzyl | C₃₀H₂₉N₇O₅ | 568.22 | 568.4 |
| 10 | 2-F | propyl | —CH(OH)—COOH | benzyl | C₃₁H₃₀FN₇O₄ | 584.23 | 584.4 |
| 11 | 2-F | propyl | —CH₂SH | benzyl | C₃₀H₃₀FN₇OS | 556.22 | 556.4 |
| 12 | — | propyl | —CH(OH)—C(O)OCH₃ | benzyl | C₃₂H₃₃N₇O₄ | 580.26 | 580.4 |
| 13 | — | propyl | —CH₂COOH | 2-Br-benzyl | C₃₁H₃₀BrN₇O₃ | 628.16 | 628.4 |
| 14 | — | propyl | —CH₂—N(OH)—C(O)H | benzyl | C₃₁H₃₂N₈O₃ | 565.26 | 565.4 |
| 15 | — | propyl | —CH₂—C(O)NH(OH) | 2-Cl-benzyl | C₃₁H₃₁ClN₈O₃ | 599.22 | 599.6 |
| 16 | — | propyl | —CH₂—C(O)NH(OH) | benzyl | C₃₁H₃₂N₈O₃ | 565.26 | 565.6 |
| 17 | — | propyl | —CH(OH)—C(O)NH(OH) | benzyl | C₃₁H₃₂N₈O₄ | 581.25 | 581.4 |
| 18 | 2-F | propyl | —CH₂COOH | 2-Cl-benzyl | C₃₁H₂₉ClFN₇O₃ | 602.20 | 602.6 |
| 19 | 2-F | propyl | —CH₂COOH | 2-CF₃-benzyl | C₃₂H₂₉F₄N₇O₃ | 636.23 | 636.4 |
| 20 | 3-F | propyl | —CH₂COOH | 2-Cl-benzyl | C₃₁H₂₉ClFN₇O₃ | 602.20 | 602.6 |
| 21 | 3-F | propyl | —CH₂COOH | 2-CF₃-benzyl | C₃₂H₂₉F₄N₇O₃ | 636.23 | 636.2 |
| 22 | — | propyl | —CH(OH)—COOH | 2-Cl-benzyl | C₃₁H₃₀ClN₇O₄ | 600.21 | 600.4 |
| 23 | 3-F | propyl | —CH(OH)—COOH | benzyl | C₃₁H₃₀FN₇O₄ | 584.23 | 584.4 |
| 24 | 2-F | propyl | —CH(OH)—COOH | benzyl | C₃₁H₃₀FN₇O₄ | 584.23 | 584.4 |
| 25 | — | propyl | —CH₂—N(OH)—C(O)H | benzyl | C₂₈H₃₄N₈O₃ | 531.28 | 531.6 |
| 26 | 3,5-diF | propyl | —CH(OH)—COOH | benzyl | C₃₁H₂₉F₂N₇O₄ | 602.23 | 602.6 |
| 27 | — | propyl | —CH₂—C(O)OCH₃ | benzyl | C₃₂H₃₃N₇O₃ | 564.26 | 564.6 |
| 28 | — | propyl | —CH₂—C(O)OCH₃ | 2-Cl-benzyl | C₃₂H₃₂ClN₇O₃ | 598.23 | 598.4 |
| 29 | — | propyl | —CH₂—C(O)OCH₃ | 2-CH₃-benzyl | C₃₃H₃₅N₇O₃ | 578.28 | 578.6 |
| 30 | 3-F | propyl | —CH₂—COOH | benzyl | C₃₁H₃₀FN₇O₃ | 568.24 | 568.6 |
| 31 | 3-F | ethoxy | —CH₂—COOH | benzyl | C₃₀H₂₈FN₇O₄ | 570.22 | 570.6 |
| 32 | — | ethoxy | —CH₂—COOH | benzyl | C₃₀H₂₉N₇O₄ | 552.23 | 552.4 |
| 33 | — | propyl | —CH₂COOH | 2-F-benzyl | C₃₁H₃₀FN₇O₃ | 568.24 | 568.2 |
| 34 | — | propyl | —CH₂COOH | 2-Cl-benzyl | C₃₁H₃₀ClN₇O₃ | 584.21 | 584.2 |
| 35 | — | propyl | —CH₂COOH | 2-CH₃-benzyl | C₃₂H₃₃N₇O₃ | 564.26 | 564.6 |
| 36 | — | propyl | —CH₂COOH | 2-CF₃-benzyl | C₃₂H₃₀F₃N₇O₃ | 618.24 | 618.6 |
| 37 | 3-F | ethyl | —CH(OH)—COOH | benzyl | C₃₀H₂₈FN₇O₄ | 570.22 | 570.2 |
| 38 | 3-F | ethoxy | —CH₂SH | i-butyl | C₂₆H₃₀FN₇O₂S | 524.22 | 524.4 |

1. 5-Ethoxy-1-[3-fluoro-2'-(1H-tetrazol-5-yl)biphenyl-4-ylmethyl]-1H-pyrazole-3-carboxylic acid ((R)-1-benzyl-2-mercaptoethyl)amide
2. 1-[3-Fluoro-2'-(1H-tetrazol-5-yl)biphenyl-4-ylmethyl]-5-propyl-1H-pyrazole-3-carboxylic acid ((R)-1-benzyl-2-mercaptoethyl)amide
3. 1-[3-Fluoro-2'-(1H-tetrazol-5-yl)biphenyl-4-ylmethyl]-5-propyl-1H-pyrazole-3-carboxylic acid ((R)-1-mercaptomethyl-3-methylbutyl)amide
4. 5-Ethoxy-1-[2'-(1H-tetrazol-5-yl)biphenyl-4-ylmethyl]-1H-pyrazole-3-carboxylic acid ((R)-1-benzyl-2-mercaptoethyl)amide
5. 5-Ethoxy-1-[2'-(1H-tetrazol-5-yl)biphenyl-4-ylmethyl]-1H-pyrazole-3-carboxylic acid ((R)-1-mercaptomethyl-3-methylbutyl)amide
6. 5-Propyl-1-[2'-(1H-tetrazol-5-yl)biphenyl-4-ylmethyl]-1H-pyrazole-3-carboxylic acid (((R)-1-benzyl-2-mercaptoethyl)amide
7. 5-Propyl-1-[2'-(1H-tetrazol-5-yl)biphenyl-4-ylmethyl]-1H-pyrazole-3-carboxylic acid (((R)-1-mercaptomethyl-3-methylbutryl)amide
8. (2R,3R)-3-({5-Ethoxy-1-[3-fluoro-2'-(1H-tetrazol-5-yl)biphenyl-4-ylmethyl]-1H-pyrazole-3-carbonyl}amino)-2-hydroxy-4-phenylbutyric acid
9. (2R,3R)-3-({5-Ethoxy-1-[2'-(1H-tetrazol-5-yl)biphenyl-4-ylmethyl]-1H-pyrazole-3-carbonyl}amino)-2-hydroxy-4-phenylbutyric acid
10. (2R,3R)-3-(1-((2-Fluoro-2'-(1H-tetrazol-5-yl)biphenyl-4-yl)methyl)-5-propyl-1H-pyrazole-3-carboxamido)-2-hydroxy-4-phenylbutanoic acid -continued

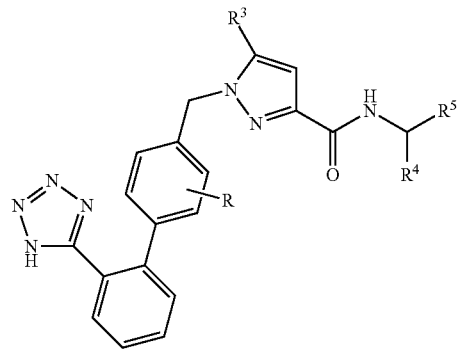

| | | | | | | MS m/z: [M + H]⁺ | |
|---|---|---|---|---|---|---|---|
| # | R | R³ | R⁴ | R⁵ | Formula | calcd | found |

11. (1-((2-Fluoro-2'-(1H-tetrazol-5-yl)biphenyl-4-yl)methyl)-N-((R)-1-mercapto-3-phenylpropan-2-yl)-5-propyl-1H-pyrazole-3-carboxamide
12. (2R,3R)-2-Hydroxy-4-phenyl-3-({5-propyl-1-[2'-(1H-tetrazol-5-yl)-biphenyl-4-ylmethyl]-1H-pyrazole-3-carbonyl}amino)butyric acid methyl ester
13. (R)-4-(2-Bromophenyl)-3-({5-propyl-1-[2'-(1H-tetrazol-5-yl)-biphenyl-4-ylmethyl]-1H-pyrazole-3-carbonyl}amino)butyric acid
14. 5-Propyl-1-[2'-(1H-tetrazol-5-yl)-biphenyl-4-ylmethyl]-1H-pyrazole-3-carboxylic acid [(R)-1-benzyl-2-(formylhydroxyamino)ethyl]amide
15. 5-Propyl-1-[2'-(1H-tetrazol-5-yl)-biphenyl-4-ylmethyl]-1H-pyrazole-3-carboxylic acid [(R)-1-(2-chlorophenyl)-1-hydroxycarbamoylmethylethyl]amide
16. 5-Propyl-1-[2'-(1H-tetrazol-5-yl)-biphenyl-4-ylmethyl]-1H-pyrazole-3-carboxylic acid ((R)-1-hydroxycarbamoylmethyl-2-phenylethyl)amide
17. 1-((2'-(1H-tetrazol-5-yl)biphen;yl-4-yl)methyl)-N-((2R,3R)-3-hydroxy-4-(hydroxyamino)-4-oxo-1-phenylbutan-2-yl)-5-propyl-1H-pyrazole-3-carboxamide
18. (R)-4-(2-Chlorophenyl)-3({1-[2-fluoro-2'-(1H-tetrazol-5-yl)biphenyl-4-ylmethyl]-5-propyl-1H-pyrazole-3-carbonyl}amino)butyric acid
19. (R)-3-({1-[2-Fluoro-2'-(1H-tetrazol-5-yl)-biphenyl-4-ylmethyl]-5-propyl-1H-pyrazole-3-carbonyl}amino)-4-(2-trifluoromethylphenyl)butyric acid
20. (R)-4-(2-chlorophenyl)-3-(1-((3-fluoro-2'-(1H-tetrazol-5-yl)biphenyl-4-yl)methyl)-5-propyl-1H-pyrazole-3-carboxamido)butanoic acid
21. (R)-3-(1-((3-fluoro-2'-(1H-tetrazol-5-yl)biphenyl-4-yl)methyl)-5-propyl-1H-pyrazole-3-carboxamido)-4-(2-(trifluoromethyl)phenyl)butanoic acid
22. (2R,3R)-3-(1-((2'-(1H-tetrazol-5-yl)biphenyl-4-yl)methyl-5-propyl-1H-pyrazole-3-carboxamido)-4-(2-chlorophenyl)-2-hydroxybutanoic acid
23. (2R,3R)-3-(1-((3-fluoro-2'-(1H-tetrazol-5-yl)biphenyl-4-yl)methyl)-5-propyl-1H-pyrazole-3-carboxamido)-2-hydroxy-4-phenylbutanoic acid
24. (2R,3R)-3-(1-((2-fluoro-2'-(1H-tetrazol-5-yl)biphenyl-4-yl)methyl)-5-propyl-1H-pyrazole-3-carboxamido)-2-hydroxy-4-phenylbutanoic acid
25. 5-Propyl-1-[2'-(1H-tetrazol-5-yl)-biphenyl-4-ylmethyl]-1H-pyrazole-3-carboxylic acid {(R)-1-[(formylhydroxyamino)methyl]-3-methylbutyl}amide
26. (2R,3R)-3-(1-((3,5-difluoro-2'-(1H-tetrazol-5-yl)biphenyl-4-yl)methyl)-5-propyl-1H-pyrazole-3-carboxamido)-2-hydroxy-4-phenylbutanoic acid
27. (R)-4-Phenyl-3-({5-propyl-1-[2'-(1H-tetrazol-5-yl)-biphenyl-4-ylmethyl]-1H-pyrazole-3-carbonyl}amino)butyric acid methyl ester
28. (R)-4-(2-Chlorophenyl)-3-({5-propyl-1-[2'-(1H-tetrazol-5-yl)-biphenyl-4-ylmethyl]-1H-pyrazole-3-carbonyl}amino)butyric acid methyl ester
29. (R)-3-({5-Propyl-1-[2'-(1H-tetrazol-5-yl)-biphenyl-4-ylmethyl]-1H-pyrazole-3-carbonyl}amino)-4-o-tolyl-butyric acid methyl ester
30. (R)-3-({1-[3-Fluoro-2'-(1H-tetrazol-5-yl)biphenyl-4-ylmethyl]-5-propyl-1H-pyrazole-3-carbonyl}amino)-4-phenylbutyric acid
31. (R)-3-({5-Ethoxy-1-[3-fluoro-2'-(1H-tetrazol-5-yl)biphenyl-4-ylmethyl]-1H-pyrazole-3-carbonyl}amino)-4-phenylbutyric acid
32. (R)-3-({5-Ethoxy-1-[2'-(1H-tetrazol-5-yl)-biphenyl-4-ylmethyl]-1H-pyrazole-3-carbonyl}amino)-4-phenylbutyric acid
33. (R)-4-(2-Fluorophenyl)-3-({5-propyl-1-[2'-(1H-tetrazol-5-yl)-biphenyl-4-ylmethyl]-1H-pyrazole-3-carbonyl}amino)butyric acid
34. (R)-4-(2-Chlorophenyl)-3-({5-propyl-1-[2'-(1H-tetrazol-5-yl)-biphenyl-4-ylmethyl]-1H-pyrazole-3-carbonyl}amino)butyric acid
35. (R)-3-({5-Propyl-1-[2'-(1H-tetrazol-5-yl)-biphenyl-4-ylmethyl]-1H-pyrazole-3-carbonyl}amino)-4-o-tolylbutyric acid
36. (R)-3-({5-Propyl-1-[2'-(1H-tetrazol-5-yl)-biphenyl-4-ylmethyl]-1H-pyrazole-3-carbonyl}amino)-4-(2-trifluoromethylphenyl)butyric acid
37. (2R,3R)-3-({5-Ethyl-1-[3-fluoro-2'-(1H-tetrazol-5-yl)-biphenyl-4-ylmethyl]-1H-pyrazole-3-carbonyl}amino)-2-hydroxy-4-phenylbutyric acid
38. 5-Ethoxy-1-[3-fluoro-2'-(1H-tetrazol-5-yl)biphenyl-4-ylmethyl]-1H-pyrazole-3-carboxylic acid ((R)-1-mercaptomethyl-3-methylbutyl)amide

Preparation 5

2-Bromo-N-[1-dimethylaminometh-(E)-ylidene]benzenesulfonamide 1,1-Dimethoxy-N,N-dimethylmethanamine (14.6 mL, 104 mmol) was added to a solution of 2-bromobenzene-1-sulfonamide (20.4 g, 86.4 mmol) in DMF (56 mL, 720 mmol) and the resulting solution was stirred at room temperature for 90 minutes. A solution of sodium hydrogen sulfate (1.7 g, 14 mmol) in water (170 mL, 9.4 mol) was cooled at 0° C. and then added to the reaction mixture. The precipitate was filtered, washed with water, and dried to yield the title compound (24.3 g) as a white solid.

Preparation 6

4'-Methylbiphenyl-2-sulfonic acid 1-dimethylaminometh-(E)-ylideneamide

2-Bromo-N-[1-dimethylaminometh-(E)-ylidene]-benzenesulfonamide (5.4 g, 18.4 mmol), 4-methylphenylboronic acid (5.0 g, 36.8 mmol) and potassium carbonate (5.1 g, 36.8 mmol) were dissolved in water (19.7 mL, 1090 mmol), EtOH (49.2 mL, 842 mmol) and toluene (98.3 mL, 923 mmol). The resulting mixture was stirred under nitrogen. Tetrakis(triphenylphosphine)palladium(0) (1.4 g, 1.2 mmol) was added. The mixture was heated at 60° C. for 115 minutes, at 70° C. for 30 minutes, then cooled to room temperature. Water (100 mL) and EtOAc (100 mL) were added. The mixture was washed with saturated aqueous NaCl, extracted with EtOAc, dried over MgSO$_4$, filtered, and concentrated to yield a red solid. The product was triturated with 1:1 EtOAc:hexanes, filtered, and rinsed with hexanes to yield a reddish-brown solid. The product was triturated with EtOAc, filtered, and rinsing with EtOAc to yield the title compound (4.6 g) as a light brown solid.

Preparation 7

4'-bromomethylbiphenyl-2-sulfonic acid 1-dimethylaminometh-(E)-ylideneamide

4'-Methylbiphenyl-2-sulfonic acid 1-dimethylaminometh-(E)-ylideneamide (540.0 mg, 1786 μmol), NBS (318 mg, 1.8 mmol), and benzoyl peroxide (4.3 mg, 17.8 μmol) were dissolved in chlorobenzene (7.0 mL, 69 mmol) and the resulting solution was heated at 100° C. for 90 minutes. The mixture was cooled to room temperature and water was added. The mixture was extracted with DCM, washed with saturated NaHCO$_3$ and saturated aqueous NaCl, extracted again with DCM, dried over MgSO4, filtered, and concentrated. The crude product was purified by flash chromatography (40 g, 0-100% EtOAc in hexanes), then taken up in EtOAc (4.5 mL) and DCM (1.5 mL). Additional DCM (3.0 mL) was added and the mixture was heated at 60° C. The mixture was cooled in the freezer overnight, then concentrated. The material was taken up in DCM (2 mL), EtOAc (6 mL) was added, and the resulting solution placed in the freezer. A precipitate formed and was filtered to yield the title compound (279 mg) as a white solid.

Preparation 8

1-(2'-Acetylsulfamoyl-biphenyl-4-ylmethyl)-5-propyl-1H-pyrazole-3-carboxylic acid

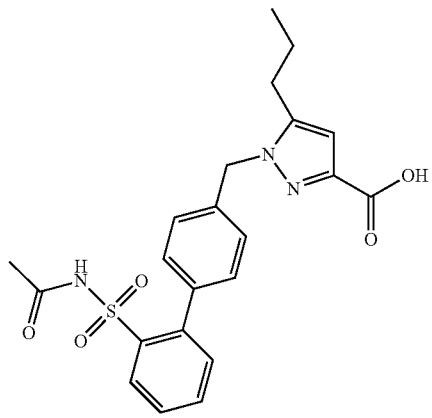 [SMILES: CCCc1cc(C(=O)O)nn1Cc1ccc(-c2ccccc2S(=O)(=O)NC(C)=O)cc1]

Ethyl 3-n-propylpyrazole-5-carboxylate (1.3 g, 7.2 mmol), 4'-bromomethyl biphenyl-2-sulfonic acid 1-dimethylaminometh-(E)-ylideneamide (6.2 g, 7.2 mmol) and potassium carbonate (2.0 g, 14.3 mmol) were dissolved in DMF (50 mL, 700 mmol) and the resulting mixture was stirred at room temperature until the reaction was nearly complete (1:1 mixture of regioisomers). The mixture was partially concentrated, then partitioned between water and EtOAc. The EtOAc layer was then washed with saturated aqueous NaCl, dried over Na$_2$SO$_4$ and concentrated. The crude product was purified by flash chromatography (0-50% EtOAc/hexanes, dry load) to yield 1-(2'-{[1-dimethyl-aminometh-(E)-ylidene]sulfamoyl}biphenyl-4-ylmethyl)-5-propyl-1H-pyrazole-3-carboxylic acid ethyl ester (1.2 g).

To a solution of 1-(2'-{[1-dimethylaminometh-(E)-ylidene]sulfamoyl}biphenyl-4-ylmethyl)-5-propyl-1H-pyrazole-3-carboxylic acid ethyl ester (1.2 g, 2.5 mmol) in isopropyl alcohol (15.0 mL, 196 mmol) was added 12 M of HCl in water (3.9 mL, 46.6 mmol), and the resulting solution was heated to reflux for 5 hours. The mixture was cooled to room temperature and stirred overnight. The solution was adjusted to a pH of 5 using 1 N NaOH. The resulting suspension was filtered. The filtrate was concentrated to remove the isopropyl alcohol and the aqueous layer was extracted with EtOAc and DCM. The combined extracts were dried over MgSO$_4$, filtered and concentrated.

The residue (890 mg) was dissolved in methylene chloride (13.1 mL, 204 mmol). DIPEA (5.2 mL, 29.8 mmol) and acetic anhydride (2.4 mL, 24.9 mmol) was added and the resulting solution was stirred overnight. The mixture was concentrated and the residue was diluted with t-butyl alcohol (30 mL, 300 mmol). 0.20 M LiOH in water (60 mL, 10 mmol) was added and the mixture was stirred overnight. The mixture was concentrated and then extracted with EtOAc. The EtOAc was back-extracted with 1 N LiOH. The combined aqueous layers were acidified with 1 N HCl to pH 4-5. The acidic aqueous layer was extracted with EtOAc and DCM to yield the title compound (1.0 g).

Example 4

(2R,3R)-3-(1-((2'-(N-Acetylsulfamoyl)biphenyl-4-yl)methyl)-5-propyl-1H-pyrazole-3-carboxamido)-2-hydroxy-4-phenylbutanoic Acid

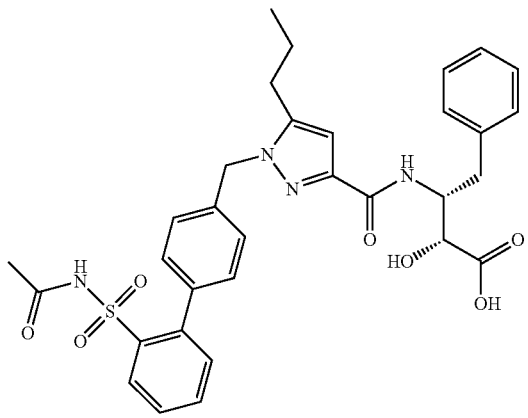 [SMILES: CCCc1cc(C(=O)N[C@H](Cc2ccccc2)[C@@H](O)C(=O)O)nn1Cc1ccc(-c2ccccc2S(=O)(=O)NC(C)=O)cc1]

A solution of 1-(2'-acetylsulfamoylbiphenyl-4-ylmethyl)-5-propyl-1H-pyrazole-3-carboxylic acid (250 mg, 570 μmol), HATU (215 mg, 566 μmol) and DIPEA (592 μL, 3.4 mmol) in DMF (18 mL, 230 mmol) was stirred to pre-activate the acid. After 15 minutes, (2R,3R)-3-amino-2-hydroxy-4-phenylbutyric acid (110 mg, 566 μmol) was added. The resulting solution was stirred at 45° C. overnight. The mixture was concentrated, re-dissolved in water/MeCN/TFA and purified using reverse phase liquid chromatography to yield the title compound (197 mg, 97% purity). MS m/z: [M+H]+ calcd for $C_{32}H_{34}N_4O_7S$, 619.22. found 619.6.

Preparation 9

N-t-Butyl-2-(4,4,5,5-tetramethyl-1,3,2-dioxaborolan-2-yl)benzenesulfonamide

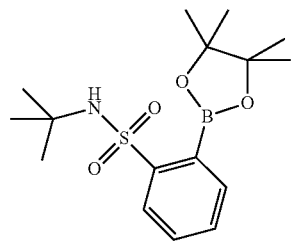 [SMILES: CC(C)(C)NS(=O)(=O)c1ccccc1B1OC(C)(C)C(C)(C)O1]

2-Bromobenzenesulfonyl chloride (100.9 g, 394.9 mmol) was dissolved in methylene chloride (500 mL, 8.0 mol) and cooled at 0° C. t-Butylamine (41.3 mL, 395 mmol) was added in 3 portions over approximately 1 minute. DIPEA (75.7 mL, 434 mmol) was immediately added in 3 portions over approximately 1 minute. The mixture was warmed to room temperature and stirred overnight. The product was washed with 1M $H_3PO_4$ (2×), with saturated. NaHCO$_3$, and with saturated aqueous NaCl, then dried over MgSO4, filtered, and concentrated to yield 2-bromo-N-t-butyl-benzenesulfonamide (112 g) as a light brown solid.

2-Bromo-N-t-butyl-benzenesulfonamide (10.0 g, 34.2 mmol) was mixed with palladium acetate (0.768 g, 3.42 mmol). Potassium acetate (13.4 g, 137 mmol) was added followed by bis(pinacolato)diboron (10.4 g, 41.1 mmol) then DMF (265 mL, 3420 mmol). The resulting mixture was stirred under nitrogen, heated to reflux for 2 hours, then heated at 70° C. for 48 hours. The mixture was poured onto ice, partitioned with EtOAc (200 mL), the organics were washed with saturated aqueous NaCl, dried over MgSO$_4$, filtered and concentrated. The product was purified by flash chromatography in hexanes:EtOAc 0-75% to yield the title compound (6.3 g).

Preparation 10

5-Propyl-1-(2'-sulfamoylbiphenyl-4-ylmethyl)-1H-pyrazole-3-carboxylic Acid Ethyl Ester 1-(4-Bromobenzyl)-5-propyl-1H-pyrazole-3-carboxylic acid ethyl ester (1.2 g, 3.3 mmol) and N-t-butyl-2-(4,4,5,5-tetramethyl-1,3,2-dioxaborolan-2-yl)benzene sulfonamide (1.4 g, 4.0 mmol) were combined with toluene (70.9 mL, 666.0 mmol) and EtOH (18.5 mL, 316.7 mmol). Potassium carbonate (920 mg, 6.7 mmol) was dissolved in water (9.6 mL, 532.8 mmol) and added to the mixture, and stirred. Tetrakis(triphenyl-phosphine)palladium(0) (385 mg, 333 μmol) was added quickly and the mixture heated at 100° C. for 30 minutes in the microwave. EtOAc and water was added and organics were extracted and evaporated. The crude product was dissolved in neat TFA (20 mL, 300 mmol) and stirred at 50° C. for 1.5 hours. The product was dried under vacuum. DCM (20 mL) and saturated NaHCO$_3$ (20 mL) were added, stirred and extracted, dried, and evaporated to yield the title compound.

Preparation 11

1-((2'-(N-(methoxycarbonyl)sulfamoyl)biphenyl-4-yl)methyl)-5-propyl-1H-pyrazole-3-carboxylic acid

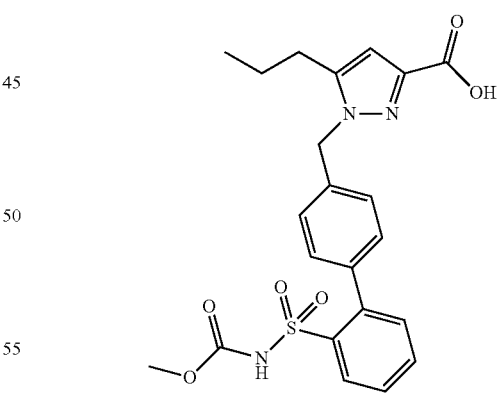

5-Propyl-1-(2'-sulfamoylbiphenyl-4-ylmethyl)-1H-pyrazole-3-carboxylic acid ethyl ester (80 mg, 0.2 mmol) was dissolved in methylene chloride (2.0 mL, 30.6 mmol). Methyl chloroformate (17.4 μL, 224 μmol) was added, along with DIPEA (81.5 μL, 468 μmol). The mixture was stirred at room temperature for 2 hours. 1 M LiOH in water (1.5 mL, 1.50 mmol) and THF:EtOH 2:1 mL were added and the resulting mixture was stirred for 2 hours. The reaction was quenched with 1 N HCl and DCM (4 mL) was added. The organics were extracted and dried under vacuum to yield the title compound.

Example 5

(2R,3R)-2-hydroxy-3-(1-((2'-(N-(methoxycarbonyl)-sulfamoyl)biphenyl-4-yl)methyl)-5-propyl-1H-pyrazole-3-carboxamido)-4-phenylbutanoic Acid

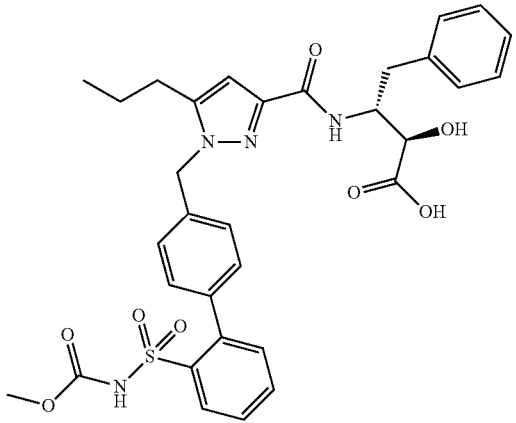 [SMILES: CCCc1cc(C(=O)N[C@H](Cc2ccccc2)[C@@H](O)C(=O)O)nn1Cc1ccc(-c2ccccc2S(=O)(=O)NC(=O)OC)cc1]

A solution of 1-((2'-(N-(methoxycarbonyl)sulfamoyl)biphenyl-4-yl)methyl)-5-propyl-1H-pyrazole-3-carboxylic acid (40.2 mg, 87.8 μmol), DIPEA (91.8 μL, 527 μmol) and HATU (33.4 mg, 87.8 μmol) in DMF (0.4 mL, 4 mmol) was stirred to pre-activate the acid. After 1 minute, (2R,3R)-3-amino-2-hydroxy-4-phenylbutyric acid (17.1 mg, 87.8 μmol) was added, and the mixture was stirred for 10 minutes. The reaction was quenched by adding 1 N HCl and extracted with DCM. The organic layer was added to AcOH (1 mL) and evaporated in vacuo. The material was then purified by preparative HPLC to yield the title compound (10 mg, 95% purity). MS m/z: [M+H]$^+$ calcd for $C_{32}H_{34}N_4O_8S$, 635.21. found 635.20.

Example 6

Following the procedures described in the examples above, and substituting the appropriate starting materials and reagents, compounds 6-1 to 6-28, having the following formula, were prepared:

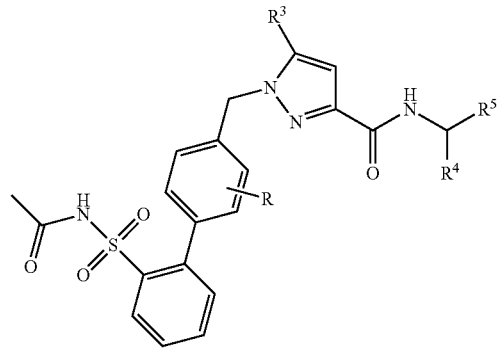

| # | R | $R^3$ | $R^4$ | $R^5$ | Formula | MS m/z: [M + H]$^+$ calcd | found |
|---|---|---|---|---|---|---|---|
| 1 | 3-F | ethoxy | —CH$_2$SH | benzyl | $C_{30}H_{31}FN_4O_5S_2$ | 611.17 | 611.4 |
| 2 | — | ethoxy | —CH$_2$SH | benzyl | $C_{30}H_{32}N_4O_5S_2$ | 593.18 | 593.6 |
| 3 | — | ethoxy | —CH(OH)—COOH | benzyl | $C_{31}H_{32}N_4O_8S$ | 621.19 | 621.6 |
| 4 | 3-F | ethoxy | —CH(OH)—COOH | benzyl | $C_{31}H_{31}FN_4O_8S$ | 639.18 | 639.4 |
| 5 | — | propyl | —CH$_2$SH | benzyl | $C_{31}H_{34}N_4O_4S_2$ | 591.20 | 591.6 |
| 6 | 2-F | propyl | —CH$_2$SH | benzyl | $C_{31}H_{33}FN_4O_4S_2$ | 609.19 | 609.4 |
| 7 | 2-F | propyl | —CH(OH)—COOH | benzyl | $C_{32}H_{33}FN_4O_7S$ | 637.21 | 637.6 |
| 8 | — | propyl | —CH$_2$COOH | 2-Br-benzyl | $C_{32}H_{33}BrN_4O_6S$ | 681.13 | 681.4 |
| 9 | — | propyl | —CH(OH)—COOH | 2-Cl-benzyl | $C_{32}H_{33}ClN_4O_7S$ | 653.18 | 653.6 |
| 10 | 3-F | ethoxy | —CH(OH)—COOH | benzyl | $C_{31}H_{31}FN_4O_7S$ | 623.19 | 623.2 |
| 11 | 3-F | butyl | —CH(OH)—COOH | benzyl | $C_{33}H_{35}FN_4O_7S$ | 651.22 | 651.2 |
| 12 | — | propyl | —CH(OH)—COOH | benzyl | $C_{34}H_{38}N_4O_7S$ | 647.25 | 647.2 |
| 13 | — | propyl | —CH$_2$N(OH)—C(O)H | benzyl | $C_{32}H_{35}N_5O_6S$ | 618.23 | 618.4 |
| 14 | 3-F | propyl | —CH(OH)—COOH | benzyl | $C_{32}H_{33}FN_4O_7S$ | 637.21 | 637.4 |
| 15 | — | propyl | —CH$_2$N(OH)—C(O)H | i-butyl | $C_{29}H_{37}N_5O_6S$ | 584.25 | 584.4 |
| 16 | 3-F | propyl | —CH$_2$C(O)—NH(OH) | benzyl | $C_{32}H_{34}FN_5O_6S$ | 636.22 | 636.2 |
| 17 | 2-F | propyl | —CH$_2$C(O)—NH(OH) | benzyl | $C_{32}H_{34}FN_5O_6S$ | 636.22 | 636.2 |
| 18 | — | propyl | —CH$_2$C(O)—NH(OH) | benzyl | $C_{32}H_{35}N_5O_6S$ | 618.23 | 618.6 |
| 19 | 3,5-diF | propyl | —CH(OH)—COOH | benzyl | $C_{32}H_{32}F_2N_4O_7S$ | 655.20 | 655.2 |
| 20 | 3,5-diF | propyl | —CH$_2$C(O)—NH(OH) | benzyl | $C_{32}H_{33}F_2N_5O_6S$ | 654.21 | 654.6 |
| 21 | 2-F | propyl | —CH$_2$—C(O)NH(OH) | i-butyl | $C_{29}H_{36}FN_5O_6S$ | 602.24 | 602.6 |
| 22 | — | propyl | —CH$_2$N(OH)—C(O)H | benzyl | $C_{32}H_{35}N_5O_6S$ | 618.23 | 618.6 |
| 23 | — | propyl | —CH$_2$N(OH)—C(O)H | i-butyl | $C_{29}H_{37}N_5O_6S$ | 584.25 | 584.6 |
| 24 | 3-F | ethoxy | —CH$_2$COOH | benzyl | $C_{31}H_{31}FN_4O_7S$ | 623.19 | 623.6 |

-continued

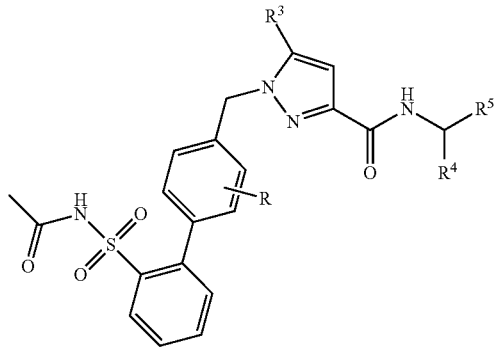

| # | R | R³ | R⁴ | R⁵ | Formula | MS m/z: [M + H]⁺ calcd | found |
|---|---|---|---|---|---|---|---|
| 25 | — | propyl | —CH$_2$COOH | 2-CF$_3$-benzyl | C$_{33}$H$_{33}$F$_3$N$_4$O$_6$S | 671.21 | 671.4 |
| 26 | — | propyl | —CH$_2$COOH | 2-CH$_3$-benzyl | C$_{33}$H$_{36}$N$_4$O$_6$S | 617.24 | 617.6 |
| 27 | — | propyl | —CH$_2$COOH | 2-Cl-benzyl | C$_{32}$H$_{33}$ClN$_4$O$_6$S | 637.18 | 637.4 |
| 28 | — | propyl | —CH$_2$COOH | benzyl | C$_{32}$H$_{34}$N$_4$O$_6$S | 603.22 | 603.6 |

1. 1-(2'-Acetylsulfamoyl-3-fluorobiphenyl-4-ylmethyl)-5-ethoxy-1H-pyrazole-3-carboxylic acid ((R)-1-benzyl-2-mercaptoethyl)amide
2. 1-(2'-Acetylsulfamoyl-biphenyl-4-ylmethyl)-5-ethoxy-1H-pyrazole-3-carboxylic acid ((R)-1-benzyl-2-mercaptoethyl)amide
3. (2R,3R)-3-{[1-(2'-Acetylsulfamoylbiphenyl-4-ylmethyl)-5-ethoxy-1H-pyrazole-3-carbonyl]amino}-2-hydroxy-4-phenyl-butyric acid
4. (2R,3R)-3-{[1-(2'-Acetylsulfamoyl-3-fluorobiphenyl-4-ylmethyl)-5-ethoxy-1H-pyrazole-3-carbonyl]amino}-2-hydroxy-4-phenylbutyric acid
5. 1-(2'-Acetylsulfamoylbiphenyl-4-ylmethyl)-5-propyl-1H-pyrazole-3-carboxylic acid ((R)-1-benzyl-2-mercaptoethyl)amide
6. 1-(2'-Acetylsulfamoyl-2-fluorobiphenyl-4-ylmethyl)-5-propyl-1H-pyrazole-3-carboxylic acid ((R)-1-benzyl-2-mercaptoethyl)amide
7. (2R,3R)-3-{[1-(2'-Acetylsulfamoyl-3-fluorobiphenyl-4-ylmethyl)-5-propyl-1H-pyrazole-3-carbonyl]amino}-2-hydroxy-4-phenylbutyric acid
8. (R)-3-{[1-(2'-Acetylsulfamoylbiphenyl-4-ylmethyl)-5-propyl-1H-pyrazole-3-carbonyl]amino}-4-(2-bromophenyl)butyric acid
9. (2R,3R)-3-{[1-(2'-Acetylsulfamoylbiphenyl-4-ylmethyl)-5-propyl-1H-pyrazole-3-carbonyl]amino}-4-(2-chlorophenyl)-2-hydroxy-butyric acid
10. (2R,3R)-3-{[1-(2'-Acetylsulfamoyl-3-fluoro-biphenyl-4-ylmethyl)-5-ethyl-1H-pyrazole-3-carbonyl]amino}-2-hydroxy-4-phenylbutyric acid
11. (2R,3R)-3-{[1-(2'-Acetylsulfamoyl-3-fluorobiphenyl-4-ylmethyl)-5-butyl-1H-pyrazole-3-carbonyl]amino}-2-hydroxy-4-phenylbutyric acid
12. (2R,3R)-2-Hydroxy-3-{[1-(2'-isobutyrylsulfamoylbiphenyl-4-ylmethyl)-5-propyl-1H-pyrazole-3-carbonyl]amino}-4-phenylbutyric acid
13. 1-(2'-Acetylsulfamoyl-biphenyl-4-ylmethyl)-5-propyl-1H-pyrazole-3-carboxylic acid [(R)-1-benzyl-2-(formyl-hydroxy-amino)-ethyl]amide
14. (2R,3R)-3-(1-((2'-(N-acetylsulfamoyl)-3-fluorobiphenyl-4-yl)methyl-5-propyl-1H-pyrazole-3-carboxamido)-2-hydroxy-4-phenylbutanoic acid
15. 1-(2'-Acetylsulfamoyl-biphenyl-4-ylmethyl)-5-propyl-1H-pyrazole-3-carboxylic acid {(R)-1-[(formyl-hydroxy-amino)-methyl]-3-methylbutyl}amide
16. 1-(2'-Acetylsulfamoyl-3-fluorobiphenyl-4-ylmethyl)-5-propyl1H-pyrazole-3-carboxylic acid ((R)-1-hydroxycarbamoylmethyl-2-phenylethyl)amide
17. 1-(2'-Acetylsulfamoyl-2-fluorobiphenyl-4-ylmethyl)-5-propyl-1H-pyrazole-3-carboxylic acid ((R)-1-hydroxycarbamoylmethyl-2-phenylethyl)amide
18. 1-(2'-Acetylsulfamoylbiphenyl-4-ylmethyl)-5-propyl-1H-pyrazole-3-carboxylic acid ((R)-1-benzyl-2-hydroxycarbamoylethyl)amide
19. (2R,3R)-3-(1-((2'-(N-acetylsulfamoyl)-3,5-difluorobiphenyl-4-yl)methyl)-5-propyl-1H-pyrazole-3-carboxamido)-2-hydroxy-4-phenylbutanoic acid
20. 1-(2'-Acetylsulfamoyl-3,5-difluorobiphenyl-4-ylmethyl)-5-propyl-1H-pyrazole-3-carboxylic acid ((R)-1-hydroxycarbamoylmethyl-2-phenylethyl)amide
21. 1-(2'-Acetylsulfamoyl-2-fluorobiphenyl-4-ylmethyl)-5-propyl-1H-pyrazole-3-carboxylic acid (1-hydroxycarbamoylmethyl-3-methylbutyl)amide
23. 1-(2'-Acetylsulfamoylbiphenyl-1-ylmethyl)-5-propyl-1H-pyrazole-3-carboxylic acid [(S)-1-benzyl-2-(formylhydroxyamino)ethyl]amide
23. 1-(2'-Acetylsulfamoyl-biphenyl-4-ylmethyl)-5-propyl-1H-pyrazole-3-carboxylic acid {(S)-1-[(formylhydroxyamino)methyl]-3-methylbutyl}amide
24. (R)-3-{[1-(2'-Acetylsulfamoyl-3-fluorobiphenyl-4-ylmethyl)-5-ethoxy-1H-pyrazole-3-carbonyl]amino}-4-phenylbutyric acid
25. (R)-3-{[1-(2'-Acetylsulfamoylbiphenyl-4-ylmethyl)-5-propyl-1H-pyrazole-3-carbonyl]amino}-4-(2-trifluoromethylphenyl)butyric acid -continued

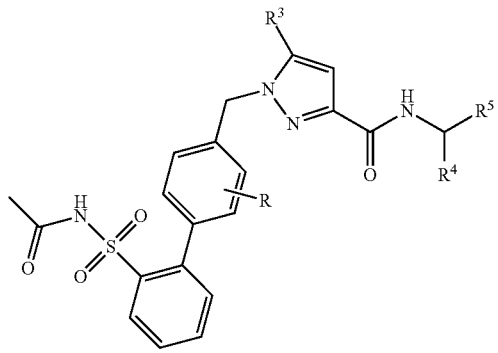

| # | R | $R^3$ | $R^4$ | $R^5$ | Formula | MS m/z: [M + H]⁺ calcd | found |
|---|---|-------|-------|-------|---------|------------------------|-------|

26. (R)-3-{[1-(2'-Acetylsulfamoylbiphenyl-4-ylmethyl)-5-propyl-1H-pyrazole-3-carbonyl]amino}-4-o-tolylbutyric acid
27. (R)-3-{[1-(2'-Acetylsulfamoylbiphenyl-4-ylmethyl)-5-propyl-1H-pyrazole-3-carbonyl]amino}-4-(2-chlorophenyl)butyric acid
28. (R)-3-{[1-(2'-Acetylsulfamoylbiphenyl-4-ylmethyl)-5-propyl-1H-pyrazole-3-carbonyl]amino}-4-phenylbutyric acid

Example 7

Following the procedures described in the examples above, and substituting the appropriate starting materials and reagents, compounds 7-1 to 7-22, having the following formula, were prepared:

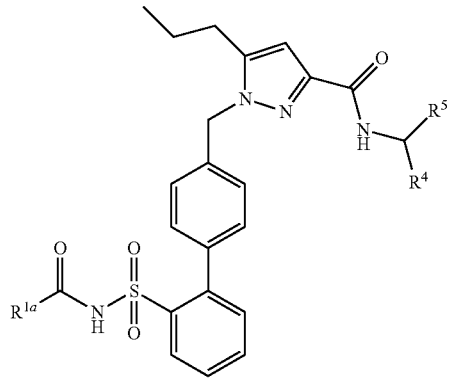

| # | $R^{1a}$ | $R^4$ | $R^5$ | Formula | MS m/z: [M + H]⁺ calcd | found |
|---|----------|-------|-------|---------|-------|-------|
| 1 | —NH(CH₂CH₃) | —CH(OH)—COOH | benzyl | $C_{33}H_{37}N_5O_7S$ | 648.24 | 648.2 |
| 2 | cyclopropyl | —CH(OH)—COOH | benzyl | $C_{34}H_{36}N_4O_7S$ | 645.23 | 645.2 |
| 3 | 2F-phenyl | —CH(OH)—COOH | benzyl | $C_{37}H_{35}FN_4O_7S$ | 699.22 | 699.2 |
| 4 | 4-pyridyl | —CH(OH)—COOH | benzyl | $C_{36}H_{35}N_5O_7S$ | 682.23 | 682.2 |
| 5 | -3-isoxazolyl-5-methyl | —CH(OH)—COOH | benzyl | $C_{35}H_{35}N_5O_8S$ | 686.22 | 686.2 |
| 6 | -5-isoxazolyl | —CH(OH)—COOH | benzyl | $C_{34}H_{33}N_5O_8S$ | 672.21 | 672.2 |
| 7 | —OCH₂CH₃ | —CH(OH)—COOH | benzyl | $C_{33}H_{36}N_4O_8S$ | 649.23 | 649.2 |
| 8 | —CH₂OCH₃ | —CH(OH)—COOH | benzyl | $C_{33}H_{36}N_4O_8S$ | 649.23 | 649.2 |
| 9 | 2-pyridyl | —CH(OH)—COOH | benzyl | $C_{36}H_{35}N_5O_7S$ | 682.23 | 682.2 |
| 10 | ethyl | —CH(OH)—COOH | benzyl | $C_{33}H_{36}N_4O_7S$ | 633.23 | 635.2 |
| 11 | —NH(CH₃) | —CH(OH)—COOH | benzyl | $C_{32}H_{35}N_5O_7S$ | 634.23 | 634.2 |
| 12 | phenyl | —CH(OH)—COOH | benzyl | $C_{37}H_{36}N_4O_7S$ | 681.23 | 681.2 |
| 13 | —CH(CH₃)OH | —CH(OH)—COOH | benzyl | $C_{33}H_{36}N_4O_8S$ | 649.23 | 649.2 |
| 14 | —C(CH₃)₂OH | —CH(OH)—COOH | benzyl | $C_{34}H_{38}N_4O_8S$ | 663.24 | 663.2 |
| 15 | —CH₂OH | —CH(OH)—COOH | benzyl | $C_{32}H_{34}N_4O_8S$ | 635.21 | 635.2 |
| 16 | —CH(CH₃)OH | —CH(OH)—COOH | benzyl | $C_{33}H_{36}N_4O_8S$ | 649.23 | 649.2 |
| 17 | —(CH₂)₂—OCH₃ | —CH(OH)—COOH | benzyl | $C_{34}H_{38}N_4O_8S$ | 663.24 | 663.2 |
| 18 | —CH₂—OCH₃ | —CH₂COOH | 2-Cl-benzyl | $C_{33}H_{35}ClN_4O_7S$ | 667.19 | 667.2 |

-continued

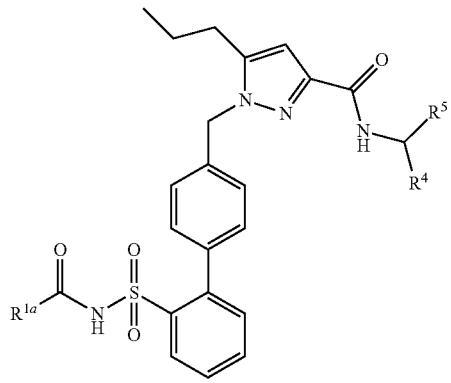

| # | $R^{1a}$ | $R^4$ | $R^5$ | Formula | MS m/z: [M + H]⁺ calcd | found |
|---|---|---|---|---|---|---|
| 19 | —C(CH₃)₂NH₂ | —CH(OH)—COOH | benzyl | $C_{34}H_{39}N_5O_7S$ | 662.26 | 662.4 |
| 20 | —N(CH₃)₂ | —CH(OH)—COOH | benzyl | $C_{33}H_{37}N_5O_7S$ | 648.24 | 648.6 |
| 21 | 1-pyrrolidyl | —CH(OH)—COOH | benzyl | $C_{35}H_{39}N_5O_7S$ | 674.26 | 674.6 |
| 22 | 4-morpholinyl | —CH(OH)—COOH | benzyl | $C_{35}H_{39}N_5O_8S$ | 690.25 | 690.4 |

1. (2R,3R)-3-(1-((2'-(N-(ethylcarbamoyl)sulfamoyl)biphenyl-4-yl)methyl)-5-propyl-1H-pyrazole-3-carboxamido)-2-hydroxy-4-phenylbutanoic acid
2. (2R,3R)-3-({1-[2'-(Cyclopropanecarbonylsulfamoyl)biphenyl-4-ylmethyl]-5-propyl-1H-pyrazole-3-carbonyl}amino)-2-hydroxy-4-phenylbutyric acid
3. (2R,3R)-3-({1-[2'-(2-Fluorobenzoylsulfamoyl)biphenyl-4-ylmethyl]-5-propyl-1H-pyrazole-3-carbonyl}amino)-2-hydroxy-4-phenylbutyric acid
4. (2R,3R)-2-Hydroxy-4-phenyl-3-[(5-propyl-1-{2'-[(pyridine-4-carbonyl)sulfamoyl]biphenyl-4-ylmethyl}-1H-pyrazole-3-carbonyl)amino]butyric acid
5. (2R,3R)-2-Hydroxy-3-[(1-{2'-[(5-methylisoxazole-3-carbonyl)sulfamoyl]biphenyl-4-ylmethyl}-5-propyl-1H-pyrazole-3-carbonyl)amino]-4-phenylbutyric acid
6. (2R,3R)-2-Hydroxy-3-[(1-{2'-[(isoxazole-5-carbonyl)sulfamoyl]biphenyl-4-ylmethyl}-5-propyl-1H-pyrazole-3-carbonyl)amino]-4-phenylbutyric acid
7. (2R,3R)-3-(1-((2'-(N-(ethoxycarbonyl)sulfamoyl)biphenyl-4-yl)methyl)-5-propyl-1H-pyrazole-3-carboxamido)-2-hydroxy-4-phenylbutanoic acid
8. (2R,3R)-2-Hydroxy-3-({1-[2'-(2-methoxyacetylsulfamoyl)biphenyl-4-ylmethyl]-5-propyl-1H-pyrazole-3-carbonyl}amino)-4-phenylbutyric acid
9. (2R,3R)-2-Hydroxy-4-phenyl-3-[(5-propyl-1-{2'-[(pyridine-2-carbonyl)sulfamoyl]biphenyl-4-ylmethyl}-1H-pyrazole-3-carbonyl)amino]butyric acid
10. (2R,3R)-2-Hydroxy-4-phenyl-3-{[1-(2'-propionylsulfamoylbiphenyl-4-ylmethyl)-5-propyl-1H-pyrazole-3-carbonyl]amino}butyric acid
11. (2R,3R)-2-hydroxy-3-{1-((2'-(N-(methylcarbamoyl)sulfamoyl)biphenyl-4-yl)methyl-5-propyl-1H-pyrazole-3-carboxamido)-4-phenylbutanoic acid
12. (2R,3R)-3-{[1-(2'-Benzoylsulfamoylbiphenyl-4-ylmethyl)-5-propyl-1H-pyrazole-3-carbonyl]amino}-2-hydroxy-4-phenylbutyric acid
13. (2R,3R)-2-Hydroxy-3-({1-[2'-((S)-2-hydroxypropionylsulfamoyl)biphenyl-4-ylmethyl]-5-propyl-1H-pyrazole-3-carbonyl}amino)-4-phenylbutyric acid
14. (2R,3R)-2-Hydroxy-3-({1-[2'-(2-hydroxy-2-methylpropionylsulfamoyl)biphenyl-4-ylmethyl]-5-propyl-1H-pyrazole-3-carbonyl}amino)-4-phenylbutyric acid
15. (2R,3R)-2-Hydroxy-3-({1-[2'-(2-hydroxyacetylsulfamoyl)biphenyl-4-ylmethyl]-5-propyl-1H-pyrazole-3-carbonyl}amino)-4-phenylbutyric acid
16. (2R,3R)-2-Hydroxy-3-({1-[2'-((R)-2-hydroxypropionylsulfamoyl)biphenyl-4-ylmethyl]-5-propyl-1H-pyrazole-3-carbonyl}amino)-4-phenylbutyric acid
17. (2R,3R)-2-Hydroxy-3-({1-[2'-(3-methoxy-propionylsulfamoyl)biphenyl-4-ylmethyl]-5-propyl-1H-pyrazole-3-carbonyl}amino)-4-phenylbutyric acid
18. ((R)-4-(2-Chlorophenyl)-3-({1-[2'-(2-methoxyacetylsulfamoyl)biphenyl-4-ylmethyl]-5-propyl-1H-pyrazole-3-carbonyl}amino)butyric acid
19. (2R,3R)-3-({1-[2'-(2-Amino-2-methylpropionylsulfamoyl)biphenyl-4-ylmethyl]-5-propyl-1H-pyrazole-3-carbonyl}amino)-2-hydroxy-4-phenylbutyric acid
20. (2R,3R)-3-(1-((2'-(N-(dimethylcarbamoyl)sulfamoyl)biphenyl-4-yl)methyl)-5-propyl-1H-pyrazole-3-carboxamido)-2-hydroxy-4-phenylbutanoic acid
21. (2R,3R)-2-Hydroxy-4-phenyl-3-[(5-propyl-1-{2'-[(pyrrolidine-1-carbonyl)sulfamoyl]biphenyl-4-ylmethyl}-1H-pyrazole-3-carbonyl)amino]butyric acid
22. (2R,3R)-2-Hydroxy-3-[(1-{2'-[(morpholine-4-carbonyl)sulfamoyl]biphenyl-4-ylmethyl}-5-propyl-1H-pyrazole-3-carbonyl)amino+-4-phenylbutyric acid

Preparation 12

1-(2'-t-Butoxycarbonyl-3-fluorobiphenyl-4-ylmethyl)-5-propyl-1H-pyrazole-3-carboxylic acid

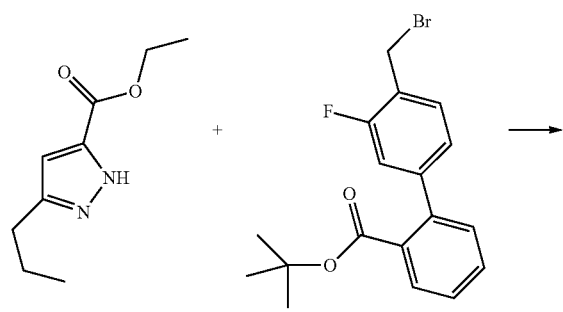

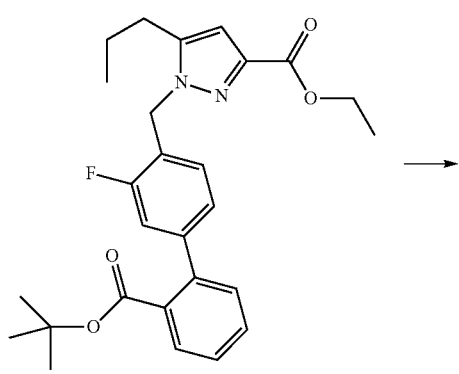

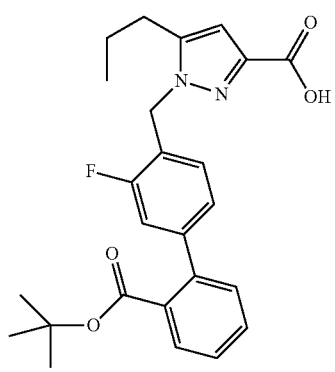

Ethyl 3-n-propylpyrazole-5-carboxylate (1.05 g, 5.8 mmol), 4'-bromomethyl-3'-fluorobiphenyl-2-carboxylic acid t-butyl ester (2.0 g, 5.8 mmol), and potassium carbonate (1.6 g, 11.5 mmol) were dissolved in DMF (10 mL). The mixture was stirred at 65° C. for 16 hours, then diluted with EtOAc. The organic layer was washed with saturated NaHCO₃ and saturated aqueous NaCl, and dried over Na₂SO₄. The solvent was removed in vacuo and the residue was purified by flash chromatography (EtOAc in hexanes) to yield 1-(2'-t-butoxycarbonyl-3-fluorobiphenyl-4-ylmethyl)-5-propyl-1H-pyrazole-3-carboxylic acid ethyl ester (2.7 g).

1-(2'-t-Butoxycarbonyl-3-fluorobiphenyl-4-ylmethyl)-5-propyl-1H-pyrazole-3-carboxylic acid ethyl ester (758 mg, 1.6 mmol) was diluted with MeOH (10 mL, 0.2 mol), and LiOH (233 mg, 4.9 mmol) was added. The mixture was stirred overnight then concentrated to dryness. The residue was dissolved in DCM and water and the aqueous layer was neutralized with AcOH. The water layer was extracted with DCM and the combined organic layers were washed with saturated aqueous NaCl and dried over Na₂SO₄. The crude product was purified by flash chromatography (EtOAc in hexanes) to yield the title compound (710 mg).

Example 8

4'-[3-((R)-1-Benzyl-2-mercaptoethylcarbamoyl)-5-propylpyrazol-1-yl methyl]-3'-fluorobiphenyl-2-carboxylic acid

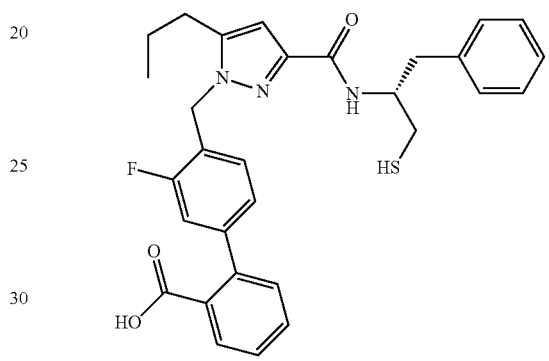

1-(2'-t-Butoxycarbonyl-3-fluorobiphenyl-4-ylmethyl)-5-propyl-1H-pyrazole-3-carboxylic acid (150 mg, 342 µmol) was dissolved into DMF (5 mL). HATU (130 mg, 342 µmol) was added and the mixture was stirred for 15 minutes. (R)-2-((R)-2-Amino-3-phenylpropyldisulfanyl)-1-benzylethylamine.2[HCl] (69.3 mg, 171 µmol) was added followed by DIPEA (149 µL, 855 µmol). The mixture was stirred at room temperature for 5 minutes then warmed to 45° C. After 5 hours, the mixture was cooled to room temperature and partitioned between EtOAc (25 mL) and 10% LiCl (10 mL). The organic was then washed with saturated NaHCO₃ (10 mL), saturated aqueous NaCl, dried over MgSO₄ and was concentrated to yield a brown oil. The mixture was chromatographed with 1:1 EtOAc:hexanes to obtain the dimer intermediate, which was dissolved in 30% TFA:DCM (10 mL) and stirred for 3 hours at room temperature. The mixture was concentrated under reduced pressure and dried under high vacuum. The material was redissolved in THF (5 mL), and a solution of tris(2-carboxyethyl)phosphine hydrochloride (120 mg, 430 µmol) in water (0.5 mL) was added. The resulting mixture was stirred at room temperature for 3 hours, then concentrated and dissolved in 1:1 AcOH/water. The crude solution was filtered and chromatographed (1:1 water/MeCN with 0.1% TFA) to obtain the title compound (100 mg). MS m/z: [M+H]⁺ calcd for $C_{30}H_{30}FN_3O_3S$, 532.20. found 532.4.

Example 9

Following the procedures described in the examples above, and substituting the appropriate starting materials and reagents, compounds 9-1 to 9-7, having the following formula, were prepared:

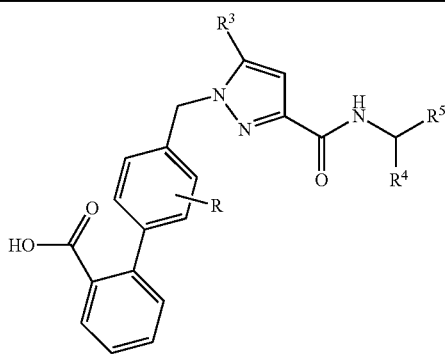

| # | R | $R^3$ | $R^4$ | $R^5$ | Formula | MS m/z: $[M+H]^+$ calcd | found |
|---|---|---|---|---|---|---|---|
| 1 | 3-F | propyl | —CH$_2$SH | i-butyl | C$_{27}$H$_{32}$FN$_3$O$_3$S | 498.22 | 498.6 |
| 2 | 3-F | ethoxy | —CH$_2$SH | benzyl | C$_{29}$H$_{28}$FN$_3$O$_4$S | 534.18 | 534.4 |
| 3 | 3-F | butyl | —CH$_2$SH | i-butyl | C$_{28}$H$_{34}$FN$_3$O$_3$S | 512.23 | 512.6 |
| 4 | 3-F | butyl | —CH$_2$SH | benzyl | C$_{31}$H$_{32}$FN$_3$O$_3$S | 546.22 | 546.6 |
| 5 | — | propyl | —CH(OH)—COOH | benzyl | C$_{31}$H$_{31}$N$_3$O$_6$ | 542.22 | 542.8 |
| 6 | — | propyl | —CH$_2$SH | benzyl | C$_{30}$H$_{31}$N$_3$O$_3$S | 514.21 | 514.6 |
| 7 | 2,3-diF | propyl | —CH(OH)—COOH | benzyl | C$_{31}$H$_{29}$F$_2$N$_3$O$_6$ | 578.20 | 578.6 |

1. 3'-Fluoro-4'-[3-((R)-1-mercaptomethyl-3-methylbutylcarbamoyl)-5-propylpyrazol-1-ylmethyl]biphenyl-2-carboxylic acid
2. 4'-[3-((R)-1-Benzyl-2-mercaptoethylcarbamoyl)-5-ethoxypyrazol-1-ylmethyl]-3'-fluorobiphenyl-2-carboxylic acid
3. 4'-[5-Butyl-3-((R)-1-mercaptomethyl-3-methylbutylcarbamoyl)-pyrazol-1-ylmethyl]-3'-fluorobiphenyl-2-carboxylic acid
4. 4'-[3-((R)-1-Benzyl-2-mercaptoethylcarbamoyl)-5-butylpyrazol-1-ylmethyl]-3'-fluorobiphenyl-2-carboxylic acid
5. 4'-[3-((1R,2R)-1-Benzyl-2-carboxy-2-hydroxyethylcarbamoyl)-5-propylpyrazol-1-ylmethyl]biphenyl-2-carboxylic acid
6. 4'-[3-((R)-1-Mercaptomethyl-2-phenylethylcarbamoyl)-5-propylpyrazol-1-ylmethyl]biphenyl-2-carboxylic acid
7. 4'-[3-((1R,2R)-1-Benzyl-2-carboxy-2-hydroxyethylcarbamoyl)-5-propylpyrazol-1-ylmethyl]-2',3'-difluorobiphenyl-2-carboxylic acid Preparation 13

5-Propyl-1-{6-[2-(1H-tetrazol-5-yl)phenyl]pyridin-3-ylmethyl}-1H-pyrazole-3-carboxylic Acid

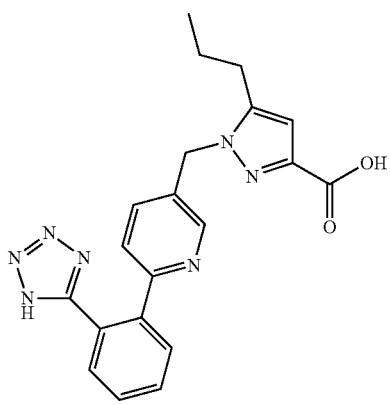 [SMILES: CCCc1cc(C(=O)O)nn1Cc1ccc(-c2ccccc2-c2nnn[nH]2)nc1]

A solution of (tetrazol-5-yl)phenylboronic acid (180 mg, 0.97 mmol), 1-(6-bromopyridin-3-ylmethyl)-5-propyl-1H-pyrazole-3-carboxylic acid ethyl ester (285 mg, 809 μmol), tetrakis(triphenylphosphine)palladium(0) (50 mg, 40 μmol), 1.0 M NaOH in water (3.2 mL, 3.2 mmol) and MeOH (4.0 mL, 100 mmol) was sparged shortly, capped under nitrogen and heated in the microwave at 90° C. for 2 hours. The mixture was filtered to remove the Pd (rinsed with MeOH). The filtrate was concentrated to remove the MeOH, then extracted with EtOAc. The organic layer was extracted with 1 N NaOH. The combined aqueous layers were acidified with 1 N HCl to pH 3-4 and extracted with EtOAc. The organics were dried over MgSO$_4$, filtered and concentrated to yield the title compound (122 mg), which was used without further purification.

Example 10

(R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric Acid

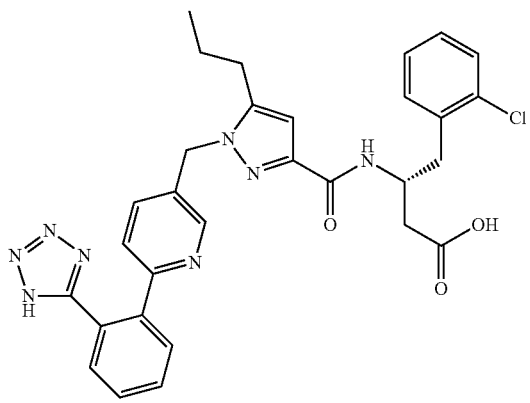 [SMILES: CCCc1cc(C(=O)N[C@@H](CC(=O)O)Cc2ccccc2Cl)nn1Cc1ccc(-c2ccccc2-c2nnn[nH]2)nc1]

A solution of 5-propyl-1-{6-[2-(1H-tetrazol-5-yl)phenyl]pyridin-3-ylmethyl}-1H-pyrazole-3-carboxylic acid (20 mg, 0.05 mmol), HATU (19.5 mg, 0.0514 mmol) and DIPEA (44.7 uL, 257 µmol) in DMF (1.59 mL, 20.5 mmol) was stirred to pre-activate the acid. After 30 minutes, (R)-3-amino-4-(2-chlorophenyl)butanoic acid.HCl (12.8 mg, 0.0514 mmol)) was added. The resulting solution was stirred overnight. The mixture was concentrated, re-dissolved in water/MeCN/TFA and purified using reverse phase liquid chromatography to yield the title compound (20.5 mg; 100% purity) as a TFA salt. MS m/z: [M+H]$^+$ calcd for $C_{30}H_{29}ClN_8O_3$, 585.21. found 585.4.

Example 11

(R)-3-[(5-Propyl-1-{6-[2-(1H-tetrazol-5-yl)-phenyl]-pyridin-3-ylmethyl}-1H-pyrazole-3-carbonyl)-amino]-4-(2-trifluoromethylphenyl)butyric Acid

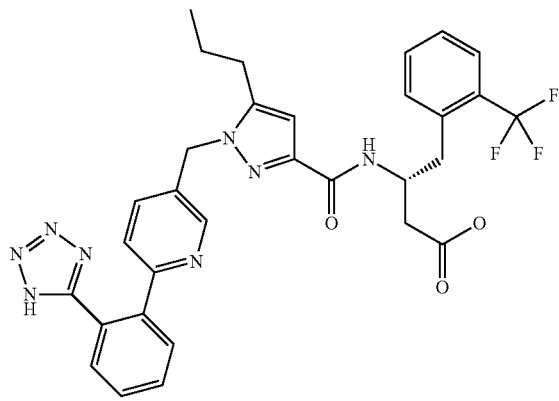 [SMILES: CCCc1cc(C(=O)N[C@@H](CC(=O)O)Cc2ccccc2C(F)(F)F)nn1Cc1ccc(-c2ccccc2-c2nnn[nH]2)nc1]

A solution of 5-propyl-1-{6-[2-(1H-tetrazol-5-yl)-phenyl]pyridin-3-ylmethyl}-1H-pyrazole-3-carboxylic acid (20 mg, 0.05 mmol), HATU (19.5 mg, 0.0514 mmol) and DIPEA (44.7 uL, 0.257 mmol) in DMF (1.59 mL, 20.5 mmol) was stirred to pre-activate the acid. After 30 minutes, (R)-3-amino-4-(2-trifluoromethylphenyl)butanoic acid.HCl (14.6 mg, 51.4 µmol)) was added. The resulting solution was stirred overnight. The mixture was concentrated, re-dissolved in water/MeCN/TFA and purified using reverse phase liquid chromatography to yield the title compound (21.1 mg; 100% purity) as a TFA salt. MS m/z: [M+H]$^+$ calcd for $C_{31}H_{29}F_3N_8O_3$, 619.23. found 619.6.

Example 12

(R)-4-(2-Fluorophenyl)-3-[(5-propyl-1-{6-[2-(1H-tetrazol-5-yl)phenyl]pyridin-3-ylmethyl}-1H-pyrazole-3-carbonyl)amino]butyric acid

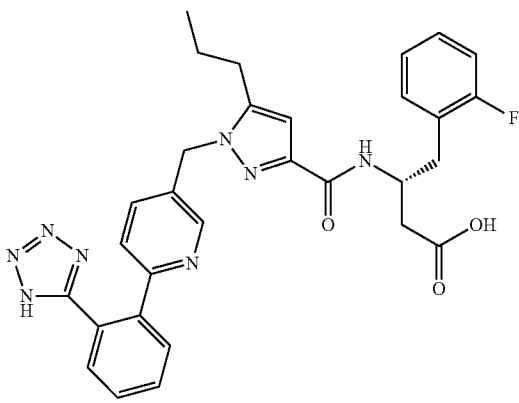 [SMILES: CCCc1cc(C(=O)N[C@@H](CC(=O)O)Cc2ccccc2F)nn1Cc1ccc(-c2ccccc2-c2nnn[nH]2)nc1]

A solution of 5-propyl-1-{6-[2-(1H-tetrazol-5-yl)phenyl]pyridin-3-ylmethyl}-1H-pyrazole-3-carboxylic acid (40 mg, 103 µmol), HATU (39.0 mg, 0.103 mmol) and DIPEA (89.4 uL, 514 µmol) in DMF (3.2 mL, 41.1 mmol) was stirred to pre-activate the acid. After 30 minutes, (R)-3-amino-4-(2-fluorophenyl)butanoic acid.HCl (24.0 mg, 103 µmol) was added. The resulting solution was stirred overnight. The mixture was concentrated, re-dissolved in water/MeCN/TFA and purified using reverse phase liquid chromatography to yield the title compound (15.7 mg; 100% purity) as a TFA salt. MS m/z: [M+H]$^+$ calcd for $C_{30}H_{29}FN_8O_3$, 569.23. found 569.2.

Preparation 14

1-(6-Bromopyridin-3-ylmethyl)-5-propyl-1H-pyrazole-3-carboxylic acid ethyl ester

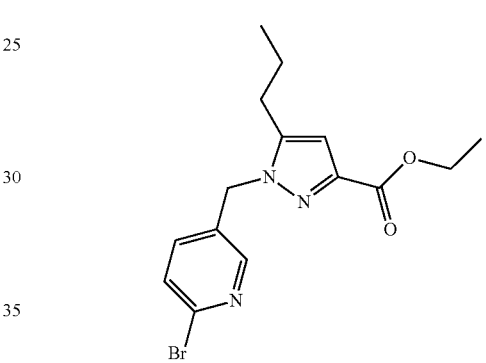

To a solution of 2-Bromo-5-methylpyridine (3.1 g, 17.4 mmol) in carbon tetrachloride (40 mL, 400 mmol) was added benzoyl peroxide (230 mg, 950 µmol) and NBS (3.4 g, 19.2 mmol). The resulting mixture was heated at reflux overnight. The mixture was cooled at 0° C. and the NBS was removed by filtration. The filtrate was concentrated to yield 2-bromo-5-bromomethylpyridine (4.6 g), which was used directly in the next step.

Ethyl 3-n-propylpyrazole-5-carboxylate (1.7 g, 9.1 mmol), 2-bromo-5-bromomethylpyridine (4.6 g, 9.1 mmol) and potassium carbonate (1.8 g, 12.7 mmol) were dissolved in DMF (70.0 mL, 904 mmol). The resulting suspension was stirred at room temperature overnight. The material was diluted with aqueous. NaHCO$_3$ and diethyl ether. The aqueous layer was further extracted with diethyl ether. The combined organics were dried over MgSO$_4$, filtered and concentrated. The residue was purified using flash chromatography [1$^{st}$ 30:1 hexanes/EtOAc; 2$^{nd}$ 10:1 hexanes/EtOAc]. The two isomers were separated and analyzed by NMR and NOE: 1-(6-bromopyridin-3-ylmethyl)-5-propyl-1H-pyrazole-3-carboxylic acid ethyl ester (1.2 g) and 2-(6-bromopyridin-3-ylmethyl)-5-propyl-2H-pyrazole-3-carboxylic acid ethyl ester.

Preparation 15

1-[6-(2-Acetylsulfamoylphenyl)pyridin-3-ylmethyl]-5-propyl-1H-pyrazole-3-carboxylic Acid

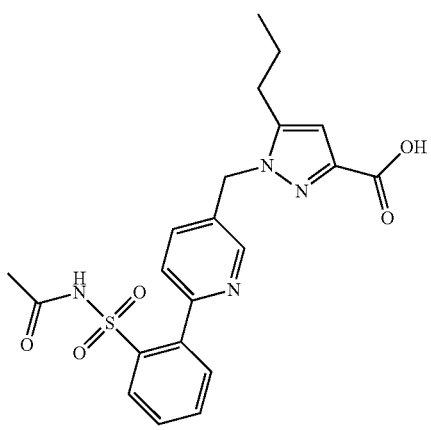 [SMILES: CCCc1cc(C(=O)O)nn1Cc1ccc(-c2ccccc2S(=O)(=O)NC(C)=O)nc1]

To a suspension of N-t-butyl-2-(4,4,5,5-tetramethyl-1,3,2-dioxaborolan-2-yl)-benzenesulfonamide (722 mg, 2.1 mmol) and 1-(6-bromopyridin-3-ylmethyl)-5-propyl-1H-pyrazole-3-carboxylic acid ethyl ester (500 mg, 1.4 mmol) in toluene (4.0 mL, 37 mmol) was added a solution of potassium carbonate (392 mg, 2.84 mmol) in water (530 μL, 30 mmol). The resulting solution was sparged shortly with nitrogen before tetrakis(triphenylphosphine)-palladium(0) (328 mg, 284 μmol) was added. The mixture heated in the microwave at 100° C. for 30 minutes, then cooled to room temperature. Aqueous 1% citric acid was added, the mixture was extracted with EtOAc. The combined organics were partially concentrated, filtered through Celite® (EtOAc rinse), and concentrated. The crude residue was diluted with t-butyl alcohol (21.6 mL, 226 mmol), and 0.20 M LiOH in water (42.6 mL, 8.5 mmol) was added. The mixture was stirred overnight, then concentrated and extracted with EtOAc. The EtOAc was back-extracted with 1 N LiOH. The combined aqueous layers were acidified with 1 N HCl to pH 4-5. The acidic aqueous layer was extracted with EtOAc and DCM to yield 1-[6-((2-t-butylsulfamoylphenyl)pyridin-3-ylmethyl]-5-propyl-1H-pyrazole-3-carboxylic acid (630 mg).

1-[6-(2-t-Butylsulfamoylphenyl)pyridin-3-ylmethyl]-5-propyl-1H-pyrazole-3-carboxylic acid (480 mg, 1.0 mmol) was dissolved in TFA (2.8 mL, 36.8 mmol) and heated at 40° C. for 3 hours. The mixture was diluted with toluene and concentrated (azeotrope×3). The residue was dissolved in DCM (5.53 mL, 86.2 mmol), then triethylamine (1.8 mL, 12.6 mmol) and acetic anhydride (992 μL, 10.5 mmol) were added. The resulting solution was stirred at room temperature for 1 hour. Additional triethylamine and acetic anhydride were added to drive the reaction. The reaction was then quenched with water (150 μL) and dried through azeotrope with toluene to yield the title compound (108 mg), which was used without further purification.

Example 13

(2R,3R)-3-({1-[6-(2-Acetylsulfamoylphenyl)pyridin-3-ylmethyl]-5-propyl-1H-pyrazole-3-carbonyl}amino)-2-hydroxy-4-phenylbutyric Acid

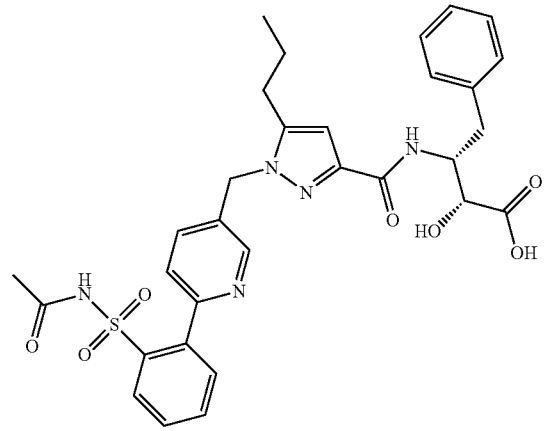 [SMILES: CCCc1cc(C(=O)N[C@H](Cc2ccccc2)[C@@H](O)C(=O)O)nn1Cc1ccc(-c2ccccc2S(=O)(=O)NC(C)=O)nc1]

A solution of 1-[6-(2-acetylsulfamoylphenyl)pyridin-3-ylmethyl]-5-propyl-1H-pyrazole-3-carboxylic acid (100 mg, 226 μmol) in DMF (7.0 mL, 90 mmol) was added to HATU (85.9 mg, 226 μmol). The resulting mixture was stirred for 5 minutes before (2R,3R)-3-amino-2-hydroxy-4-phenylbutyric acid.HCl (52.4 mg, 226 μmol) and DIPEA (315 μL, 1.8 mmol) were added. The resulting solution was heated at 40° C. overnight. The mixture was concentrated, re-dissolved in water/MeCN/TFA and purified using reverse phase liquid chromatography to yield the title compound (48 mg; 91% purity) as a TFA salt. MS m/z: [M+H]$^+$ calcd for $C_{31}H_{33}N_5O_7S$, 620.21. found 620.4.

Example 14

Following the procedures described in the examples above, and substituting the appropriate starting materials and reagents, compounds 14-1 to 14-15, having the following formula were prepared:

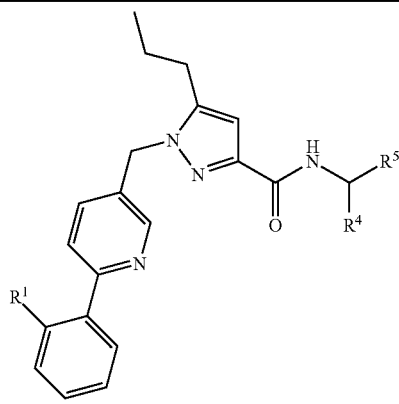

| # | R¹ | R⁴ | R⁵ | Formula | MS m/z: [M + H]⁺ calcd | found |
|---|---|---|---|---|---|---|
| 1 | 1H-tetrazol-5-yl | —CH(OH)—COOH | benzyl | $C_{30}H_{30}N_8O_4$ | 567.24 | 567.6 |
| 2 | 1H-tetrazol-5-yl | —CH₂SH | benzyl | $C_{29}H_{30}N_8OS$ | 539.23 | 539.6 |
| 3 | —SO₂NH—C(O)CH₃ | —CH₂SH | benzyl | $C_{30}H_{33}N_5O_4S_2$ | 592.20 | 592.6 |
| 4 | 1H-tetrazol-5-yl | —CH₂—COOH | 2-Br-benzyl | $C_{30}H_{29}BrN_8O_3$ | 629.15 | 631.4 |
| 5 | 1H-tetrazol-5-yl | —CH(OH)—COOH | 2-Cl-benzyl | $C_{30}H_{29}ClN_8O_4$ | 601.20 | 601.4 |
| 6 | 1H-tetrazol-5-yl | —CH₂—COOH | benzyl | $C_{30}H_{30}N_8O_3$ | 551.24 | 551.4 |
| 7 | 1H-tetrazol-5-yl | —CH₂—COOH | i-butyl | $C_{27}H_{32}N_8O_3$ | 517.26 | 517.4 |
| 8 | 1H-tetrazol-5-yl | —CH(OH)—COOH | i-butyl | $C_{27}H_{32}N_8O_4$ | 533.25 | 533.2 |
| 9 | 1H-tetrazol-5-yl | —CH(OH)—COOH | benzyl | $C_{30}H_{30}N_8O_4$ | 567.24 | 567.6 |
| 10 | 1H-tetrazol-5-yl | —CH₂—COOH | thiophen-3-ylmethyl | $C_{28}H_{28}N_8O_3S$ | 557.20 | 557.2 |
| 11 | 1H-tetrazol-5-yl | —CH₂—COOH | furan-2-ylmethyl | $C_{28}H_{28}N_8O_4$ | 541.22 | 541.2 |
| 12 | 1H-tetrazol-5-yl | —CH₂—COOH | 3-F-benzyl | $C_{30}H_{29}FN_8O_3$ | 569.23 | 569.2 |
| 13 | 1H-tetrazol-5-yl | —CH₂—COOH | 4-F-benzyl | $C_{30}H_{29}FN_8O_3$ | 569.23 | 569.2 |
| 14 | —SO₂NH—C(O)CH₃ | —CH₂—COOH | 2-Cl-benzyl | $C_{31}H_{32}ClN_5O_6S$ | 638.18 | 638.4 |
| 15 | —SO₂NH—C(O)CH₃ | —CH₂—COOH | benzyl | $C_{31}H_{33}N_5O_6S$ | 604.22 | 605.0 |

1. (2R,3R)-2-Hydroxy-4-phenyl-3-[(5-propyl-1-{6-[2-(1H-tetrazol-5-yl)-phenyl]pyridin-3-ylmethyl}-1H-pyrazole-3-carbonyl)amino]butyric acid (TFA salt)
2. 5-Propyl-1-{6-[2-(1H-tetrazol-5-yl)phenyl]pyridin-3-ylmethyl}-1H-pyrazole-3-carboxylic acid ((R)-1-benzyl-2-mercaptoethyl)amide (TFA salt)
3. 1-[6-(2-Acetylsulfamoyl-phenyl)pyridin-3-ylmethyl]-5-propyl-1H-pyrazole-3-carboxylic acid ((R)-1-benzyl-2-mercaptoethyl)amide (TFA salt)
4. (R)-4-(2-Bromophenyl)-3-[(5-propyl-1-{6-[2-(1H-tetrazol-5-yl)-phenyl]-pyridin-3-ylmethyl}-1H-pyrazole-3-carbonyl)amino]butyric acid (TFA salt)
5. (2R,3R)-4-(2-Chlorophenyl)-2-hydroxy-3-[(5-propyl-1-{6-[2-(1H-tetrazol-5-yl)phenyl]pyridin-3-ylmethyl}-1H-pyrazole-3-carbonyl)amino]butyric acid (TFA salt)
6. (R)-4-Phenyl-3-[(5-propyl-1-{6-[2-(1H-tetrazol-5-yl)-phenyl]-pyridin-3-ylmethyl}-1H-pyrazole-3-carbonyl)amino]butyric acid (TFA salt)
7. (R)-5-Methyl-3-[(5-propyl-1-{6-[2-(1H-tetrazol-5-yl)-phenyl]-pyridin-3-ylmethyl}-1H-pyrazole-3-carbonyl)-amino]hexanoic acid (TFA salt)
8. (2R,3R)-2-Hydroxy-5-methyl-3-[(5-propyl-1-{6-[2-(1H-tetrazol-5-yl)phenyl]pyridin-3-ylmethyl}-1H-pyrazole-3-carbonyl)amino]hexanoic acid d (TFA salt)
9. (2S,3R)-2-Hydroxy-4-phenyl-3-[(5-propyl-1-{6-[2-(1H-tetrazol-5-yl)phenyl]pyridin-3-ylmethyl}-1H-pyrazole-3-carbonyl)amino]butyric acid (TFA salt)
10. (R)-3-[(5-Propyl-1-{6-[2-(1H-tetrazol-5-yl)-phenyl]-pyridin-3-ylmethyl}-1H-pyrazole-3-carbonyl)-amino]-4-thiophen-3-yl-butyric acid (TFA salt)
11. (R)-4-Furan-2-yl-3-[(5-propyl-1-{6-[2-(1H-tetrazol-5-yl)phenyl]pyridin-3-ylmethyl}-1H-pyrazole-3-carbonyl)amino]butyric acid (TFA salt)
12. (R)-4-(3-Fluorophenyl)-3-[(5-propyl-1-{6-[2-(1H-tetrazol-5-yl)phenyl]pyridin-3-ylmethyl}-1H-pyrazole-3-carbonyl)amino]butyric acid (TFA salt)
13. (R)-4-(4-Fluorophenyl)-3-[(5-propyl-1-{6-[2-(1H-tetrazol-5-yl)phenyl]pyridin-3-ylmethyl}-1H-pyrazole-3-carbonyl)amino]butyric acid (TFA salt)
14. (R)-3-({1-[6-(2-Acetylsulfamoylphenyl)-pyridin-3-ylmethyl]-5-propyl-1H-pyrazole-3-carbonyl}-amino)-4-(2-chlorophenyl)butyric acid (TFA salt)
15. (R)-3-({1-[6-(2-Acetylsulfamoylphenyl)-pyridin-3-ylmethyl]-5-propyl-1H-pyrazole-3-carbonyl}-amino)-4-phenylbutyric acid (TFA salt)

Example 15

Following the procedures described in the examples above, and substituting the appropriate starting materials and reagents, compounds 15-1 to 15-4, having the following formula were prepared:

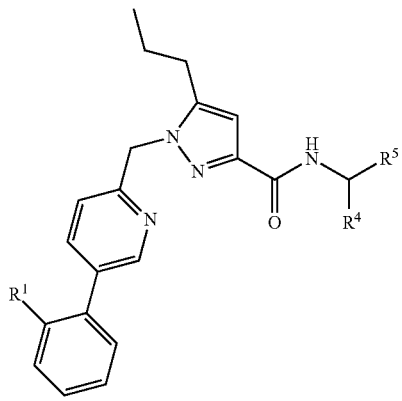

| # | R¹ | R⁴ | R⁵ | Formula | MS m/z: [M + H]⁺ calcd | found |
|---|---|---|---|---|---|---|
| 1 | 1H-tetrazol-5-yl | —CH(OH)—COOH | benzyl | $C_{30}H_{30}N_8O_4$ | 567.24 | 567.6 |
| 2 | 1H-tetrazol-5-yl | —CH₂—COOH | 2-Cl-benzyl | $C_{30}H_{29}ClN_8O_3$ | 585.21 | 585.4 |
| 3 | —SO₂NH—C(O)CH₃ | —CH(OH)—COOH | benzyl | $C_{31}H_{33}N_5O_7S$ | 620.21 | 620.6 |
| 4 | —SO₂NH—C(O)CH₃ | —CH₂—COOH | 2-Cl-benzyl | $C_{31}H_{32}ClN_5O_6S$ | 638.18 | 638.4 |

1. (2R,3R)-2-Hydroxy-4-phenyl-3-[(5-propyl-1-{5-[2-(1H-tetrazol-5-yl)phenyl]pyridin-2-ylmethyl}-1H-pyrazole-3-carbonyl)amino]butyric acid (TFA salt)
2. (R)-4-(2-Chlorophenyl)-3-[(5-propyl-1-{5-[2-(1H-tetrazol-5-yl)phenyl]pyridin-2-ylmethyl}-1H-pyrazole-3-carbonyl)amino]butyric acid (TFA salt)
3. (2R,3R)-3-({1-[5-(2-Acetylsulfamoylphenyl)pyridin-2-ylmethyl]-5-propyl-1H-pyrazole-3-carbonyl}amino)-2-hydroxy-4-phenylbutyric acid (TFA salt)
4. (R)-3-({1-[5-(2-Acetylsulfamoylphenyl)pyridin-2-ylmethyl]-5-propyl-1H-pyrazole-3-carbonyl}amino)-4-(2-chlorophenyl)butyric acid (TFA salt)

Example 16

Following the procedures described in the examples above, and substituting the appropriate starting materials and reagents, compounds 16-1 to 16-7, having the following formula, were prepared:

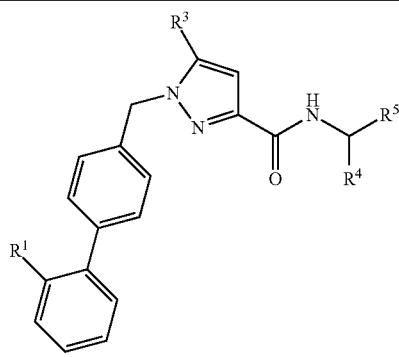

| # | R¹ | R³ | R⁴ | R⁵ | Formula | MS m/z: [M + H]⁺ calcd | found |
|---|---|---|---|---|---|---|---|
| 1 | ![oxadiazolone] | propyl | —CH₂SH | benzyl | $C_{31}H_{31}N_5O_3S$ | 554.22 | 554.4 |

-continued
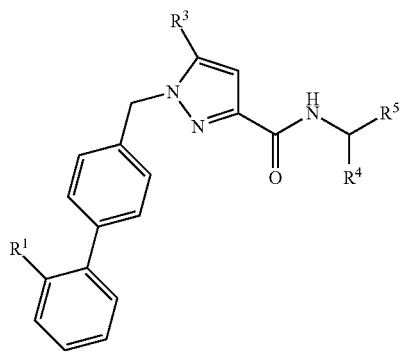
| # | R¹ | R³ | R⁴ | R⁵ | Formula | MS m/z: [M + H]⁺ calcd | found |
|---|---|---|---|---|---|---|---|
| 2 | | propyl | —CH(OH)—COOH | benzyl | $C_{32}H_{31}N_5O_6$ | 582.23 | 582.4 |
| 3 | | propyl | —CH(OH)—COOH | benzyl | $C_{31}H_{31}N_7O_5$ | 582.24 | 582.6 |
| 4 | | propyl | —CH₂—COOH | benzyl | $C_{31}H_{31}N_7O_4$ | 566.24 | 567.0 |
| 5 | | propyl | —CH₂—COOH | 2-Cl-benzyl | $C_{31}H_{30}ClN_7O_4$ | 600.21 | 600.6 |
| 6 | | propyl | —CH(OH)—COOH | 2-Cl-benzyl | $C_{31}H_{30}ClN_7O_5$ | 616.20 | 616.6 |

-continued

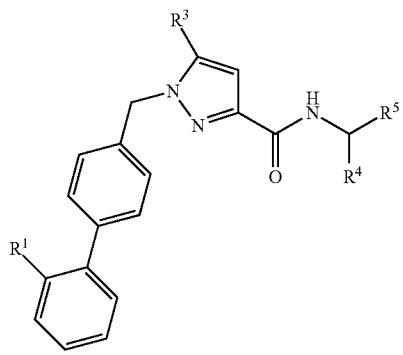

| # | R¹ | R³ | R⁴ | R⁵ | Formula | MS m/z: [M + H]⁺ calcd | found |
|---|---|---|---|---|---|---|---|
| 7 | (tetrazolinone) | ethoxy | —CH(OH)—COOH | benzyl | $C_{30}H_{29}N_7O_6$ | 584.22 | 584.6 |

1. 1-[2'-(5-Oxo-2,5-dihydro-[1,2,4]oxadiazol-3-yl)biphenyl-4-ylmethyl]-5-propyl-1H-pyrazole-3-carboxylic acid ((R)-1-benzyl-2-mercaptoethyl)amide
2. (2R,3R)-2-Hydroxy-3-({1-[2'-(5-oxo-2,5-dihydro-[1,2,4]oxadiazol-3-yl)biphenyl-4-ylmethyl]-5-propyl-1H-pyrazole-3-carbonyl}amino)-4-phenylbutyric acid
3. (2R,3R)-2-Hydroxy-3-({1-[2'-(5-oxo-4,5-dihydrotetrazol-1-yl)-biphenyl-4-ylmethyl]-5-propyl-1H-pyrazole-3-carbonyl}amino)-4-phenylbutyric acid
4. (R)-3-({1-[2'-(5-oxo-4,5-dihydrotetrazol-1-yl)-biphenyl-4-ylmethyl]-5-propyl-1H-pyrazole-3-carbonyl}amino)-4-phenylbutyric acid
5. (R)-4-(2-Chlorophenyl)-3-({1-[2'-(5-oxo-4,5-dihydrotetrazol-1-yl)-biphenyl-4-ylmethyl]-5-propyl-1H-pyrazole-3-carbonyl}amino)butyric acid
6. (2R,3R)-4-(2-Chlorophenyl)-2-hydroxy-3-({1-[2'-(5-oxo-4,5-dihydrotetrazol-1-yl)-biphenyl-4-ylmethyl]-5-propyl-1H-pyrazole-3-carbonyl}amino)butyric acid
7. (2R,3R)-3-({5-Ethoxy-1-[2'-(5-oxo-4,5-dihydrotetrazol-1-yl)-biphenyl-4-ylmethyl]-1H-pyrazole-3-carbonyl}amino)-2-hydroxy-4-phenylbutyric acid Example 17

Following the procedures described in the examples above, and substituting the appropriate starting materials and reagents, compounds 17-1 to 17-6, having the following formula were prepared:

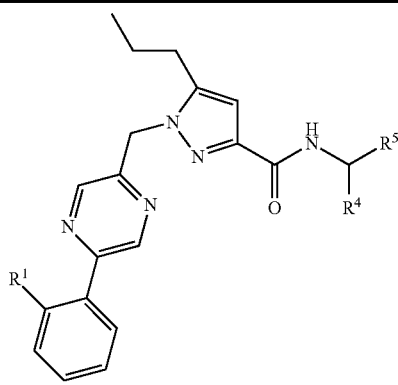

| # | R¹ | R⁴ | R⁵ | Formula | MS m/z: [M + H]⁺ calcd | found |
|---|---|---|---|---|---|---|
| 1 | 1H-tetrazol-5-yl | —CH₂—COOH | benzyl | $C_{29}H_{29}N_9O_3$ | 552.24 | 552.3 |
| 2 | 1H-tetrazol-5-yl | —CH₂—COOH | 2-Cl-benzyl | $C_{29}H_{28}ClN_9O_3$ | 586.20 | 586.2 |
| 3 | 1H-tetrazol-5-yl | —CH(OH)—COOH | benzyl | $C_{29}H_{29}N_9O_4$ | 568.23 | 568.8 |
| 4 | —SO₂NH—C(O)CH₃ | —CH₂—COOH | benzyl | $C_{30}H_{32}N_6O_6S$ | 605.21 | 605.8 |

-continued

| # | | | | Formula | calcd | found |
|---|---|---|---|---|---|---|
| 5 | —SO$_2$NH—C(O)CH$_3$ | —CH(OH)—COOH | benzyl | C$_{30}$H$_{32}$N$_6$O$_7$S | 621.21 | 621.8 |
| 6 | —SO$_2$NH—C(O)CH$_3$ | —CH$_2$—COOH | 2-Cl-benzyl | C$_{30}$H$_{31}$ClN$_6$O$_6$S | 639.17 | 639.4 |

1. (R)-4-Phenyl-3-[(5-propyl-1-{5-[2-(1H-tetrazol-5-yl)phenyl]pyrazin-2-ylmethyl}-1H-pyrazole-3-carbonyl)amino]butyric acid (TFA salt)
2. (R)-4-(2-Chlorophenyl)-3-[(5-propyl-1-{5-[2-(1H-tetrazol-5-yl)phenyl]pyrazin-2-ylmethyl}-1H-pyrazole-3-carbonyl)amino]butyric acid (TFA salt)
3. (2R,3R)-3-(1-((5-(2-(1H-tetrazol-5-yl)phenyl)pyrazin-2-yl)methyl)-5-propyl-1H-pyrazole-3-carboxamido)-2-hydroxy-4-phenylbutanoic acid (TFA salt)
4. (R)-3-({1-[5-(2-Acetylsulfamoylphenyl)pyrazin-2-ylmethyl]-5-propyl-1H-pyrazole-3-carbonyl}amino)-4-phenylbutyric acid (TFA salt)
5. (2R,3R)-3-({1-[5-(2-Acetylsulfamoylphenyl)pyrazin-2-ylmethyl]-5-propyl-1H-pyrazole-3-carbonyl}amino)-2-hydroxy-4-phenylbutyric acid (TFA salt)
6. (R)-3-({1-[5-(2-Acetylsulfamoyl-phenyl)-pyrazin-2-ylmethyl]-5-propyl-1H-pyrazole-3-carbonyl}amino)-4-(2-chloro-phenyl)butyric acid (TFA salt)

Example 18

Following the procedures described in the examples above, and substituting the appropriate starting materials and reagents, compound 18, having the following formula, was prepared:

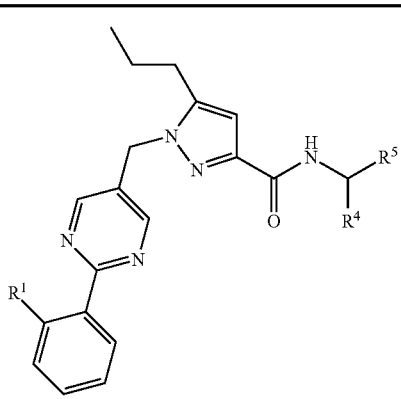

| # | R$^1$ | R$^4$ | R$^5$ | Formula | MS m/z: [M + H]$^+$ calcd | found |
|---|---|---|---|---|---|---|
| 1 | tetrazole | —CH$_2$COOH | 2-Cl-benzyl | C$_{29}$H$_{28}$ClN$_9$O$_3$ | 586.20 | 586.6 |

1. (R)-4-(2-Chlorophenyl)-3-[(5-propyl-1-{2-[2-(1H-tetrazol-5-yl)phenyl]pyrimidin-5-ylmethyl}-1H-pyrazole-3-carbonyl)amino]butyric acid (TFA salt)

Example 19

Following the procedures described in the examples above, and substituting the appropriate starting materials and reagents, compounds 19-1 to 19-3, having the following formula were prepared:

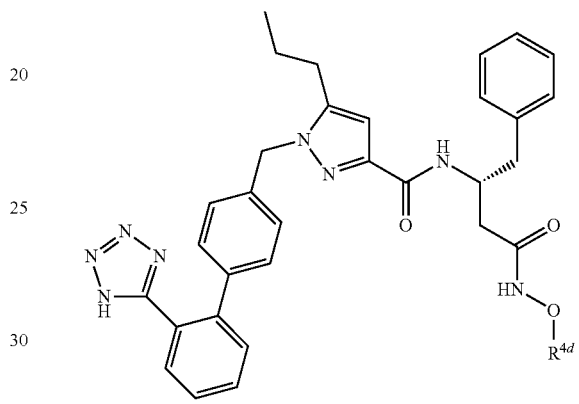

These compounds are prodrugs of the compound of Example 3-16.

| # | R$^{4d}$ | Formula | MS m/z: [M + H]$^+$ calcd | found |
|---|---|---|---|---|
| 1 | —C(O)CH$_3$ | C$_{33}$H$_{34}$N$_8$O$_4$ | 607.27 | 607.4 |
| 2 | —C(O)-phenyl | C$_{38}$H$_{36}$N$_8$O$_4$ | 669.29 | 669.5 |
| 3 | —C(O)—CH(NM$_2$)[CH(CH$_3$)$_2$] | C$_{36}$H$_{41}$N$_9$O$_4$ | 664.33 | 664.4 |

1. 5-Propyl-1-[2'-(1H-tetrazol-5-yl)biphenyl-4-ylmethyl]-1H-pyrazole-3-carboxylic acid [(R)-1-(acetoxycarbamoylmethyl)-2-phenylethyl]amide
2. 5-Propyl-1-[2'-(1H-tetrazol-5-yl)biphenyl-4-ylmethyl]-1H-pyrazole-3-carboxylic acid [(R)-1-(benzoyloxycarbamoyl-methyl)-2-phenylethyl]amide
3. 5-Propyl-1-[2'-(1H-tetrazol-5-yl)biphenyl-4-ylmethyl]-1H-pyrazole-3-carboxylic acid {(R)-1-[((R)-2-amino-3-methyl-butyryloxycarbamoyl)methyl]-2-phenylethyl}amide

Example 20

Following the procedures described in the examples above, and substituting the appropriate starting materials and reagents, compounds 20-1 to 20-11, having the following formula were prepared:

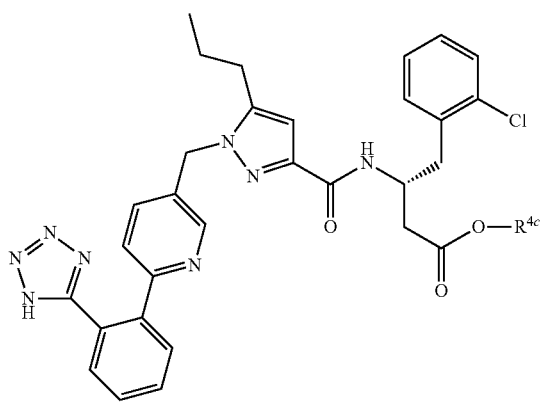

These compounds are prodrugs of the compound of Example 10.

| # | R$^{4c}$ | Formula | calcd | found |
|---|---|---|---|---|
| 1 | —CH$_2$CH$_3$ | C$_{32}$H$_{33}$ClN$_8$O$_3$ | 613.24 | 613.2 |
| 2 | —CH(CH$_3$)$_2$ | C$_{33}$H$_{35}$ClN$_8$O$_3$ | 627.25 | 627.7 |
| 3 | —(CH$_2$)$_3$CH$_3$ | C$_{34}$H$_{37}$ClN$_8$O$_3$ | 641.27 | 641.6 |
| 4 | —(CH$_2$)$_4$CH$_3$ | C$_{35}$H$_{39}$ClN$_8$O$_3$ | 655.28 | 655.2 |
| 5 | —(CH$_2$)$_2$CH$_3$ | C$_{33}$H$_{35}$ClN$_8$O$_3$ | 627.25 | 627.4 |
| 6 | (morpholinopropyl) | C$_{36}$H$_{40}$ClN$_9$O$_4$ | 698.29 | 698.6 |
| 7 | (5-methyl-2-oxo-1,3-dioxol-4-ylmethyl) | C$_{35}$H$_{33}$ClN$_8$O$_6$ | 697.22 | 697.2 |
| 8 | —CH(CH$_3$)OC(O)O-cyclohexyl | C$_{39}$H$_{43}$ClN$_8$O$_6$ | 755.30 | 755.4 |
| 9 | —CH(CH$_3$)OC(O)OCH$_2$CH$_3$ | C$_{35}$H$_{37}$ClN$_8$O$_6$ | 701.25 | 701.6 |
| 10 | —CH(CH$_3$)OC(O)OCH(CH$_3$)$_2$ | C$_{36}$H$_{39}$ClN$_8$O$_6$ | 715.27 | 715.6 |
| 11 | —CH$_3$ | C$_{31}$H$_{31}$ClN$_8$O$_3$ | 599.22 | 599.4 |

1. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid ethyl ester (TFA salt)
2. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid isopropyl ester (TFA salt)
3. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid butyl ester (TFA salt)
4. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid pentyl ester (TFA salt)
5. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid propyl ester (TFA salt)
6. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid 2-morpholin-4-yl-ethyl ester (TFA salt)
7. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid 5-methyl-2-oxo-[1,3]dioxol-4-ylmethyl ester (TFA salt)
8. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid 1-cyclohexyloxycarbonyloxy-ethyl ester (TFA salt)
9. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid 1-ethoxycarbonyloxy-ethyl ester (TFA salt)
10. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid 1-isopropoxycarbonyloxy-ethyl ester (TFA salt)
11. (R)-4-(2-Chlorophenyl)-3-[(5-propyl-1-{6-[2-(1H-tetrazol-5-yl)phenyl]pyridin-3-ylmethyl}-1H-pyrazole-3-carbonyl)amino]butyric acid methyl ester (TFA salt)

Example 21

Following the procedures described in the examples above, and substituting the appropriate starting materials and reagents, compounds 21-1 to 21-6, having the following formula were prepared:

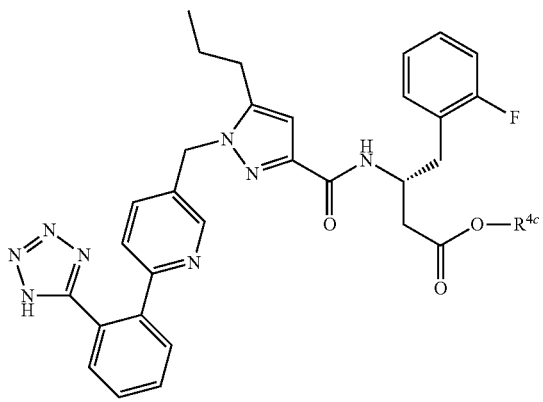

These compounds are prodrugs of the compound of Example 12.

| # | R$^{4c}$ | Formula | calcd | found |
|---|---|---|---|---|
| 1 | —CH$_2$CH$_3$ | C$_{32}$H$_{33}$FN$_8$O$_3$ | 597.27 | 597.6 |
| 2 | —(CH$_2$)$_2$CH$_3$ | C$_{33}$H$_{35}$FN$_8$O$_3$ | 611.28 | 611.4 |
| 3 | —(CH$_2$)$_3$CH$_3$ | C$_{34}$H$_{37}$FN$_8$O$_3$ | 625.30 | 625.6 |
| 4 | —(CH$_2$)$_4$CH$_3$ | C$_{35}$H$_{39}$FN$_8$O$_3$ | 639.31 | 639.6 |
| 5 | —CH(CH$_3$)$_2$ | C$_{33}$H$_{35}$FN$_8$O$_3$ | 611.28 | 611.6 |
| 6 | —CH3 | C$_{31}$H$_{31}$FN$_8$O$_3$ | 583.25 | 583.4 |

1. (R)-4-(2-Fluorophenyl)-3-[(5-propyl-1-{6-[2-(1H-tetrazol-5-yl)phenyl]pyridin-3-ylmethyl}-1H-pyrazole-3-carbonyl)amino]butyric acid ethyl ester (TFA salt)
2. (R)-4-(2-Fluorophenyl)-3-[(5-propyl-1-{6-[2-(1H-tetrazol-5-yl)phenyl]pyridin-3-ylmethyl}-1H-pyrazole-3-carbonyl)amino]butyric acid propyl ester (TFA salt)
3. (R)-4-(2-Fluorophenyl)-3-[(5-propyl-1-{6-[2-(1H-tetrazol-5-yl)phenyl]pyridin-3-ylmethyl}-1H-pyrazole-3-carbonyl)amino]butyric acid butyl ester (TFA salt)
4. (R)-4-(2-Fluorophenyl)-3-[(5-propyl-1-{6-[2-(1H-tetrazol-5-yl)phenyl]pyridin-3-ylmethyl}-1H-pyrazole-3-carbonyl)amino]butyric acid pentyl ester (TFA salt)
5. (R)-4-(2-Fluorophenyl)-3-[(5-propyl-1-{6-[2-(1H-tetrazol-5-yl)phenyl]pyridin-3-ylmethyl}-1H-pyrazole-3-carbonyl)amino]butyric acid isopropyl ester (TFA salt)
6. (R)-4-(2-Fluorophenyl)-3-[(5-propyl-1-{6-[2-(1H-tetrazol-5-yl)phenyl]pyridin-3-ylmethyl}-1H-pyrazole-3-carbonyl)amino]butyric acid methyl ester (TFA salt)

Example 22

Following the procedures described in the examples above, and substituting the appropriate starting materials and reagents, compounds 22-1 to 22-6, having the following formula were prepared:

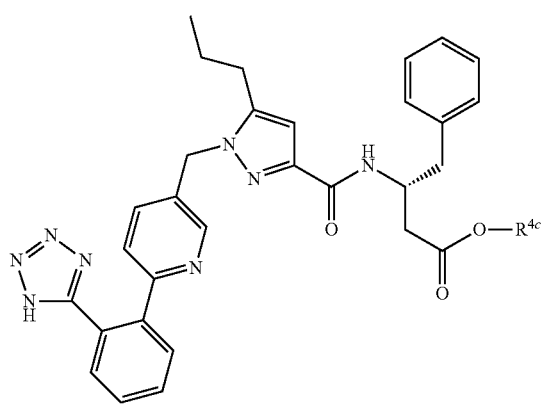

These compounds are prodrugs of the compound of Example 14-6.

| # | $R^{4c}$ | Formula | MS m/z: [M + H]+ calcd | found |
|---|---|---|---|---|
| 1 | —CH(CH₃)₂ | C₃₃H₃₆N₈O₃ | 593.29 | 593.2 |
| 2 | —(CH₂)₃CH₃ | C₃₄H₃₈N₈O₃ | 607.31 | 607.2 |
| 3 | —(CH₂)₄CH₃ | C₃₅H₄₀N₈O₃ | 621.32 | 621.2 |
| 4 | —CH₂CH₃ | C₃₂H₃₄N₈O₃ | 579.28 | 579.6 |
| 5 | —(CH₂)₂CH₃ | C₃₃H₃₆N₈O₃ | 593.29 | 593.2 |
| 6 | —CH₃ | C₃₁H₃₂N₈O₃ | 565.26 | 565.6 |

1. (R)-4-Phenyl-3-[(5-propyl-1-{6-[2-(1H-tetrazol-5-yl)phenyl]pyridin-3-ylmethyl}-1H-pyrazole-3-carbonyl)amino]butyric acid isopropyl ester (TFA salt)
2. (R)-4-Phenyl-3-[(5-propyl-1-{6-[2-(1H-tetrazol-5-yl)phenyl]pyridin-3-ylmethyl}-1H-pyrazole-3-carbonyl)amino]butyric acid butyl ester (TFA salt)
3. (R)-4-Phenyl-3-[(5-propyl-1-{6-[2-(1H-tetrazol-5-yl)phenyl]pyridin-3-ylmethyl}-1H-pyrazole-3-carbonyl)amino]butyric acid pentyl ester (TFA salt)
4. (R)-4-Phenyl-3-[(5-propyl-1-{6-[2-(1H-tetrazol-5-yl)phenyl]pyridin-3-ylmethyl}-1H-pyrazole-3-carbonyl)amino]butyric acid ethyl ester (TFA salt)
5. (R)-4-Phenyl-3-[(5-propyl-1-{6-[2-(1H-tetrazol-5-yl)phenyl]pyridin-3-ylmethyl}-1H-pyrazole-3-carbonyl)amino]butyric acid propyl ester (TFA salt)
6. (R)-4-Phenyl-3-[(5-propyl-1-{6-[2-(1H-tetrazol-5-yl)phenyl]pyridin-3-ylmethyl}-1H-pyrazole-3-carbonyl)amino]butyric acid methyl ester (TFA salt)

Example 23

Following the procedures described in the examples above, and substituting the appropriate starting materials and reagents, compound 23-1 to 23-4 having the following formula can also be prepared:

| # | $R^1$ | $R^4$ | $R^5$ |
|---|---|---|---|
| 1 | tetrazole | —CH(OH)—COOH | benzyl |
| 2 | tetrazole | —CH₂—COOH | benzyl |
| 3 | —SO₂NHC(O)CH₃ | —CH(OH)—COOH | benzyl |
| 4 | —SO₂NHC(O)OCH₃ | —CH(OH)—COOH | benzyl |

Example 24

Following the procedures described in the examples above, and substituting the appropriate starting materials and reagents, compound 24-1 to 24-4 having the following formula can also be prepared:

| # | $R^1$ | $R^4$ | $R^5$ |
|---|---|---|---|
| 1 | tetrazole | —CH₂—COOH | 2-Cl-benzyl |
| 2 | tetrazole | —CH₂—COOH | 2-CF₃-benzyl |
| 3 | tetrazole | —CH₂—COOH | 2-F-benzyl |
| 4 | tetrazole | —CH(OH)—COOH | benzyl |
| 5 | —SO₂NHC(O)CH₃ | —CH(OH)—COOH | benzyl |

Assay 1

A. $AT_1$ and $AT_2$ Radioligand Binding Assays

These in vitro assays were used to assess the ability of test compounds to bind to the $AT_1$ and the $AT_2$ receptors.

Membrane Preparation from Cells Expressing Human $AT_1$ or $AT_2$ Receptors

Chinese hamster ovary (CHO-K1) derived cell lines stably expressing the cloned human $AT_1$ or $AT_2$ receptors, respectively, were grown in HAM's-F 12 medium supplemented with 10% fetal bovine serum, 10 μg/ml penicillin/streptomycin, and 500 μg/ml geneticin in a 5% $CO_2$ humidified incubator at 37° C. $AT_2$ receptor expressing cells were grown in the additional presence of 100 nM PD123,319 ($AT_2$ antagonist). When cultures reached 80-95% confluence, the cells were washed thoroughly in PBS and lifted with 5 mM EDTA. Cells were pelleted by centrifugation and snap frozen in MeOH-dry ice and stored at −80° C. until further use.

For membrane preparation, cell pellets were resuspended in lysis buffer (25 mM Tris/HCl pH 7.5 at 4° C., 1 mM EDTA, and one tablet of Complete Protease Inhibitor Cocktail Tablets with 2 mM EDTA per 50 mL buffer (Roche cat.#1697498, Roche Molecular Biochemicals, Indianapolis, Ind.)) and homogenized using a tight-fitting Dounce glass homogenizer (10 strokes) on ice. The homogenate was centrifuged at 1000×g, the supernatant was collected and centrifuged at 20,000×g. The final pellet was resuspended in membrane buffer (75 mM Tris/HCl pH 7.5, 12.5 mM MgCl₂, 0.3 mM EDTA, 1 mM EGTA, 250 mM sucrose at 4° C.) and homogenized by extrusion through a 20 G gauge needle.

Protein concentration of the membrane suspension was determined by the method described in Bradford (1976) *Anal Biochem.* 72:248-54. Membranes were snap frozen in MeOH-dry ice and stored at −80° C. until further use.

Ligand Binding Assay to Determine Compound Affinities for the Human $AT_1$ and $AT_2$ Angiotensin Receptors Binding assays were performed in 96-well Acrowell filter plates (Pall Inc., cat.#5020) in a total assay volume of 100 µL, with 0.2 µg membrane protein for membranes containing the human $AT_1$ receptor, or 2 µg membrane protein for membranes containing the human $AT_2$ receptor in assay buffer (50 mM Tris/HCl pH 7.5 at 20° C., 5 mM $MgCl_2$, 25 µM EDTA, 0.025% BSA). Saturation binding studies for determination of $K_d$ values of the ligand were done using N-terminally Europium-labeled angiotensin-II ([Eu]AngII, H-(Eu-$N^1$)-Ahx-Asp-Arg-Val-Tyr-Ile-His-Pro-Phe-OH; PerkinElmer, Boston, Mass.) at 8 different concentrations ranging from 0.1 nM to 30 nM. Displacement assays for determination of $pK_i$ values of test compounds were done with [Eu]AngII at 2 nM and 11 different concentrations of drug ranging from 1 µM to 10 µM. Drugs were dissolved to a concentration of 1 mM in DMSO and from there serially diluted into assay buffer. Non-specific binding was determined in the presence of 10 µM unlabeled angiotensin-II. Assays were incubated for 120 minutes in the dark, at room temperature or 37° C., and binding reactions were terminated by rapid filtration through the Acrowell filter plates followed by three washes with 200 µL ice cold wash buffer (50 mM Tris/HCl pH 7.5 at 4° C., 5 mM $MgCl_2$) using a Waters filtration manifold. Plates were tapped dry and incubated with 50 µl DELFIA Enhancement Solution (PerkinElmer cat.#4001-0010) at room temperature for 5 minutes on a shaker. Filter-bound [Eu]AngII was quantitated immediately on a Fusion plate reader (PerkinElmer) using Time Resolved Fluorescence (TRF). Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 10 µM angiotensin II. $K_i$ values for drugs were calculated from observed $IC_{50}$ values and the $K_d$ value of [Eu]AngII according to the Cheng-Prusoff equation described in Cheng et al. (1973) *Biochem Pharmacol.* 22 (23):3099-108. Selectivities of test compounds for the $AT_1$ receptor over the $AT_2$ receptor were calculated as the ratio of $AT_2K_i/AT_1K_i$. Binding affinities of test compounds were expressed as negative decadic logarithms of the $K_i$ values ($pK_i$).

In this assay, a higher $pK_i$ value indicates that the test compound has a higher binding affinity for the receptor tested.

B. In Vitro Assays for the Quantitation of Inhibitor Potencies ($IC_{50}$) at Human and Rat NEP, and Human ACE The inhibitory activities of compounds at human and rat NEP and human ACE were determined using in vitro assays as described below.

Extraction of NEP Activity from Rat Kidneys

Rat NEP was prepared from the kidneys of adult Sprague Dawley rats. Whole kidneys were washed in cold PBS and brought up in ice-cold lysis buffer (1% Triton X-114, 150 mM NaCl, 50 mM Tris pH 7.5; Bordier (1981) *J. Biol. Chem.* 256:1604-1607) in a ratio of 5 mL of buffer for every gram of kidney. Samples were homogenized using a polytron hand held tissue grinder on ice. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with BSA as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-BK2 (Mca-Arg-Pro-Pro-Gly-Phe-Ser-Ala-Phe-Lys(Dnp)-OH; Johnson et al. (2000) *Anal. Biochem.* 286: 112-118) was used for the human NEP and ACE assays, and Mca-RRL (Mca-DArg-Arg-Leu-(Dnp)-OH; Medeiros et al. (1997) *Braz. J. Med. Biol. Res.* 30:1157-1162) was used for the rat NEP assay (both from Anaspec, San Jose, Calif.).

The assays were performed in 384-well white opaque plates at room temperature using the respective fluorogenic peptides at a concentration of 10 µM in assay buffer (50 mM Tris/HCl at 25° C., 100 mM NaCl, 0.01% Tween-20, 1 µM Zn, 0.025% BSA). Human NEP and human ACE were used at concentrations that resulted in quantitative proteolysis of 5 µM of Mca-BK2 within 20 minutes at room temperature. The rat NEP enzyme preparation was used at a concentration that yielded quantitative proteolysis of 3 µM of Mca-RRL within 20 minutes at room temperature.

Test compounds were diluted to 12 concentrations from 10 µM to 20 pM in Assay Buffer. Assays were started by adding 25 µL of enzyme to 12.5 µL of test compound at each of the 12 concentrations. Test compounds were allowed to equilibrate with the enzyme for 10 minutes before 12.5 µL of the fluorogenic substrates were added to initiate the reaction. Reactions were terminated by the addition of 10 µL of 3.6% glacial acetic acid after 20 minutes of incubation.

For sulfhydryl-containing test compounds, the test compounds may be diluted in Assay Buffer containing a 400 µM concentration of tris(2-carboxyethyl)phosphine hydrochloride (Thermo Scientific, Rockford, Ill.) (TCEP). The test compounds are then incubated for 40 minutes at room temperature (to allow for dimer cleavage) before adding the enzyme. Test compounds are then allowed to equilibrate with the enzyme for 20 minutes before adding the fluorogenic substrates. Reactions are terminated as above.

Plates were read on a fluorometer with excitation and emission wavelengths set to 320 nm and 405 nm, respectively. Raw data (relative fluorescence units) were normalized to % activity from the average high readings (no inhibition, 100% enzyme activity) and average low readings (full inhibition, highest inhibitor concentration, 0% enzyme activity) using three standard NEP and ACE inhibitors, respectively. Non-linear regression of the normalized data was performed using a one site competition model (GraphPad Software, Inc., San Diego, Calif.). Data were reported as $pIC_{50}$ values.

Compounds of the invention were tested in these or similar assays and were found to have $pK_i$ values at the $AT_1$ receptor and $pIC_{50}$ values for the NEP enzyme as set forth below.

| Ex. | AT$_1$ pK$_i$ | NEP pIC$_{50}$ |
|---|---|---|
| 1 | ≥8.0 | ≥6.0 |
| 2 | ≥8.0 | ≥5.0 |
| 3-1 | ≥8.0 | ≥7.0 |
| 3-2 | ≥8.0 | ≥7.0 |
| 3-3 | ≥7.0 | ≥7.0 |
| 3-4 | ≥8.0 | ≥7.0 |
| 3-5 | ≥7.0 | ≥7.0 |
| 3-6 | ≥8.0 | ≥7.0 |
| 3-7 | ≥8.0 | ≥7.0 |
| 3-8 | ≥7.0 | ≥6.0 |
| 3-9 | ≥7.0 | ≥6.0 |
| 3-10 | ≥8.0 | ≥6.0 |
| 3-11 | ≥8.0 | ≥7.0 |
| 3-12 | ≥8.0 | ≥5.0* |
| 3-13 | ≥8.0 | ≥6.0 |
| 3-14 | ≥8.0 | ≥7.0 |
| 3-15 | ≥8.0 | ≥7.0 |
| 3-16 | ≥8.0 | ≥7.0 |
| 3-17 | ≥8.0 | ≥7.0 |
| 3-18 | ≥8.0 | ≥6.0 |
| 3-19 | ≥7.0 | ≥6.0 |
| 3-20 | ≥7.0 | ≥6.0 |
| 3-21 | ≥7.0 | ≥6.0 |
| 3-22 | ≥7.0 | ≥7.0 |
| 3-23 | ≥8.0 | ≥7.0 |
| 3-24 | ≥8.0 | ≥6.0 |
| 3-25 | ≥8.0 | ≥7.0 |
| 3-26 | ≥7.0 | ≥7.0 |
| 3-27 | ≥8.0 | ≥5.0* |
| 3-28 | ≥8.0 | ≥5.0* |
| 3-29 | ≥8.0 | ≥5.0* |
| 3-30 | ≥8.0 | ≥5.0 |
| 3-31 | ≥7.0 | ≥5.0 |
| 3-32 | ≥7.0 | ≥5.0 |
| 3-33 | ≥8.0 | ≥5.0 |
| 3-34 | ≥8.0 | ≥5.0 |
| 3-35 | ≥8.0 | ≥5.0 |
| 3-36 | ≥7.0 | ≥6.0 |
| 3-37 | ≥7.0 | ≥5.0 |
| 3-38 | ≥7.0 | ≥7.0 |
| 4 | ≥8.0 | ≥7.0 |
| 5 | ≥8.0 | ≥7.0 |
| 6-1 | ≥8.0 | ≥7.0 |
| 6-2 | ≥8.0 | ≥7.0 |
| 6-3 | ≥7.0 | ≥6.0 |
| 6-4 | ≥8.0 | ≥7.0 |
| 6-5 | ≥8.0 | ≥7.0 |
| 6-6 | ≥8.0 | ≥7.0 |
| 6-7 | ≥8.0 | ≥7.0 |
| 6-8 | ≥8.0 | ≥6.0 |
| 6-9 | ≥8.0 | ≥7.0 |
| 6-10 | ≥7.0 | ≥7.0 |
| 6-11 | ≥8.0 | ≥6.0 |
| 6-12 | ≥8.0 | ≥6.0 |
| 6-13 | ≥8.0 | ≥7.0 |
| 6-14 | ≥8.0 | ≥7.0 |
| 6-15 | ≥8.0 | ≥7.0 |
| 6-16 | ≥8.0 | ≥7.0 |
| 6-17 | ≥8.0 | ≥7.0 |
| 6-18 | ≥8.0 | ≥7.0 |
| 6-19 | ≥8.0 | ≥7.0 |
| 6-20 | ≥8.0 | ≥7.0 |
| 6-21 | ≥8.0 | ≥7.0 |
| 6-22 | ≥8.0 | ≥7.0 |
| 6-23 | ≥8.0 | ≥7.0 |
| 6-24 | ≥8.0 | ≥5.0 |
| 6-25 | ≥8.0 | ≥6.0 |
| 6-26 | ≥8.0 | ≥6.0 |
| 6-27 | ≥8.0 | ≥6.0 |
| 6-28 | ≥8.0 | ≥5.0 |
| 7-1 | ≥8.0 | ≥6.0 |
| 7-2 | ≥8.0 | ≥7.0 |
| 7-3 | ≥8.0 | ≥6.0 |
| 7-4 | ≥8.0 | ≥6.0 |
| 7-5 | ≥8.0 | ≥6.0 |
| 7-6 | ≥8.0 | ≥6.0 |
| 7-7 | ≥8.0 | ≥6.0 |
| 7-8 | ≥8.0 | ≥6.0 |
| 7-9 | ≥8.0 | ≥6.0 |
| 7-10 | ≥8.0 | ≥7.0 |
| 7-11 | ≥8.0 | ≥7.0 |
| 7-12 | ≥8.0 | ≥6.0 |
| 7-13 | ≥8.0 | ≥7.0 |
| 7-14 | ≥8.0 | ≥7.0 |
| 7-15 | ≥8.0 | ≥7.0 |
| 7-16 | ≥8.0 | ≥7.0 |
| 7-17 | ≥8.0 | ≥7.0 |
| 7-18 | ≥8.0 | ≥6.0 |
| 7-19 | ≥7.0 | ≥6.0 |
| 7-20 | ≥8.0 | ≥7.0 |
| 7-21 | ≥7.0 | ≥7.0 |
| 7-22 | ≥7.0 | ≥7.0 |
| 8 | ≥7.0 | ≥7.0 |
| 9-1 | ≥7.0 | ≥7.0 |
| 9-2 | ≥7.0 | ≥7.0 |
| 9-3 | ≥7.0 | ≥7.0 |
| 9-4 | ≥7.0 | ≥7.0 |
| 9-5 | ≥7.0 | ≥7.0 |
| 9-6 | ≥7.0 | ≥7.0 |
| 9-7 | ≥7.0 | ≥7.0 |
| 10 | ≥8.0 | ≥7.0 |
| 11 | ≥8.0 | ≥7.0 |
| 12 | ≥8.0 | ≥7.0 |
| 13 | ≥7.0 | ≥7.0 |
| 14-1 | ≥8.0 | ≥7.0 |
| 14-2 | ≥8.0 | ≥7.0 |
| 14-3 | ≥7.0 | ≥7.0 |
| 14-4 | ≥8.0 | ≥7.0 |
| 14-5 | ≥8.0 | ≥7.0 |
| 14-6 | ≥8.0 | ≥7.0 |
| 14-7 | ≥8.0 | ≥7.0 |
| 14-8 | ≥8.0 | ≥6.0 |
| 14-9 | ≥8.0 | ≥7.0 |
| 14-10 | ≥8.0 | ≥7.0 |
| 14-11 | ≥8.0 | ≥6.0 |
| 14-12 | ≥8.0 | ≥7.0 |
| 14-13 | ≥8.0 | ≥7.0 |
| 14-14 | ≥8.0 | ≥6.0 |
| 14-15 | ≥8.0 | ≥6.0 |
| 15-1 | ≥8.0 | ≥6.0 |
| 15-2 | ≥7.0 | ≥6.0 |
| 15-3 | ≥7.0 | ≥7.0 |
| 15-4 | ≥7.0 | ≥6.0 |
| 16-1 | ≥8.0 | ≥7.0 |
| 16-2 | ≥8.0 | ≥6.0 |
| 16-3 | ≥8.0 | ≥7.0 |
| 16-4 | ≥8.0 | ≥6.0 |
| 16-5 | ≥8.0 | ≥6.0 |
| 16-6 | ≥7.0 | ≥7.0 |
| 16-7 | ≥8.0 | ≥7.0 |
| 15-1 | ≥8.0 | ≥6.0 |
| 17-2 | ≥8.0 | ≥6.0 |
| 17-3 | ≥8.0 | ≥7.0 |
| 17-4 | ≥8.0 | ≥6.0 |
| 17-5 | ≥7.0 | ≥7.0 |
| 17-6 | ≥8.0 | ≥6.0 |
| 18 | ≥7.0 | ≥6.0 |

*These compounds are prodrugs and therefore may not exhibit NEP activity in an in vitro assay.

The compounds of Examples 19, 20, 21, and 22 are prodrugs of the compounds of Examples 3-16, 10, 12, and 14-6, respectively, and were not tested in this assay. Assuming full conversion of the prodrug to the active compound, the prodrugs are expected to have similar in vitro and in vivo AT$_1$ activity and equivalent or better in vivo NEP activity as their active counterpart.

Assay 2

Pharmacodynamic (PD) Assay for ACE, $AT_1$, and NEP Activity in Anesthetized Rats Male, Sprague Dawley, normotensive rats are anesthetized with 120 mg/kg (i.p.) of inactin. Once anesthetized, the jugular vein, carotid artery (PE 50 tubing) and bladder (URI-1 urinary silicone catheter) are cannulated and a tracheotomy is performed (Teflon Needle, size 14 gauge) to faciliate spontaneous respiration. The animals are then allowed a 60 minute stablization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of angiotensin (AngI, 1.0 µg/kg, for ACE inhibitor activity; AngII, 0.1 µg/kg, for $AT_1$ receptor antagonist activity) at 15 minutes apart. At 15 minutes post-second dose of angiotensin (AngI or AngII), the animals are treated with vehicle or test compound. Five minutes later, the animals are additionally treated with a bolus i.v. injection of atrial natriuretic peptide (ANP; 30 µg/kg). Urine collection (into pre-weighted eppendorf tubes) is started immediately after the ANP treatment and continued for 60 minutes. At 30 and 60 minutes into urine collection, the animals are re-challenged with angiotensin (AngI or AngII). Blood pressure measurements are done using the Notocord system (Kalamazoo, Mich.). Urine samples are frozen at –20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition or $AT_1$ antagonism is assessed by quantifying the % inhibition of pressor response to AngI or AngII, respectively. NEP inhibition is assessed by quantifying the potentiation of ANP-induced elevation in urinary cGMP output.

Assay 3

In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site. Seven days prior to testing, the animals are either placed on a restricted low-salt diet with food containing 0.1% of sodium for sodium depleted SHRs (SD-SHR) or are placed on a normal diet for sodium repleted SHRs (SR-SHR). Two days prior to testing, the animals are surgically implemented with catheters into a carotid artery and the jugular vein (PESO polyethylene tubing) connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care. On the day of the experiment, the animals are placed in their cages and the catheters are connected via a swivel to a calibrated pressure transducer. After 1 hour of acclimation, a baseline measurement is taken over a period of at least five minutes. The animals are then dosed i.v. with vehicle or test compound in ascending cumulative doses every 60 minutes followed by a 0.3 mL saline to clear the catheter after each dose. Data is recorded continuously for the duration of the study using Notocord software (Kalamazoo, Mich.) and stored as electronic digital signals. In some studies, the effects of a single intravenous or oral (gavage) dose are monitored for at least 6 hours after dosing. Parameters measured are blood pressure (systolic, diastolic and mean arterial pressure) and heart rate.

Assay 4

In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet. One week after the start of the high salt diet, a DOCA-salt pellet (100 mg, 21 days release time, Innovative Research of America, Sarasota, Fla.) is implanted subcutaneously and unilateral nephrectomy is performed. On 16 or 17 days post DOCA-salt pellet implantation, animals are implanted surgically with catheters into a carotid artery and the jugular vein with a PESO polyethylene tubing, which in turn was connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care.

On the day of the experiment, each animal is kept in its cage and connected via a swivel to a calibrated pressure transducer. After 1 hour of acclimation, a baseline measurement is taken over a period of at least five minutes. The animals are then dosed i.v. with a vehicle or test compound in escalating cumulative doses every 60 minutes followed by 0.3 mL of saline to flush the catheter after each dose. In some studies, the effects of a single intravenous or oral (gavage) dose is tested and monitored for at least 6 hours after dosing. Data is recorded continuously for the duration of the study using Notocord software (Kalamazoo, Mich.) and stored as electronic digital signals. Parameters measured are blood pressure (systolic, diastolic and mean arterial pressure) and heart rate. For cumulative and single dosing, the percentage change in mean arterial pressure (MAP, mmHg) or heart rate (HR, bpm) is determined as described for Assay 3.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A compound of formula:

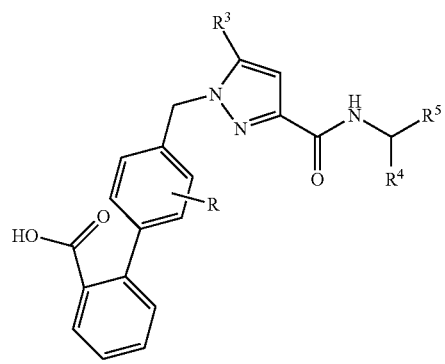

where: R is 3-fluoro, $R^3$ is propyl, $R^4$ is —$CH_2SH$, and $R^5$ is i-butyl; or a pharmaceutically acceptable salt thereof.

2. The compound of claim 1, which is 3'-fluoro-4'-[3-((R)-1-mercaptomethyl-3-methylbutylcarbamoyl)-5-propylpyrazol-1-ylmethyl]biphenyl-2-carboxylic acid.

3. A pharmaceutical composition comprising the compound of claim 1 and a pharmaceutically acceptable carrier.

4. The pharmaceutical composition of claim 3 further comprising a second therapeutic agent selected from the group consisting of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof.

5. A method for ameliorating, suppressing, or alleviating the symptoms of hypertension or heart failure, comprising administering to a patient a therapeutically effective amount of a compound of claim 1.

* * * * *